(12) United States Patent
Lawrence et al.

(10) Patent No.: US 7,087,574 B2
(45) Date of Patent: *Aug. 8, 2006

(54) BRAIN ASSOCIATED INHIBITOR OF TISSUE-TYPE PLASMINOGEN ACTIVATOR

(75) Inventors: Daniel A. Lawrence, Derwood, MD (US); Manuel Yepes, Alexandria, VA (US); Maria Sandkvist, Derwood, MD (US); Timothy A. Coleman, Gaithersburg, MD (US); Michael K. K. Wong, Wexford, PA (US)

(73) Assignees: Human Genome Sciences, Inc., Rockville, MD (US); The American Red Cross, Falls Church, VA (US)

( * ) Notice: Subject to any disclaimer, the term of this patent is extended or adjusted under 35 U.S.C. 154(b) by 90 days.

This patent is subject to a terminal disclaimer.

(21) Appl. No.: 10/355,208

(22) Filed: Jan. 31, 2003

(65) Prior Publication Data
US 2004/0038880 A1    Feb. 26, 2004

Related U.S. Application Data

(60) Division of application No. 09/957,485, filed on Sep. 21, 2001, now abandoned, which is a continuation of application No. 09/521,664, filed on Mar. 8, 2000, now abandoned.

(60) Provisional application No. 60/123,704, filed on Mar. 10, 1999.

(51) Int. Cl.
*A61K 38/57* (2006.01)
*A61K 39/00* (2006.01)
*C07K 14/47* (2006.01)
*C12P 21/06* (2006.01)

(52) U.S. Cl. .............. 514/12; 514/2; 530/350; 424/192.1; 435/69.1

(58) Field of Classification Search .......... 514/2, 514/12; 530/350; 424/184.1, 185.1, 192.1; 435/69.1
See application file for complete search history.

(56) References Cited

U.S. PATENT DOCUMENTS

| | | | |
|---|---|---|---|
| 5,011,912 A | 4/1991 | Hopp et al. | |
| 5,278,049 A | 1/1994 | Baker et al. | |
| 5,495,001 A | 2/1996 | McGrogan et al. | |
| 5,700,924 A | 12/1997 | Braxton et al. | |
| 5,955,284 A | 9/1999 | Braxton et al. | |
| 6,008,020 A | 12/1999 | Hastings et al. | |
| 6,191,260 B1 | 2/2001 | Hastings et al. | |
| 6,541,452 B1* | 4/2003 | Hastings et al. | 514/12 |

FOREIGN PATENT DOCUMENTS

| | | |
|---|---|---|
| CA | 2226919 | 8/1999 |
| WO | WO96/40922 | 12/1996 |
| WO | WO98/16643 | 4/1998 |
| WO | WO99/41381 | 8/1999 |
| WO | WO00/53793 | 9/2000 |

OTHER PUBLICATIONS

Osterwalder et al. "Neuroserpin, an axonally secreted serine protease inhibitor," EMBO Journal 15:2944-2953 (1996).
Wiegand et al. "Cloning of the cDNA encoding human brain trypsinogen and characterization of its product," Gene 136:1676-175 (1993).
Bjork et al. "Kinetic characterization of the substrate reaction between a complex of antithrombin with a synthetic reactive-bond loop tetradecapeptide and four target proteinases of the inhibitor," J. Biol. Chem. 267(27):19047-19050 (1992).
Schrimpf et al. "Human neuroserpin (PI12): cDNA cloning and chromosomal localization to 3q26," Genomics 40:55-62 (1997).
Reilly et al. "Recombinant plasminogen activator inhibitor tyupe 1: a review of structural, functional, and biological aspects," Blood Coagulation and Fibrinolysis 5:73-81 (1994).
Eitzman et al. "Peptide-mediated inactivation of recombinant and platelet plasminogen activator inhibitort-1 in vitro," J. Clin. Invest. 95:2416-2420 (1995).
Lawrence et al. "Serpin reactive center lLoop mobility is required for inhibitor function but not for enzyme recognition," J. Biol. Chem. 269(44):27657-27662 (1994).
Schulze et al. "Structural transition of $\alpha_1$-antitrypsin by a peptide sequentially similar to β-strand s4A," Eur. J. Biochem. 194:51-56 (1990).
Lawrence et al. "Structure-function studies of the SERPIN plasminogen activtor inhibitor type 1," J. Biol. Chem. 265(33):20293-20301 (1990).
Lawrence et al. "Molecular Basis of Thrombosis and Hemostatsis," edited by High & Roberts, publ.: Marcel Dekke, Inc., pp. 517-543 (1995).
Berkenpas et al. "Molecular evolution of plasminogen activator inhibitor-1 functional stability," The EMBO J. 14(13):2969-2977 (1995).

(Continued)

Primary Examiner—Olga N. Chernyshev
(74) Attorney, Agent, or Firm—Human Genome Sciences, Inc.

(57) ABSTRACT

The present invention relates to a novel BAIT protein which is a member of serpin superfamily which is expressed primarily in brain tissue. In particular, isolated nucleic acid molecules are provided encoding the human and recombinant methods for producing the same. The invention further relates to screening methods for identifying agonists and antagonists of BAIT activity. Also provided are diagnostic methods for detecting nervous system-related disorders and therapeutic methods for treating nervous system-related disorders. Additionally, the present invention is related to methods of treating patients with BAIT polynucleotides or polypeptides, wherein said patients have had a stroke.

9 Claims, 24 Drawing Sheets

OTHER PUBLICATIONS

Houenou et al. "A serine protease inhibitor, protease nexin I, rescues motoneurons from naturally occurring and axotomy-induced cell death," PNAS USA 92:895-899 (1995).
Genbank Accession No. R12152 (1995).
Genbank Accession No. AA115876 (1996).
Genbank Accession No. AA164563 (1996).
Genbank Accession No. AA165401 (1996).
Genbank Accession No. F07041 (1995).
Genbank Accession No. H09005 (1995).
Genbank Accession No. H09572 (1995).
Genbank Accession No. N47859 (1996).
Genbank Accession No. R42394 (1995).
Genbank Accession No. R14666 (1995).
Genbank Accession No. N50314 (1996).
Genbank Accession No. R15085 (1995).
Genbank Accession No. N53887 (1996).
Hillier, et al. "Generation and analysis of 280,000 Human Expressed Sequence Tags," Genome Research, 6:807-828 (1996).
Yepes et al., "Neuroserpin reduces cerebral infarct volume and protects neurons from ischemia-induced apoptosis," Blood 96:569-576 (2000).
Yepes, Manuel; Sandkvist, Maria; Smith, Elizabeth; Coleman, Timothy; Cohan, Stanley L.; Lawrence, Daniel A.: "Neuroserpin decreases stroke volume and inhibits apoptosis in an animal model of focal cerebral ischemia/reperfusion" [Abstract submitted to] $2^{nd}$ International Symposium on the Structure and Biology of Serpins. Jun. 27-Jul. 1, 1999; Cambridge, UK.
Yepes, Manuel; Sandkvist, Maria; Smith, Elizabeth; Coleman, Timothy; Cohan, Stanley L.; Lawrence, Daniel A.: "Neuroserpin, A brain associated tPA inhibitor, decreases stroke volume and inhibits apoptosis in area of ischemic penumbra" [Abstract submitted to] XVIIth Congress of the International Society on Thrombosis and Haemostasis; Aug. 14-21, 1999, Washington, D.C., USA.

Krueger S.R., et al., "Expression of neuroserpin, an inhibitor of tissue plasminogen activator, in the developing and adult nervous system of the mouse." Journal of Neuroscience, vol. 17, No. 23, pp. 8984-8996 (1997).
Berger P., et al. "Structure of the mouse gene for the serine protease inhibitor neuroserpin (PI12)." Gene, vol. 214, pp. 25-33 (1998).
Osterwalder T, et al. "The axonally secreted serine proteinase inhibitor, neuroserpin, inhibits plasminogen activators and plasmin but not thrombin." J. BioL. Chem., vol. 273, No. 4, pp. 2312-2321 (1998).
Hill, R.M., et al., "Neuroserpin is expressed in the pituitary and adrenal glands and induces the extension of neurite-like processes in AtT-20 cells." Biochem. J., vol. 345, pp. 595-601 (2000).
Hastings GA, Coleman TA, Haudenschild CC, Stefansson S, Smith EP, Barthlow R, Cherry S, Sandkvist M, Lawrence DA, "Neuroserpin, a brain-associated inhibitor of tissue plasminogen activator is localized primarily in neurons. Implications for the regulation of motor learning and neuronal survival" J. Biol. Chem. 272:33062-33067 (1997).
Yepes, Manuel; Coleman, Timothy A.; Lawrence, Daniel A.; "Neuroserpin protects neurons from excitotoxin-induced cell death" Abstract submitted First Chianti Meeting, Apr. 27-May 1, 2001, Siena-Italy.
Bjork et al. "Conversion of antithrombin from an inhibitor of thrombin to a substrate with reduced heparin affinity and enhanced conformational stability by binding of a tetradecapeptide corresponding to the $P_1$ to $P_{14}$ Region of the putative reactive bond loop of the inhibitor," J. Biol. Chem. 267(3):1976-1982 (1992).
Kvassman et al. "The acid stabilization of plasminogen activator inhibitor-1 depends on protonation of a single group that affects loop insertion into β-sheet A," J. Biol. Chem. 270(46):27942-27947 (1995).

* cited by examiner

```
  1 CAGCGGAGCCGAGCACAGTCCGCCCGAGCACAAGCTCCAGCATCCGTCAGGGTTGCAGGTGTGTGGGAGGCTTGAAACTGTTACAATATGGCTTTCCTTGGACTCTTCTCTTTGCTGGT   120
                                                                                           M  A  F  L  G  L  F  S  L  L  V       11

121 TCTGCAAAGTATGGCTACAGGGGCCACTTTCCCTGAGGAAGCCATTGCTGACTTGTCAGTGAATATGTATAATCGTCTTAGAGCCACTGGTGAAGATGAAAATATTCTCTCTCCATT     240
 12  L  Q  S  M  A  T  G  A  T  F  P  E  E  A  I  A  D  L  S  V  N  M  Y  N  R  L  R  A  T  G  E  D  E  N  I  L  F  S  P  L       51

241 GAGTATTGCTCTTGCAATGGAAATGGAACTGGGGGCCCAAGGATCTACCCAGAAAGAAATCCGCCACTCAATGGGATATGACAGCCTAAAAAATGGTGAAGAATTTTCTTTCTTGAA     360
 52  S  I  A  L  A  M  G  M  M  E  L  G  A  Q  G  S  T  Q  K  E  I  R  H  S  M  G  Y  D  S  L  K  N  G  E  E  F  S  F  L  K      91

361 GGAGTTTTCAAACATGGTAACGTAAAGAGCACAATATGTGAAAAATTGCCAATTCCTTGTTTGTGCAAAATGGCAGTTTTCATGTCAATGAGGAGTTTTTGCAAATGATGAAAAAATA     480
 92  E  F  S  N  M  V  T  A  K  E  S  Q  Y  V  V  M  K  I  A  N  S  L  F  V  Q  N  G  F  H  V  N  E  E  F  L  Q  M  M  K  K  Y    131

481 TTTTAATGCAGCAGTGAATCATGTGGACTTCAGTCAAAATGTAGCGCTGGCCAACTACATCAATAAGTGGGTGGAGAATAACACAAACATCGTCAAAGATTTGGTATCCCAAGGCA    600
132  F  N  A  A  V  N  H  V  D  F  S  Q  N  V  A  V  A  N  Y  I  N  K  W  V  E  N  N  T  N  N  L  V  K  D  L  V  S  P  R  D     171

601 TTTTGATGCTGCCACTTATCTGGCCCTCATTAATGCTGTCTATTTCAAGGGGAACTGGAAGTCCCAGTTTAGGCCTGAAAATACTAGAACCTTTTCTTCACTAAAGATGATGAAGTGA     720
172  F  D  A  A  T  Y  L  A  L  I  N  A  V  Y  F  K  G  N  W  K  S  Q  F  R  P  E  N  T  R  T  F  S  F  T  K  D  D  E  S  E    211

721 AGTCCAAATTCCAATGATGTATCCAACGAAGACAGAGAATTTAGTGATGGCTCCAATGAAGCTCCTAGAATGCCTAGAATACCATATGAAGGAGATGAAAT     840
212  V  Q  I  P  M  M  Y  Q  Q  G  E  F  Y  Y  G  E  F  S  D  G  S  N  E  A  G  G  I  Y  Q  V  L  E  I  P  Y  E  G  D  E  I    251

841 AAGCATGATGCTGGTGCTGTCCAGACAGGAAGTTCCTCTTGCTACTCTGGAGCCATTAGTCAAAGCACAGCTGGTTGAAGAATGGGCAAACTCTGTGAAGAAGCAAAAGTAGAAGTATA    960
252  S  M  M  L  V  L  S  R  Q  E  V  P  L  A  T  L  E  P  L  V  K  A  Q  L  V  E  E  W  A  N  S  V  K  K  Q  K  V  E  V  Y    291
```

```
                                                                                                              100
BAIT      .........     ..........  ..........  ..........  ..........  ..........  ..........  .....EAIAD  LSVNMYNRLR
CHKNSP    .........     ..MYFLGLLS  LLVLPSKAFK  TNFPD.....  ..........  ..........  ..........  .....ETIAE  LSVNVYNQLR
BOVPAI1   .........     ......MRMSP VFACLALGLA  LIFGE.....  ..........  ..........  .CSASYQP    QSAAASLATD  FGVKVFQQVV
RATGDN1   .........     .......MNWHFP FFILTTVTLS SVYSQ.....  ..........  ..........  ..LNSLSLE.  ......ELGSD TGIQVFNQII
MusATIII  MYSPGAGSGA AGERKLCLLS LLLIGALGCA ICHGNPVDDI CIAKPRDIPV NPLCIYRSPG KKATEEDGSE QKVPEATNRR VWELSKANSR FATNFYQHLA 101                                                                                                 200
BAIT      ATGED.ENIL FSPLSIALAM GMMELGAQGS TQKEIRHSMG YDS....LKN GEEFSFLKEF SNMVTAKESQ YVMKIANSLF VQNGFHVNEE FLQMMKKYFN
CHKNSP    AARED.ENIL FCPLSIAIAM GMIELGAHGT TLKEIRHSLG FDSL....KN GEEFTFLKDL SDMATTEESH YVLNMANSLY VQNGFHVSEK FLQLVKKYFK
BOVPAI1   RASKD.RNVV FSPYGVASVL AMLQLTTGGE TRQQIQEAMQ FKI....EEK GMAPAFHRLY KELMGPWNKD EI.STADAIF VQRDLELVHG FMPNFFRLFR
RATGDN1   KSQPH.ENVV ISPHGIASIL GMLQLGADGR TKKQLSTVMR YNV....N.. GVGKVLKKIN KAIVSKKNKD IV.TVANAVF VRNGFKVEVP FAARNKEVFQ
MusATIII  DSKNDNDNIF LSPLSISTAF AMTKLGACND TLKQLMEVFK FDTISEKTSD TLKRKANKS SDLVSANRLF GDKSLTFNES YQDVSEVVYG 201                                                                                                 300
BAIT      AAVNHVDFSQ .NVAVANYIN KWVENNTNNL VKDLVSPRDF DAA.TYLALI NAVYFKGNWK SQFRPENTRT FSFTKDDESE VQIPMMYQQG EFYYGEFSDG
CHKNSP    AEVENIDFSQ .SAAVATHIN KWVENHTNNM IKDFVSSRDF S.ALTHLVLI NAIYFKGNWK SQFRPENTRT FSFTKDDETE VQIPMMYQQG EFYYGEFSDG
BOVPAI1   TTVKQVDFSE .VERARFIVN DWVKRHTKGM ISDLLGEGAV D.QLTRLVLV NALYFNGQWK MPFPESNTHH RLFHKSDGST ISVPMMAQTN KFNYTEFTTP
RATGDN1   CEVQSVNFQD .PASACDAIN FWVKNETRGM IDNLLSPNLI DSALTKLVLV NAVYFKGLWK SRFQPENTKK RTFVACDGKS YQVPMLAQLS VFRSGSTKTP
MusATIII  AKLQPLDFKE NPEQSRVTIN NWVANKTEGR NTIYFKGLWK SKFSPENTRK EPFYKVDGQS CPVPMMYQEG KFKYRRVAEG
```

FIG. 2A

```
         301                                                                                                    400
BAIT     SNEAGGIYQV LEIPYEGDEI SMMLVLSRQ. EVPLATLEPL VKAQLVEEWA NSVKKQKVEV YLPRFTVEQE IDLKDVLKAL GITEIF.IKD ANLTGL..SD
CHKNSP   SNEAGGIYQV LEIPYEGDEI SMMIVLSRQ. EVPLVTLEPL VKASLINEWA NSVKKQKVEV YLPRFTVEQE IDLKDVLKGL GITEVFSRS. ADLTAM..SD
BOVPAI1  ...DGRYYDI LELPYHGNTL SMIAAPYEK EVPLSALTSI LDAELISQWK GNMTRLTRLL VLPKFSLETE IDLRRPLENL GMTDMFRPSQ ADFSSF..SD
RATGDN1  ...NGLWYNF IELPYHGESI SMLIALPTES STPLSAIIPH ISTKTINSWM NTMVPKRMQL VLPKFTALAQ TDLKEPLKAL GITEMFEPSK ANFAKI..TR
MUSATIII T......QV LELPFKGDDI TMVLILP.KP EKSLAKVEQE LTPELLQEWL HMPRFRTEDG FSLKEQLQDM GLIDLFSPEK SQLPGIVAGG

P17                  P1 P1'
                         |                    | |
         401                                                                                                    500
BAIT     NKEIFLSKAI HKSFLEVNEE GSEAAAVSGM IAISR.MAVL YPQVIVDHPF FFLIRNRRTG TILFMGRVMH PETMNTSGHD FEEL........ ...........
CHKNSP   NKELYLAKAF HKAFLEVNEE GSEAAAASGM IAISR.MAVL YPQVIVDHPF FFLVRNRRTG TVLFMGRVMH PEAMNTSGHD FEEL........ ...........
BOVPAI1  QEFLYVSQAL QKVKIEVNES GTLASSSTAL VVSAR.MAP. .EEIIMDRPF LFVVRHNPTG TVLFMGQVME P........... ...........
RATGDN1  SESLHVSHIL QKAKIEVSED GTKAAVTTA ILIAR.SSP. .PWFIVDRPF LFCIRHNPTG AILFLGQVNK P........... ...........
MUSATIII RDDLYVSDAF HKAFLEVNEE GSEAAASTSV VITGRSLNPN RVTFKANRPF LVLIREVALN TIIFMGRVAN PCVN........ ...........
```

BAIT:     HUMAN BRAIN-ASSOCIATED INHIBITOR OF tPA
CHKNSP:   CHICKEN NEUROSERPIN
BOVPAI1:  BOVINE PLASMINOGEN ACTIVATOR INHIBITOR-1
RATGDN1:  RAT GLIAL-DERIVED NEXIN-1
MUSATIII: MOUSE ANTITHROMBIN III

\* COMPARISON WAS GENERATED WITH THE PILEUP MODULE OF THE GENETICS COMPUTER GROUP (WISCONSIN PACKAGE, VERSION 8) USING THE PARAMETERS- GAPWEIGHT: 3.000 GAPLENGTHWEIGHT: 0.100.

FIG. 2B

```
             1                                                                  50
HPBCT06R.gcg GGAAGTTCCT CTTGCTACTC TGGAGCCATT AGTCAAAGCA CAGCTGGTTG
HPBDG64R.gcg AGACAGGAAG TTCCTCTTGC TACTCTGGAG CCATTAGTCA AAGCACAGCT
HPBCR79R.gcg GGAAGTTCCT CTTGCTACTC TGGAGCCATT AGTCAAAGCA CAGCTGGTTG
HSDFB55S01X.gcg GAGCGGAGCG GAGCACAGTC CGCCGAGCAC AAGCTCCAGC ATCCGTCAG 51                                                                 100
HPBCT06R.gcg AAGAATGGGC AAACTCTGTG AAGAAGCAAA AAGTAGAAGT ATACCTGCCC
HPBDG64R.gcg GGTTGAAGAN TGGGCAAACT CTGTNAAGAA GCAAAAAGTA GAAGTATACC
HPBCR79R.gcg AAGAATGGGC AAACTCTGTG AAGAAGCAAA AAGTAGAAGT ATACCTGCCC
HSDFB55S01X.gcg GGGTTGCAGG TGTGTGGGAG GCTTGAAACT GTTACAATAT GGCTTTCCTT 101                                                                150
HPBCT06R.gcg AGGTTCACAG TGGAACAGGA AATTGATTTA AAAGATGTTT TGAAGGCTCT
HPBDG64R.gcg TGCCCAGGTT CACAGTGGAA CAGGAAATTN ATTTAAAAGA TGTTTTGAAG
HPBCR79R.gcg AGGTTCACAG TGGAACAGGA AATTGATTTA AAAGATGTTT TGAAGGCTCT
HSDFB55S01X.gcg GGACTCTTCT CTTTGCTGGT TCTGCAAAGT ATGGCTACAG GGGCCACTTT 151                                                                200
HPBCT06R.gcg TGGAATAACT GAAATTTTCA TCAAAGATGC AAATTTGACA GGCCTCTCTG
HPBDG64R.gcg GCTCTTGGAA TAACTGAAAT TTTCATCAAA GATGCAAATT TGACAGGCCT
HPBCR79R.gcg TGGAATAACT GAAATTTTCA TCAAAGATGC AAATTTGACA GGCCTCTCTG
HSDFB55S01X.gcg CCCTGAGGAA GCCATTGCTG ACTTGTCAGT GAATATGTAT AATCGTCTTA 201                                                                250
HPBCT06R.gcg ATAATAAGGA GATTTTTCTT TCCAAAGCAA TTCACAAGTC CTTCCTAGAG
HPBDG64R.gcg CTCTGATAAT AAGGAGATTT AAGGAGATTT TCNTTTCCAA AGCAATTCAC AAGTCCTTCC
HPBCR79R.gcg ATAATAAGGA GATTTTTCTT TCCAAAGCAA TTCACAAGTC CTTCCTAGAG
HSDFB55S01X.gcg GAGCCACTGG TGAAGATGAA AATATTCTCT TCTCTCCATT GAGTATTGCT
```

FIG.4A

```
              251                                                                    300
HPBCT06R.gcg  GTTAAATGAA GGAAGGCTCC AGAAGCTGCT GCTGGTCTTC AGGAATGATT
HPBDG64R.gcg  TAGAGGTTAA TGNAGGAGGC TCCAGAAGCT GCTGCTGTCT CAGGGATGAT
HPBCR79R.gcg  GTTAATGAAG AAGGCTCAGA AGCTGCTGCT TGTCTCAGGA ATGATTGCAA
HSDFB55S01X.gcg CTTGCAATGG GAATGATGGA ACTTGGGGCC CAAGGATCTA CCCAGAAAGA 301                                                                    350
HPBCT06R.gcg  TGCAATTAGT AGGGTTGGCT GTNCTGTATC CCTCAAGGTT ATTGTCGGCC
HPBDG64R.gcg  TTGCAATTTA NGTAGGNTGG GCTGTGCTGG TATCCNCAAG GTTATTTTTC
HPBCR79R.gcg  TTAGTAGGAT GGCTGTGCTG TATCCTCAAG GTTATTGTCG ACCATCCATT
HSDFB55S01X.gcg AATCCGCCAC TCAATGGGAT ATGACAGCCT AAAAAATGGT GAAGAATTTT 351                                                                    400
HPBCT06R.gcg  ATCC....... .......... .......... .......... ..........
HPBDG64R.gcg  GG........ .......... .......... .......... ..........
HPBCR79R.gcg  TTTCCTTTCT TATCAGAACC AGGGGACCTG GTACAATTCT ATTCATGGG.
HSDFB55S01X.gcg CTTTCTTGAA GGAGTTTTCA AACATGGTAA CTGCTAAAGA GAGCCAATAT 401                                                                    450
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg GTGATGAAAA TTGCCAATTC CTTGTTTGTG CAAAATGGAT TTCATGTCAA 451                                                                    500
HPBCT06R.gcg  .......... .......... .......... .......... ..........
HPBDG64R.gcg  .......... .......... .......... .......... ..........
HPBCR79R.gcg  .......... .......... .......... .......... ..........
HSDFB55S01X.gcg TGAGGAGTTT TTGCAAATGA TGAAAAAATA TTTTAATGCA GCAGTAAATC
```

FIG.4B

```
HPBCT06R.gcg       501  ................    ................    ................    ................    ................    550
HPBDG64R.gcg            ................    ................    ................    ................    ................
HPBCR79R.gcg            ................    ................    ................    ................    ................
HSDFB55S01X.gcg         ATGTGGACTT          CAGTCAAAAT          GTAGCCGTGG          CCAACTACAT          CAATAAGTGG HPBCT06R.gcg       551  ................    ................    ................    ................    ................    600
HPBDG64R.gcg            ................    ................    ................    ................    ................
HPBCR79R.gcg            ................    ................    ................    ................    ................
HSDFB55S01X.gcg         GTGGAGAATA          ACACAAACAA          TCTGGTGAAA          GATTTGGTAT          CCCCAAGGGA HPBCT06R.gcg       601  ................    ................    ................    ................    ................    650
HPBDG64R.gcg            ................    ................    ................    ................    ................
HPBCR79R.gcg            ................    ................    ................    ................    ................
HSDFB55S01X.gcg         TTTTGATGCT          GCCACTTATC          TGGCCCTCAT          TAATGCTGTC          TATTTCAAGG HPBCT06R.gcg       651  ................    ................    ................    ................    ................    700
HPBDG64R.gcg            ................    ................    ................    ................    ................
HPBCR79R.gcg            ................    ................    ................    ................    ................
HSDFB55S01X.gcg         GGAACTGGAA          GTCGCAGTTT          AGGCCTGAAA          ATACTAGAAC          CTTTTCTTTC HPBCT06R.gcg       701  ................    ................    ................    ................    ................    750
HPBDG64R.gcg            ................    ................    ................    ................    ................
HPBCR79R.gcg            ................    ................    ................    ................    ................
HSDFB55S01X.gcg         ACTAAAGATG          ATGAAAGTGA          AGTCCAAATT          CCAATGATGT          ATCAGCAAGG
```

FIG. 4C

```
              751                                                                       800
HPBCT06R.gcg  ........   ..........  ..........  ..........  ..........  ..........
HPBDG64R.gcg  ........   ..........  ..........  ..........  ..........  ..........
HPBCR79R.gcg  ........   ..........  ..........  ..........  ..........  ..........
HSDFB55S01X.gcg            AGAATTTTAT TATGGGGAAT TTAGTGATGG CTCCAATGAA GCTGGTGGTA 801                                                                       850
HPBCT06R.gcg  ........   ..........  ..........  ..........  ..........  ..........
HPBDG64R.gcg  ........   ..........  ..........  ..........  ..........  ..........
HPBCR79R.gcg  ........   ..........  ..........  ..........  ..........  ..........
HSDFB55S01X.gcg          TCTACCAAGT CCTAGAAATA CCATATGAAG GAGATGAAAT AAGCATGATG 851                                                                       900
HPBCT06R.gcg  ........   ..........  ..........  ..........  ..........  ..........
HPBDG64R.gcg  ........   ..........  ..........  ..........  ..........  ..........
HPBCR79R.gcg  ........   ..........  ..........  ..........  ..........  ..........
HSDFB55S01X.gcg          CTGGTGCTGT CCAGACAGGA AGTTCCTCTT GCTACTCTGG AGCCATTAGT 901                                                                       950
HPBCT06R.gcg  ........   ..........  ..........  ..........  ..........  ..........
HPBDG64R.gcg  ........   ..........  ..........  ..........  ..........  ..........
HPBCR79R.gcg  ........   ..........  ..........  ..........  ..........  ..........
HSDFB55S01X.gcg          CAAAGCACAG CTGGTTGAAG AATGGGCAAA CTCTGTGAAG AAGCAAAAAG 951                                                                      1000
HPBCT06R.gcg  ........   ..........  ..........  ..........  ..........  ..........
HPBDG64R.gcg  ........   ..........  ..........  ..........  ..........  ..........
HPBCR79R.gcg  ........   ..........  ..........  ..........  ..........  ..........
HSDFB55S01X.gcg          TAGAAGTATA CCTGCCCAGG TTCACAGTGG AACAGGAAAT TGATTTAAAA
```

FIG. 4D

```
                                                                                        1050
1001                                             ....|....|....|....|....|....|....|....|....|....|
HPBCT06R.gcg   ..................................................
HPBDG64R.gcg   ..................................................
HPBCR79R.gcg   ..................................................
HSDFB55S01X.gcg GATGTTTTGA AGGCTCTTGG AATAACTGAA ATTTCATCA AAGATGCAAA 1100
1051           ....|....|....|....|....|....|....|....|....|....|
HPBCT06R.gcg   ..................................................
HPBDG64R.gcg   ..................................................
HPBCR79R.gcg   ..................................................
HSDFB55S01X.gcg TTTGACAGGC CTCTCTGATA ATAAGGAGAT TTTTCTTTCC AAAGCAATTC 1150
1101           ....|....|....|....|....|....|....|....|....|....|
HPBCT06R.gcg   ..................................................
HPBDG64R.gcg   ..................................................
HPBCR79R.gcg   ..................................................
HSDFB55S01X.gcg ACAAGTCCTT CCTAGAGGTT AATGAAGAAG GCTCAGAAGC TGCTGCTGTC 1200
1151           ....|....|....|....|....|....|....|....|....|....|
HPBCT06R.gcg   ..................................................
HPBDG64R.gcg   ..................................................
HPBCR79R.gcg   ..................................................
HSDFB55S01X.gcg TCAGGAATGA TTGCAATTAG TAGGATGGCT GTGCTGTATC CTCAAGTTAT 1250
1201           ....|....|....|....|....|....|....|....|....|....|
HPBCT06R.gcg   ..................................................
HPBDG64R.gcg   ..................................................
HPBCR79R.gcg   ..................................................
HSDFB55S01X.gcg TGTCGACCAT CCATTTTTCT TTCTTATCAG AAACAGGAGA ACTGGTACAA
```

FIG.4E

```
HPBCT06R.gcg     1251  . . . . . . . . . .  . . . . . . . . . .  . . . . . . . . . .  . . . . . . . . . .  . . . . . . . . . .         1300
HPBDG64R.gcg           . . . . . . . . . .  . . . . . . . . . .  . . . . . . . . . .  . . . . . . . . . .  . . . . . . . . . .
HPBCR79R.gcg           . . . . . . . . . .  . . . . . . . . . .  . . . . . . . . . .  . . . . . . . . . .  . . . . . . . . . .
HSDFB55S01X.gcg        TTCTATTCAT           GGGACGAGTC           ATGCATCCTG           AAACAATGAA           CACAAGTGGA HPBCT06R.gcg     1301  . . . . . . . . . .  . . . . . . . . . .  . . . . . . . . . .  . . . . . . . . . .  . . . . . . . . . .         1350
HPBDG64R.gcg           . . . . . . . . . .  . . . . . . . . . .  . . . . . . . . . .  . . . . . . . . . .  . . . . . . . . . .
HPBCR79R.gcg           . . . . . . . . . .  . . . . . . . . . .  . . . . . . . . . .  . . . . . . . . . .  . . . . . . . . . .
HSDFB55S01X.gcg        CATGATTTCG           AAGAACTTTA           AGTTACTTTA           TTTGAATAAC           AAGGAAAACA HPBCT06R.gcg     1351  . . . . . . . . . .  . . . . . . . . . .  . . . . . . . . . .  . . . . . . . . . .  . . . . . . . . . .         1400
HPBDG64R.gcg           . . . . . . . . . .  . . . . . . . . . .  . . . . . . . . . .  . . . . . . . . . .  . . . . . . . . . .
HPBCR79R.gcg           . . . . . . . . . .  . . . . . . . . . .  . . . . . . . . . .  . . . . . . . . . .  . . . . . . . . . .
HSDFB55S01X.gcg        GTAACTAAGC           ACATTATGTT           TGCAACTGGT           ATATATTTAG           GATTTGTGTT HPBCT06R.gcg     1401  . . . . . . . . . .  . . . . . . . . . .  . . . . . . . . . .  . . . . . . . . . .  . . . . . . . . . .         1450
HPBDG64R.gcg           . . . . . . . . . .  . . . . . . . . . .  . . . . . . . . . .  . . . . . . . . . .  . . . . . . . . . .
HPBCR79R.gcg           . . . . . . . . . .  . . . . . . . . . .  . . . . . . . . . .  . . . . . . . . . .  . . . . . . . . . .
HSDFB55S01X.gcg        TTACAGTATA           TCTTAAGATA           ATATTTAAAA           TAGTTCCAGA           TAAAAACAAT HPBCT06R.gcg     2451  . . . . . . . . . .  . . . . . . . . . .  . . . . . . . . . .  . . . . . . . . . .  . . . . . . . . . .         1500
HPBDG64R.gcg           . . . . . . . . . .  . . . . . . . . . .  . . . . . . . . . .  . . . . . . . . . .  . . . . . . . . . .
HPBCR79R.gcg           . . . . . . . . . .  . . . . . . . . . .  . . . . . . . . . .  . . . . . . . . . .  . . . . . . . . . .
HSDFB55S01X.gcg        ATATGTAAAT           TATAAGTAAC           TTGTCAAGGA           ATGTTATCAG           TATTAAGCTA
```

FIG. 4F

```
                                                       1501                                                      1550
HPBCT06R.gcg      ..........  ..........  ..........  ..........  ..........  ..........  ..........  ..........  ..........  ..........
HPBDG64R.gcg      ..........  ..........  ..........  ..........  ..........  ..........  ..........  ..........  ..........  ..........
HPBCR79R.gcg      ..........  ..........  ..........  ..........  ..........  ..........  ..........  ..........  ..........  ..........
HSDFB55S01X.gcg   ATGGTCCTGT  TATGTCATTG  TGTTTGTGTG  CTGTTGTTTA  AAATAAAGT 551         1564
HPBCT06R.gcg      ..........  ....
HPBDG64R.gcg      ..........  ....
HPBCR79R.gcg      ..........  ....
HSDFB55S01X.gcg   ACCTATTGAA  CATG
```

FIG. 4G

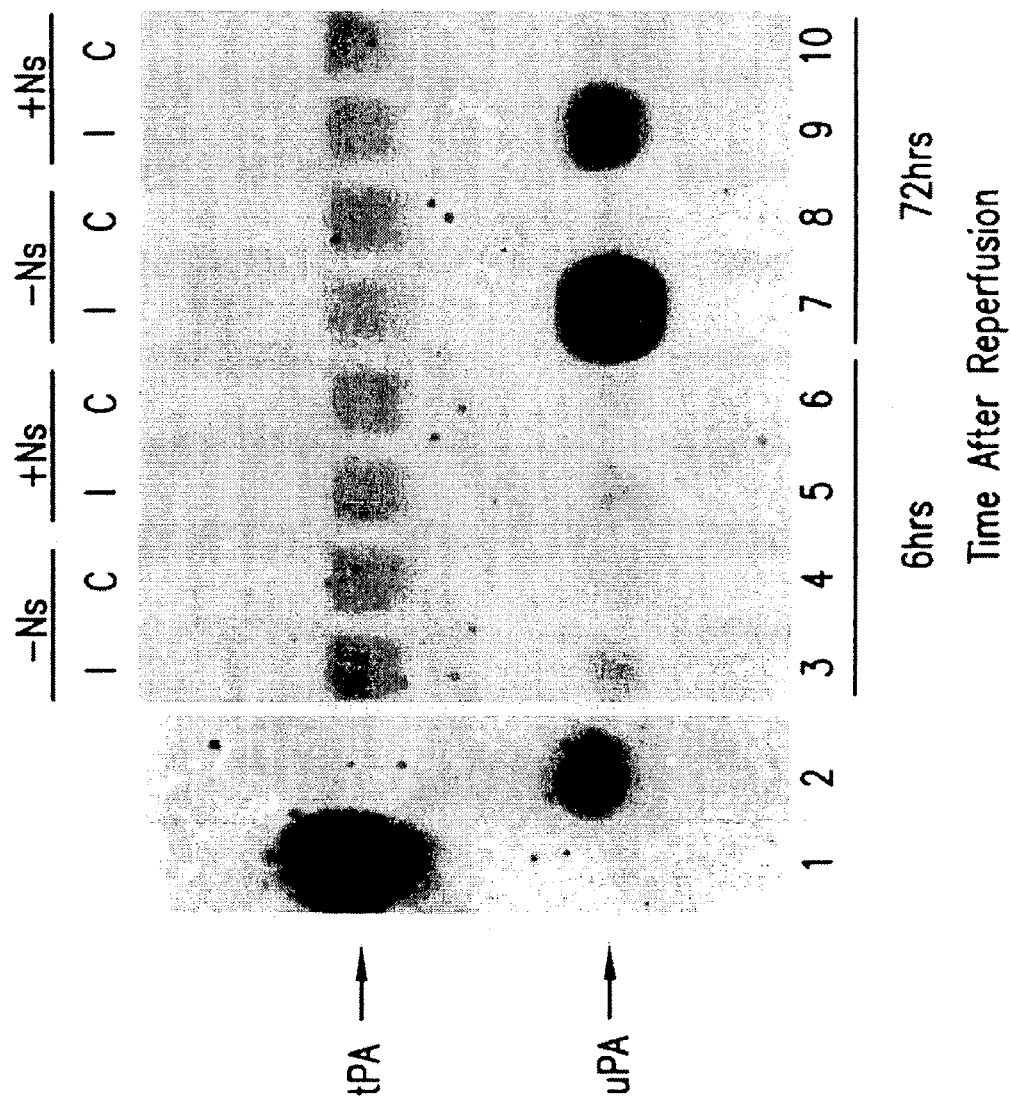

SEQUENCE LISTING

<160> NUMBER OF SEQ ID NOS: 21

<210> SEQ ID NO 1
<211> LENGTH: 1564
<212> TYPE: DNA
<213> ORGANISM: Homo sapiens
<220> FEATURE:
<221> NAME/KEY: CDS
<222> LOCATION: (89)..(1318)

<400> SEQUENCE: 1

```
gagcggagcg gagcacagtc cgccgagcac aagctccagc atcccgtcag gggttgcagg        60
tgtgtgggag gcttgaaact gttacaat atg gct ttc ctt gga ctc ttc tct         112
                              Met Ala Phe Leu Gly Leu Phe Ser
                                1               5 ttg ctg gtt ctg caa agt atg gct aca ggg gcc act ttc cct gag gaa         160
Leu Leu Val Leu Gln Ser Met Ala Thr Gly Ala Thr Phe Pro Glu Glu
         10                  15                  20 gcc att gct gac ttg tca gtg aat atg tat aat cgt ctt aga gcc act         208
Ala Ile Ala Asp Leu Ser Val Asn Met Tyr Asn Arg Leu Arg Ala Thr
 25                  30                  35                  40 ggt gaa gat gaa aat att ctc ttc tct cca ttg agt att gct ctt gca         256
Gly Glu Asp Glu Asn Ile Leu Phe Ser Pro Leu Ser Ile Ala Leu Ala
                 45                  50                  55 atg gga atg atg gaa ctt ggg gcc caa gga tct acc cag aaa gaa atc         304
Met Gly Met Met Glu Leu Gly Ala Gln Gly Ser Thr Gln Lys Glu Ile
             60                  65                  70 cgc cac tca atg gga tat gac agc cta aaa aat ggt gaa gaa ttt tct         352
Arg His Ser Met Gly Tyr Asp Ser Leu Lys Asn Gly Glu Glu Phe Ser
         75                  80                  85 ttc ttg aag gag ttt tca aac atg gta act gct aaa gag agc caa tat         400
Phe Leu Lys Glu Phe Ser Asn Met Val Thr Ala Lys Glu Ser Gln Tyr
 90                  95                 100 gtg atg aaa att gcc aat tcc ttg ttt gtg caa aat gga ttt cat gtc         448
Val Met Lys Ile Ala Asn Ser Leu Phe Val Gln Asn Gly Phe His Val
105                 110                 115                 120 aat gag gag ttt ttg caa atg atg aaa aaa tat ttt aat gca gca gta         496
Asn Glu Glu Phe Leu Gln Met Met Lys Lys Tyr Phe Asn Ala Ala Val
                125                 130                 135 aat cat gtg gac ttc agt caa aat gta gcc gtg gcc aac tac atc aat         544
Asn His Val Asp Phe Ser Gln Asn Val Ala Val Ala Asn Tyr Ile Asn
            140                 145                 150 aag tgg gtg gag aat aac aca aac aat ctg gtg aaa gat ttg gta tcc         592
Lys Trp Val Glu Asn Asn Thr Asn Asn Leu Val Lys Asp Leu Val Ser
        155                 160                 165 cca agg gat ttt gat gct gcc act tat ctg gcc ctc att aat gct gtc         640
Pro Arg Asp Phe Asp Ala Ala Thr Tyr Leu Ala Leu Ile Asn Ala Val
    170                 175                 180 tat ttc aag ggg aac tgg aag tcg cag ttt agg cct gaa aat act aga         688
Tyr Phe Lys Gly Asn Trp Lys Ser Gln Phe Arg Pro Glu Asn Thr Arg
185                 190                 195                 200 acc ttt tct ttc act aaa gat gat gaa agt gaa gtc caa att cca atg         736
Thr Phe Ser Phe Thr Lys Asp Asp Glu Ser Glu Val Gln Ile Pro Met
                205                 210                 215 atg tat cag caa gga gaa ttt tat tat ggg gaa ttt agt gat ggc tcc         784
Met Tyr Gln Gln Gly Glu Phe Tyr Tyr Gly Glu Phe Ser Asp Gly Ser
            220                 225                 230 aat gaa gct ggt ggt atc tac caa gtc cta gaa ata cca tat gaa gga         832
Asn Glu Ala Gly Gly Ile Tyr Gln Val Leu Glu Ile Pro Tyr Glu Gly
```

```
                235                 240                 245
gat gaa ata agc atg atg ctg gtg ctg tcc aga cag gaa gtt cct ctt      880
Asp Glu Ile Ser Met Met Leu Val Leu Ser Arg Gln Glu Val Pro Leu
    250                 255                 260 gct act ctg gag cca tta gtc aaa gca cag ctg gtt gaa gaa tgg gca      928
Ala Thr Leu Glu Pro Leu Val Lys Ala Gln Leu Val Glu Glu Trp Ala
265                 270                 275                 280 aac tct gtg aag aag caa aaa gta gaa gta tac ctg ccc agg ttc aca      976
Asn Ser Val Lys Lys Gln Lys Val Glu Val Tyr Leu Pro Arg Phe Thr
                285                 290                 295 gtg gaa cag gaa att gat tta aaa gat gtt ttg aag gct ctt gga ata     1024
Val Glu Gln Glu Ile Asp Leu Lys Asp Val Leu Lys Ala Leu Gly Ile
            300                 305                 310 act gaa att ttc atc aaa gat gca aat ttg aca ggc ctc tct gat aat     1072
Thr Glu Ile Phe Ile Lys Asp Ala Asn Leu Thr Gly Leu Ser Asp Asn
        315                 320                 325 aag gag att ttt ctt tcc aaa gca att cac aag tcc ttc cta gag gtt     1120
Lys Glu Ile Phe Leu Ser Lys Ala Ile His Lys Ser Phe Leu Glu Val
    330                 335                 340 aat gaa gaa ggc tca gaa gct gct gct gtc tca gga atg att gca att     1168
Asn Glu Glu Gly Ser Glu Ala Ala Ala Val Ser Gly Met Ile Ala Ile
345                 350                 355                 360 agt agg atg gct gtg ctg tat cct caa gtt att gtc gac cat cca ttt     1216
Ser Arg Met Ala Val Leu Tyr Pro Gln Val Ile Val Asp His Pro Phe
                365                 370                 375 ttc ttt ctt atc aga aac agg aga act ggt aca att cta ttc atg gga     1264
Phe Phe Leu Ile Arg Asn Arg Arg Thr Gly Thr Ile Leu Phe Met Gly
            380                 385                 390 cga gtc atg cat cct gaa aca atg aac aca agt gga cat gat ttc gaa     1312
Arg Val Met His Pro Glu Thr Met Asn Thr Ser Gly His Asp Phe Glu
        395                 400                 405 gaa ctt taagttactt tatttgaata acaaggaaaa cagtaactaa gcacattatg      1368
Glu Leu
    410 tttgcaactg gtatatattt aggatttgtg ttttacagta tatcttaaga taatatttaa   1428 aatagttcca gataaaaaca atatatgtaa attataagta acttgtcaag gaatgttatc   1488 agtattaagc taatggtcct gttatgtcat tgtgtttgtg tgctgttgtt taaaataaaa   1548 gtacctattg aacatg                                                  1564

<210> SEQ ID NO 2
<211> LENGTH: 410
<212> TYPE: PRT
<213> ORGANISM: Homo sapiens

<400> SEQUENCE: 2

Met Ala Phe Leu Gly Leu Phe Ser Leu Leu Val Leu Gln Ser Met Ala
1               5                   10                  15

Thr Gly Ala Thr Phe Pro Glu Glu Ala Ile Ala Asp Leu Ser Val Asn
            20                  25                  30

Met Tyr Asn Arg Leu Arg Ala Thr Gly Glu Asp Glu Asn Ile Leu Phe
        35                  40                  45

Ser Pro Leu Ser Ile Ala Leu Ala Met Gly Met Met Glu Leu Gly Ala
    50                  55                  60

Gln Gly Ser Thr Gln Lys Glu Ile Arg His Ser Met Gly Tyr Asp Ser
65                  70                  75                  80

Leu Lys Asn Gly Glu Glu Phe Ser Phe Leu Lys Glu Phe Ser Asn Met
            85                  90                  95
```

```
Val Thr Ala Lys Glu Ser Gln Tyr Val Met Lys Ile Ala Asn Ser Leu
            100                 105                 110

Phe Val Gln Asn Gly Phe His Val Asn Glu Glu Phe Leu Gln Met Met
            115                 120                 125

Lys Lys Tyr Phe Asn Ala Ala Val Asn His Val Asp Phe Ser Gln Asn
            130                 135                 140

Val Ala Val Ala Asn Tyr Ile Asn Lys Trp Val Glu Asn Asn Thr Asn
145                 150                 155                 160

Asn Leu Val Lys Asp Leu Val Ser Pro Arg Asp Phe Asp Ala Ala Thr
                165                 170                 175

Tyr Leu Ala Leu Ile Asn Ala Val Tyr Phe Lys Gly Asn Trp Lys Ser
            180                 185                 190

Gln Phe Arg Pro Glu Asn Thr Arg Thr Phe Ser Phe Thr Lys Asp Asp
            195                 200                 205

Glu Ser Glu Val Gln Ile Pro Met Met Tyr Gln Gln Gly Glu Phe Tyr
210                 215                 220

Tyr Gly Glu Phe Ser Asp Gly Ser Asn Glu Ala Gly Gly Ile Tyr Gln
225                 230                 235                 240

Val Leu Glu Ile Pro Tyr Glu Gly Asp Glu Ile Ser Met Met Leu Val
                245                 250                 255

Leu Ser Arg Gln Glu Val Pro Leu Ala Thr Leu Glu Pro Leu Val Lys
            260                 265                 270

Ala Gln Leu Val Glu Glu Trp Ala Asn Ser Val Lys Lys Gln Lys Val
            275                 280                 285

Glu Val Tyr Leu Pro Arg Phe Thr Val Glu Gln Glu Ile Asp Leu Lys
            290                 295                 300

Asp Val Leu Lys Ala Leu Gly Ile Thr Glu Ile Phe Ile Lys Asp Ala
305                 310                 315                 320

Asn Leu Thr Gly Leu Ser Asp Asn Lys Glu Ile Phe Leu Ser Lys Ala
                325                 330                 335

Ile His Lys Ser Phe Leu Glu Val Asn Glu Glu Gly Ser Glu Ala Ala
            340                 345                 350

Ala Val Ser Gly Met Ile Ala Ile Ser Arg Met Ala Val Leu Tyr Pro
            355                 360                 365

Gln Val Ile Val Asp His Pro Phe Phe Phe Leu Ile Arg Asn Arg Arg
            370                 375                 380

Thr Gly Thr Ile Leu Phe Met Gly Arg Val Met His Pro Glu Thr Met
385                 390                 395                 400

Asn Thr Ser Gly His Asp Phe Glu Glu Leu
                405                 410

<210> SEQ ID NO 3
<211> LENGTH: 410
<212> TYPE: PRT
<213> ORGANISM: Gallus gallus

<400> SEQUENCE: 3

Met Tyr Phe Leu Gly Leu Leu Ser Leu Leu Val Leu Pro Ser Lys Ala
1               5                   10                  15

Phe Lys Thr Asn Phe Pro Asp Glu Thr Ile Ala Glu Leu Ser Val Asn
            20                  25                  30

Val Tyr Asn Gln Leu Arg Ala Ala Arg Glu Asp Glu Asn Ile Leu Phe
        35                  40                  45

Cys Pro Leu Ser Ile Ala Ile Ala Met Gly Met Ile Glu Leu Gly Ala
```

-continued

```
                 50                  55                  60
His Gly Thr Thr Leu Lys Glu Ile Arg His Ser Leu Gly Phe Asp Ser
 65                  70                  75                  80
Leu Lys Asn Gly Glu Glu Phe Thr Phe Leu Lys Asp Leu Ser Asp Met
                 85                  90                  95
Ala Thr Thr Glu Glu Ser His Tyr Val Leu Asn Met Ala Asn Ser Leu
                100                 105                 110
Tyr Val Gln Asn Gly Phe His Val Ser Glu Lys Phe Leu Gln Leu Val
                115                 120                 125
Lys Lys Tyr Phe Lys Ala Glu Val Glu Asn Ile Asp Phe Ser Gln Ser
130                 135                 140
Ala Ala Val Ala Thr His Ile Asn Lys Trp Val Glu Asn His Thr Asn
145                 150                 155                 160
Asn Met Ile Lys Asp Phe Val Ser Ser Arg Asp Phe Ser Ala Leu Thr
                165                 170                 175
His Leu Val Leu Ile Asn Ala Ile Tyr Phe Lys Gly Asn Trp Lys Ser
                180                 185                 190
Gln Phe Arg Pro Glu Asn Thr Arg Thr Phe Ser Phe Thr Lys Asp Asp
                195                 200                 205
Glu Thr Glu Val Gln Ile Pro Met Met Tyr Gln Gln Gly Glu Phe Tyr
210                 215                 220
Tyr Gly Glu Phe Ser Asp Gly Ser Asn Glu Ala Gly Gly Ile Tyr Gln
225                 230                 235                 240
Val Leu Glu Ile Pro Tyr Glu Gly Asp Glu Ile Ser Met Met Ile Val
                245                 250                 255
Leu Ser Arg Gln Glu Val Pro Leu Val Thr Leu Glu Pro Leu Val Lys
                260                 265                 270
Ala Ser Leu Ile Asn Glu Trp Ala Asn Ser Val Lys Lys Gln Lys Val
                275                 280                 285
Glu Val Tyr Leu Pro Arg Phe Thr Val Glu Gln Glu Ile Asp Leu Lys
                290                 295                 300
Asp Val Leu Lys Gly Leu Gly Ile Thr Glu Val Phe Ser Arg Ser Ala
305                 310                 315                 320
Asp Leu Thr Ala Met Ser Asp Asn Lys Glu Leu Tyr Leu Ala Lys Ala
                325                 330                 335
Phe His Lys Ala Phe Leu Glu Val Asn Glu Glu Gly Ser Glu Ala Ala
                340                 345                 350
Ala Ala Ser Gly Met Ile Ala Ile Ser Arg Met Ala Val Leu Tyr Pro
                355                 360                 365
Gln Val Ile Val Asp His Pro Phe Phe Phe Leu Val Arg Asn Arg Arg
                370                 375                 380
Thr Gly Thr Val Leu Phe Met Gly Arg Val Met His Pro Glu Ala Met
385                 390                 395                 400
Asn Thr Ser Gly His Asp Phe Glu Glu Leu
                405                 410

<210> SEQ ID NO 4
<211> LENGTH: 402
<212> TYPE: PRT
<213> ORGANISM: Bos taurus

<400> SEQUENCE: 4

Met Arg Met Ser Pro Val Phe Ala Cys Leu Ala Leu Gly Leu Ala Leu
 1               5                  10                  15
```

```
Ile Phe Gly Glu Gly Ser Ala Ser Tyr Gln Pro Gln Ser Ala Ala Ala
             20                  25                  30

Ser Leu Ala Thr Asp Phe Gly Val Lys Val Phe Gln Gln Val Val Arg
         35                  40                  45

Ala Ser Lys Asp Arg Asn Val Val Phe Ser Pro Tyr Gly Val Ala Ser
     50                  55                  60

Val Leu Ala Met Leu Gln Leu Thr Thr Gly Gly Glu Thr Arg Gln Gln
 65                  70                  75                  80

Ile Gln Glu Ala Met Gln Phe Lys Ile Glu Glu Lys Gly Met Ala Pro
                 85                  90                  95

Ala Phe His Arg Leu Tyr Lys Glu Leu Met Gly Pro Trp Asn Lys Asp
             100                 105                 110

Glu Ile Ser Thr Ala Asp Ala Ile Phe Val Gln Arg Asp Leu Glu Leu
         115                 120                 125

Val His Gly Phe Met Pro Asn Phe Phe Arg Leu Phe Arg Thr Thr Val
     130                 135                 140

Lys Gln Val Asp Phe Ser Glu Val Glu Arg Ala Arg Phe Ile Val Asn
145                 150                 155                 160

Asp Trp Val Lys Arg His Thr Lys Gly Met Ile Ser Asp Leu Leu Gly
                 165                 170                 175

Glu Gly Ala Val Asp Gln Leu Thr Arg Leu Val Leu Val Asn Ala Leu
             180                 185                 190

Tyr Phe Asn Gly Gln Trp Lys Met Pro Phe Pro Glu Ser Asn Thr His
         195                 200                 205

His Arg Leu Phe His Lys Ser Asp Gly Ser Thr Ile Ser Val Pro Met
     210                 215                 220

Met Ala Gln Thr Asn Lys Phe Asn Tyr Thr Glu Phe Thr Thr Pro Asp
225                 230                 235                 240

Gly Arg Tyr Tyr Asp Ile Leu Glu Leu Pro Tyr His Gly Asn Thr Leu
                 245                 250                 255

Ser Met Leu Ile Ala Ala Pro Tyr Glu Lys Glu Val Pro Leu Ser Ala
             260                 265                 270

Leu Thr Ser Ile Leu Asp Ala Glu Leu Ile Ser Gln Trp Lys Gly Asn
         275                 280                 285

Met Thr Arg Leu Thr Arg Leu Leu Val Leu Pro Lys Phe Ser Leu Glu
     290                 295                 300

Thr Glu Ile Asp Leu Arg Arg Pro Leu Glu Asn Leu Gly Met Thr Asp
305                 310                 315                 320

Met Phe Arg Pro Ser Gln Ala Asp Phe Ser Ser Phe Ser Asp Gln Glu
                 325                 330                 335

Phe Leu Tyr Val Ser Gln Ala Leu Gln Lys Val Lys Ile Glu Val Asn
             340                 345                 350

Glu Ser Gly Thr Leu Ala Ser Ser Thr Ala Leu Val Val Ser Ala
         355                 360                 365

Arg Met Ala Pro Glu Glu Ile Ile Met Asp Arg Pro Phe Leu Phe Val
     370                 375                 380

Val Arg His Asn Pro Thr Gly Thr Val Leu Phe Met Gly Gln Val Met
385                 390                 395                 400

Glu Pro

<210> SEQ ID NO 5
<211> LENGTH: 397
<212> TYPE: PRT
<213> ORGANISM: Rattus norvegicus
```

```
<400> SEQUENCE: 5

Met Asn Trp His Phe Pro Phe Phe Ile Leu Thr Thr Val Thr Leu Ser
1               5                   10                  15

Ser Val Tyr Ser Gln Leu Asn Ser Leu Ser Leu Glu Glu Leu Gly Ser
            20                  25                  30

Asp Thr Gly Ile Gln Val Phe Asn Gln Ile Ile Lys Ser Gln Pro His
            35                  40                  45

Glu Asn Val Val Ile Ser Pro His Gly Ile Ala Ser Ile Leu Gly Met
50                  55                  60

Leu Gln Leu Gly Ala Asp Gly Arg Thr Lys Lys Gln Leu Ser Thr Val
65                  70                  75                  80

Met Arg Tyr Asn Val Asn Gly Val Gly Lys Val Leu Lys Lys Ile Asn
                85                  90                  95

Lys Ala Ile Val Ser Lys Lys Asn Lys Asp Ile Val Thr Val Ala Asn
            100                 105                 110

Ala Val Phe Val Arg Asn Gly Phe Lys Val Glu Val Pro Phe Ala Ala
            115                 120                 125

Arg Asn Lys Glu Val Phe Gln Cys Glu Val Gln Ser Val Asn Phe Gln
        130                 135                 140

Asp Pro Ala Ser Ala Cys Asp Ala Ile Asn Phe Trp Val Lys Asn Glu
145                 150                 155                 160

Thr Arg Gly Met Ile Asp Asn Leu Leu Ser Pro Asn Leu Ile Asp Ser
                165                 170                 175

Ala Leu Thr Lys Leu Val Leu Val Asn Ala Val Tyr Phe Lys Gly Leu
            180                 185                 190

Trp Lys Ser Arg Phe Gln Pro Glu Asn Thr Lys Lys Arg Thr Phe Val
        195                 200                 205

Ala Gly Asp Gly Lys Ser Tyr Gln Val Pro Met Leu Ala Gln Leu Ser
210                 215                 220

Val Phe Arg Ser Gly Ser Thr Lys Thr Pro Asn Gly Leu Trp Tyr Asn
225                 230                 235                 240

Phe Ile Glu Leu Pro Tyr His Gly Glu Ser Ile Ser Met Leu Ile Ala
                245                 250                 255

Leu Pro Thr Glu Ser Ser Thr Pro Leu Ser Ala Ile Ile Pro His Ile
            260                 265                 270

Ser Thr Lys Thr Ile Asn Ser Trp Met Asn Thr Met Val Pro Lys Arg
        275                 280                 285

Met Gln Leu Val Leu Pro Lys Phe Thr Ala Leu Ala Gln Thr Asp Leu
290                 295                 300

Lys Glu Pro Leu Lys Ala Leu Gly Ile Thr Glu Met Phe Glu Pro Ser
305                 310                 315                 320

Lys Ala Asn Phe Ala Lys Ile Thr Arg Ser Glu Ser Leu His Val Ser
                325                 330                 335

His Ile Leu Gln Lys Ala Lys Ile Glu Val Ser Glu Asp Gly Thr Lys
            340                 345                 350

Ala Ala Val Val Thr Thr Ala Ile Leu Ile Ala Arg Ser Ser Pro Pro
        355                 360                 365

Trp Phe Ile Val Asp Arg Pro Phe Leu Phe Cys Ile Arg His Asn Pro
370                 375                 380

Thr Gly Ala Ile Leu Phe Leu Gly Gln Val Asn Lys Pro
385                 390                 395
```

```
<210> SEQ ID NO 6
<211> LENGTH: 465
<212> TYPE: PRT
<213> ORGANISM: Mus musculus

<400> SEQUENCE: 6
```

| | | | | | | | | | | | | | | | |
|---|---|---|---|---|---|---|---|---|---|---|---|---|---|---|---|
| Met | Tyr | Ser | Pro | Gly | Ala | Gly | Ser | Gly | Ala | Ala | Gly | Glu | Arg | Lys | Leu |
| 1 | | | | 5 | | | | | 10 | | | | | 15 | |
| Cys | Leu | Leu | Ser | Leu | Leu | Leu | Ile | Gly | Ala | Leu | Gly | Cys | Ala | Ile | Cys |
| | | | 20 | | | | | 25 | | | | | 30 | | |
| His | Gly | Asn | Pro | Val | Asp | Asp | Ile | Cys | Ile | Ala | Lys | Pro | Arg | Asp | Ile |
| | | | 35 | | | | | 40 | | | | | 45 | | |
| Pro | Val | Asn | Pro | Leu | Cys | Ile | Tyr | Arg | Ser | Pro | Gly | Lys | Lys | Ala | Thr |
| | 50 | | | | | 55 | | | | | 60 | | | | |
| Glu | Glu | Asp | Gly | Ser | Glu | Gln | Lys | Val | Pro | Glu | Ala | Thr | Asn | Arg | Arg |
| 65 | | | | | 70 | | | | | 75 | | | | | 80 |
| Val | Trp | Glu | Leu | Ser | Lys | Ala | Asn | Ser | Arg | Phe | Ala | Thr | Asn | Phe | Tyr |
| | | | | 85 | | | | | 90 | | | | | 95 | |
| Gln | His | Leu | Ala | Asp | Ser | Lys | Asn | Asp | Asn | Asp | Ile | Phe | Leu | Ser | |
| | | | 100 | | | | | 105 | | | | | 110 | | |
| Pro | Leu | Ser | Ile | Ser | Thr | Ala | Phe | Ala | Met | Thr | Lys | Leu | Gly | Ala | Cys |
| | | | 115 | | | | | 120 | | | | | 125 | | |
| Asn | Asp | Thr | Leu | Lys | Gln | Leu | Met | Glu | Val | Phe | Lys | Phe | Asp | Thr | Ile |
| | 130 | | | | | 135 | | | | | 140 | | | | |
| Ser | Glu | Lys | Thr | Ser | Asp | Gln | Ile | His | Phe | Phe | Ala | Lys | Leu | Asn | |
| 145 | | | | | 150 | | | | | 155 | | | | | 160 |
| Cys | Arg | Leu | Tyr | Arg | Lys | Ala | Asn | Lys | Ser | Ser | Asp | Leu | Val | Ser | Ala |
| | | | | 165 | | | | | 170 | | | | | 175 | |
| Asn | Arg | Leu | Phe | Gly | Asp | Lys | Ser | Leu | Thr | Phe | Asn | Glu | Ser | Tyr | Gln |
| | | | 180 | | | | | 185 | | | | | 190 | | |
| Asp | Val | Ser | Glu | Val | Val | Tyr | Gly | Ala | Lys | Leu | Gln | Pro | Leu | Asp | Phe |
| | | | 195 | | | | | 200 | | | | | 205 | | |
| Lys | Glu | Asn | Pro | Glu | Gln | Ser | Arg | Val | Thr | Ile | Asn | Asn | Trp | Val | Ala |
| | 210 | | | | | 215 | | | | | 220 | | | | |
| Asn | Lys | Thr | Glu | Gly | Arg | Ile | Lys | Asp | Val | Ile | Pro | Gln | Gly | Ala | Ile |
| 225 | | | | | 230 | | | | | 235 | | | | | 240 |
| Asn | Glu | Leu | Thr | Ala | Leu | Val | Leu | Val | Asn | Thr | Ile | Tyr | Phe | Lys | Gly |
| | | | | 245 | | | | | 250 | | | | | 255 | |
| Leu | Trp | Lys | Ser | Lys | Phe | Ser | Pro | Glu | Asn | Thr | Arg | Lys | Glu | Pro | Phe |
| | | | 260 | | | | | 265 | | | | | 270 | | |
| Tyr | Lys | Val | Asp | Gly | Gln | Ser | Cys | Pro | Val | Pro | Met | Met | Tyr | Gln | Glu |
| | | | 275 | | | | | 280 | | | | | 285 | | |
| Gly | Lys | Phe | Lys | Tyr | Arg | Arg | Val | Ala | Glu | Gly | Thr | Gln | Val | Leu | Glu |
| | 290 | | | | | 295 | | | | | 300 | | | | |
| Leu | Pro | Phe | Lys | Gly | Asp | Asp | Ile | Thr | Met | Val | Leu | Ile | Leu | Pro | Lys |
| 305 | | | | | 310 | | | | | 315 | | | | | 320 |
| Pro | Glu | Lys | Ser | Leu | Ala | Lys | Val | Glu | Gln | Glu | Leu | Thr | Pro | Glu | Leu |
| | | | | 325 | | | | | 330 | | | | | 335 | |
| Leu | Gln | Glu | Trp | Leu | Asp | Glu | Leu | Ser | Glu | Thr | Met | Leu | Val | Val | His |
| | | | 340 | | | | | 345 | | | | | 350 | | |
| Met | Pro | Arg | Phe | Arg | Thr | Glu | Asp | Gly | Phe | Ser | Leu | Lys | Glu | Gln | Leu |
| | | | 355 | | | | | 360 | | | | | 365 | | |
| Gln | Asp | Met | Gly | Leu | Ile | Asp | Leu | Phe | Ser | Pro | Glu | Lys | Ser | Gln | Leu |
| | 370 | | | | | 375 | | | | | 380 | | | | |

```
Pro Gly Ile Val Ala Gly Gly Arg Asp Asp Leu Tyr Val Ser Asp Ala
385                 390                 395                 400

Phe His Lys Ala Phe Leu Glu Val Asn Glu Glu Gly Ser Glu Ala Ala
                405                 410                 415

Ala Ser Thr Ser Val Val Ile Thr Gly Arg Ser Leu Asn Pro Asn Arg
            420                 425                 430

Val Thr Phe Lys Ala Asn Arg Pro Phe Leu Val Leu Ile Arg Glu Val
        435                 440                 445

Ala Leu Asn Thr Ile Ile Phe Met Gly Arg Val Ala Asn Pro Cys Val
    450                 455                 460

Asn
465

<210> SEQ ID NO 7
<211> LENGTH: 354
<212> TYPE: DNA
<213> ORGANISM: Homo sapiens
<220> FEATURE:
<221> NAME/KEY: misc_feature
<222> LOCATION: (323)
<223> OTHER INFORMATION: n equals a, t, g, or c

<400> SEQUENCE: 7
ggaagttcct cttgctactc tggagccatt agtcaaagca cagctggttg aagaatgggc    60
aaactctgtg aagaagcaaa aagtagaagt atacctgccc aggttcacag tggaacagga   120
aattgattta aaagatgttt tgaaggctct tggaataact gaaattttca tcaaagatgc   180
aaatttgaca ggcctctctg ataataagga gatttttctt tccaaagcaa ttcacaagtc   240
cttcctagag gttaaatgaa ggaaggctcc agaagctgct gctggtcttc aggaatgatt   300
tgcaattagt agggttggct gtnctgtatc cctcaaggtt attgtcggcc atcc         354

<210> SEQ ID NO 8
<211> LENGTH: 352
<212> TYPE: DNA
<213> ORGANISM: Homo sapiens
<220> FEATURE:
<221> NAME/KEY: misc_feature
<222> LOCATION: (60)
<223> OTHER INFORMATION: n equals a, t, g, or c
<220> FEATURE:
<221> NAME/KEY: misc_feature
<222> LOCATION: (75)
<223> OTHER INFORMATION: n equals a, t, g, or c
<220> FEATURE:
<221> NAME/KEY: misc_feature
<222> LOCATION: (130)
<223> OTHER INFORMATION: n equals a, t, g, or c
<220> FEATURE:
<221> NAME/KEY: misc_feature
<222> LOCATION: (223)
<223> OTHER INFORMATION: n equals a, t, g, or c
<220> FEATURE:
<221> NAME/KEY: misc_feature
<222> LOCATION: (263)
<223> OTHER INFORMATION: n equals a, t, g, or c
<220> FEATURE:
<221> NAME/KEY: misc_feature
<222> LOCATION: (311)
<223> OTHER INFORMATION: n equals a, t, g, or c
<220> FEATURE:
<221> NAME/KEY: misc_feature
<222> LOCATION: (317)
<223> OTHER INFORMATION: n equals a, t, g, or c
<220> FEATURE:
<221> NAME/KEY: misc_feature
<222> LOCATION: (336)
<223> OTHER INFORMATION: n equals a, t, g, or c
```

```
<400> SEQUENCE: 8
agacaggaag ttcctcttgc tactctggag ccattagtca aagcacagct ggttgaagan      60
tgggcaaact ctgtnaagaa gcaaaaagta gaagtatacc tgcccaggtt cacagtggaa     120
caggaaattn atttaaaaga tgttttgaag gctcttggaa taactgaaat tttcatcaaa     180
gatgcaaatt tgacaggcct ctctgataat aaggagattt tcntttccaa agcaattcac     240
aagtccttcc tagaggttaa tgnaggaggc tccagaagct gctgctgtct cagggatgat     300
ttgcaattta ngtaggntgg gctgtgctgg tatccncaag gttatttttc gg             352

<210> SEQ ID NO 9
<211> LENGTH: 399
<212> TYPE: DNA
<213> ORGANISM: Homo sapiens

<400> SEQUENCE: 9
ggaagttcct cttgctactc tggagccatt agtcaaagca cagctggttg aagaatgggc      60
aaactctgtg aagaagcaaa aagtagaagt atacctgccc aggttcacag tggaacagga    120
aattgattta aaagatgttt tgaaggctct tggaataact gaaattttca tcaaagatgc    180
aaatttgaca ggcctctctg ataataagga gattttcttt ccaaagcaa ttcacaagtc      240 cttcctagag gttaatgaag aaggctcaga agctgctgct gtctcagga atgattgcaa     300 ttagtaggat ggctgtgctg tatcctcaag gttattgtcg accatccatt tttcctttct    360
tatcagaacc aggggacctg gtacaattct attcatggg                             399

<210> SEQ ID NO 10
<211> LENGTH: 30
<212> TYPE: DNA
<213> ORGANISM: Artificial Sequence
<220> FEATURE:
<221> NAME/KEY: primer_bind
<223> OTHER INFORMATION: This 5' primer sequence has a BamH1 restriction
      site (GGATCC) followed by nucleotides encoding an amino terminal
      portion of mature human BAIT BAIT (Brain-Associated Inhibitor of
      Tissue-Type Plasminogen Activator).

<400> SEQUENCE: 10
gagcatggat ccgccacttt ccctgaggaa                                        30

<210> SEQ ID NO 11
<211> LENGTH: 33
<212> TYPE: DNA
<213> ORGANISM: Artificial Sequence
<220> FEATURE:
<221> NAME/KEY: primer_bind
<223> OTHER INFORMATION: This 3' primer sequence has a BamH1 restriction
      site (GGATCC) and nucleotides complementary to the 3' end coding
      sequence of the human BAIT (Brain-Associated Inhibitor of
      Tissue-Type Plasminogen Activator) DNA sequence.

<400> SEQUENCE: 11
gcacatggat ccttaaagtt cttcgaaatc atg                                    33

<210> SEQ ID NO 12
<211> LENGTH: 36
<212> TYPE: DNA
<213> ORGANISM: Artificial Sequence
<220> FEATURE:
<221> NAME/KEY: primer_bind
<223> OTHER INFORMATION: This 5' primer sequence has a BamH1 restriction
      site (GGATCC), a sequence for initiation of translation in
      eukaryotic cells (see Kozak, M., J. Mol. Biol. 196:947-950
```

(1987)), followed by nucleotides encoding the amino terminus of
human BAIT.

<400> SEQUENCE: 12
gagcatggat ccgccatcat ggctttcctt ggactc                             36

<210> SEQ ID NO 13
<211> LENGTH: 30
<212> TYPE: DNA
<213> ORGANISM: Artificial Sequence
<220> FEATURE:
<221> NAME/KEY: primer_bind
<223> OTHER INFORMATION: This 3' primer sequence has an XbaI restriction
      site (TCTAGA) followed by nucleotides complementary to 3'
      noncoding sequence of the human BAIT (Brain-Associated Inhibitor
      of Tissue-Type Plasminogen Activator) DNA sequence.

<400> SEQUENCE: 13
gagcattcta gagttgcaaa cataatgtgc                                    30

<210> SEQ ID NO 14
<211> LENGTH: 36
<212> TYPE: DNA
<213> ORGANISM: Artificial Sequence
<220> FEATURE:
<221> NAME/KEY: primer_bind
<223> OTHER INFORMATION: This 5' primer sequence has a BamH1
      restriction site (GGATCC), a sequence for initiation of
      translation in eukaryotic cells (see Kozak, M., J. Mol. Biol.
      196:947-950 (1987)), followed by nucleotides encoding the amino
      terminus of human BAIT.

<400> SEQUENCE: 14
gagcatggat ccgccatcat ggctttcctt ggactc                             36

<210> SEQ ID NO 15
<211> LENGTH: 30
<212> TYPE: DNA
<213> ORGANISM: Artificial Sequence
<220> FEATURE:
<221> NAME/KEY: primer_bind
<223> OTHER INFORMATION: This 3' primer sequence has a BamH1 restriction
      site (GGATCC) followed by nucleotides complementary to 3'
      noncoding sequence of the human BAIT (Brain-Associated Inhibitor
      of Tissue-Type Plasminogen Activator) DNA sequence.

<400> SEQUENCE: 15
gcacatggat ccaagttctt cgaaatcatg                                    30

<210> SEQ ID NO 16
<211> LENGTH: 36
<212> TYPE: DNA
<213> ORGANISM: Artificial Sequence
<220> FEATURE:
<221> NAME/KEY: primer_bind
<223> OTHER INFORMATION: This 5' primer sequence has a BamH1 restriction
      site (GGATCC), a sequence for initiation of translation in
      eukaryotic cells (see Kozak, M., J. Mol. Biol. 196:947-950
      (1987)), followed by nucleotides encoding the amino terminus of
      human BAIT.

<400> SEQUENCE: 16
gagcatggat ccgccatcat ggctttcctt ggactc                             36

<210> SEQ ID NO 17
<211> LENGTH: 30
<212> TYPE: DNA
<213> ORGANISM: Artificial Sequence
<220> FEATURE:

-continued

<221> NAME/KEY: primer_bind
<223> OTHER INFORMATION: This 3' primer sequence has an XbaI restriction
      site (TCTAGA) followed by nucleotides complementary to 3'
      noncoding sequence of the human BAIT (Brain-Associated Inhibitor
      of Tissue-Type Plasminogen Activator) DNA sequence.

<400> SEQUENCE: 17
gagcattcta gagttgcaaa cataatgtgc                                      30

<210> SEQ ID NO 18
<211> LENGTH: 733
<212> TYPE: DNA
<213> ORGANISM: Homo sapiens

<400> SEQUENCE: 18
gggatccgga gcccaaatct tctgacaaaa ctcacacatg cccaccgtgc ccagcacctg     60
aattcgaggg tgcaccgtca gtcttcctct tcccccaaa  acccaaggac accctcatga    120
tctcccggac tcctgaggtc acatgcgtgg tggtggacgt aagccacgaa gaccctgagg    180
tcaagttcaa ctggtacgtg gacggcgtgg aggtgcataa tgccaagaca agccgcggg     240 aggagcagta caacagcacg taccgtgtgg tcagcgtcct caccgtcctg caccaggact    300
ggctgaatgg caaggagtac aagtgcaagg tctccaacaa agccctccca acccccatcg    360
agaaaaccat ctccaaagcc aaagggcagc ccgagaacc  acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                       733

<210> SEQ ID NO 19
<211> LENGTH: 5
<212> TYPE: PRT
<213> ORGANISM: Homo sapiens

<400> SEQUENCE: 19

Ala Thr Phe Pro Glu
1               5

<210> SEQ ID NO 20
<211> LENGTH: 5
<212> TYPE: PRT
<213> ORGANISM: Homo sapiens

<400> SEQUENCE: 20

Thr Phe Pro Glu Glu
1               5

<210> SEQ ID NO 21
<211> LENGTH: 5
<212> TYPE: PRT
<213> ORGANISM: Homo sapiens

<400> SEQUENCE: 21

Met Pro Glu Glu Ala
1               5

BRAIN ASSOCIATED INHIBITOR OF TISSUE-TYPE PLASMINOGEN ACTIVATOR

CROSS REFERENCE TO RELATED APPLICATIONS

This application is a divisional of U.S. application Ser. No. 09/957,485 (filed on Sep. 21, 2001), now abandoned which is a continuation of U.S. application Ser. No. 09/521,664, (filed on Mar. 8, 2000) now abandoned which claims benefit under 35 U.S.C. §119(e) of U.S. Provisional Application No. 60,123,704 (filed on Mar. 10, 1999). Each patent and patent application referenced above is hereby incorporated by reference herein in its entirety.

FIELD OF THE INVENTION

The present invention relates to a novel human gene encoding a polypeptide expressed in human brain tissue which is a member of the serine protease inhibitor ("serpin") superfamily and appears to be a human homolog of "neuroserpin," a serpin recently identified in the chicken. More specifically, isolated nucleic acid molecules are provided encoding a human polypeptide named Brain-Associated Inhibitor of Tissue-Type Plasminogen Activator, hereinafter referred to as "BAIT." BAIT polypeptides are also provided, as are vectors, host cells and recombinant methods for producing the same. The invention further relates to screening methods for identifying agonists and antagonists of BAIT activity. Also provided are diagnostic methods for detecting disorders related to the central and peripheral nervous system and the circulatory system, and therapeutic methods for treating such disorders.

BACKGROUND OF THE INVENTION

Localized proteolytic activity through the action of proteases plays a critical regulatory role in a variety of important biological processes. For instance, the enzyme plasmin plays such a role in hemostasis, angiogenesis, tumor metastisis, cellular migration and ovulation. Plasmin is generated from its precursor zymogen plasminogen by the action of plasminogen activators (PAs) such as tissue-type PA (t-PA) and urokinase-type (u-PA), both of which are serine proteases. The activity of the PA system is precisely regulated by several mechanisms, one of which involves the interaction of t-PA and u-PA with specific plasminogen activator inhibitors. Among these serine protease inhibitors (i.e., serpins), plasminogen activator inhibitor type I (PAI-1) is unique in its ability to efficiently inhibit u-PA as well as the single and two-chain forms of t-PA. High PAI-1 levels are associated with an increased risk of thromboembolic disease, while PAI-1 deficiency may represent an inherited autosomal recessive bleeding disorder. See, for instance, Reilly, T. M., et al., Recombinant plasminogen activator inhibitor type 1: a review of structural, functional, and biological aspects, *Blood Coag. And Fibrinolysis* 5:73–81 (1994).

Serpin Mechanism

The serpins are a gene family that encompasses a wide variety of protein products, including many of the proteinase inhibitors in plasma (Huber, R. (1989) Biochemistry, 28, 8951–8966). However, in spite of their name, not all serpins are proteinase inhibitors. They include steroid binding globulins, the prohormone angiotensinogen, the egg white protein ovalbumin, and barley protein Z, a major constituent of beer. The serpins are thought to share a common tertiary structure (Doolittle, R. F. (1983) Science, 222, 417–419) and to have evolved from a common ancestor (Hunt, L. T (1980) Biochemical and Biophysical Research Communications, 95, 864–871). Proteins with recognizable sequence homology have been identified in vertebrates, plants, insects and viruses but not, thus far, in prokaryotes (Huber, R. (1989) Biochemistry, 28, 8951–8966; Sasaki, T. (1991) Eur J Biochem, 202, 255–261; Komiyama, T., (1994) The Journal of Biological Chemistry, 269, 19331–19337). Current models of serpin structure are based largely on seminal X-ray crystallographic studies of one member of the family, (α1-antitrypsin (α1AT), also called (α1-proteinase inhibitor (Huber, R. (1989) Biochemistry, 28, 8951–8966). The structure of a modified form of α1AT, cleaved in its reactive center, was solved by Loebermann and coworkers in 1984 (Loebermann, H., et. al. (1984) J Mol Biol, 177, 531–557). An interesting feature of this structure was that the two residues normally comprising the reactive center (Met-Ser), were found on opposite ends of the molecule, separated by almost 70 Å. Loebermann and coworkers proposed that a relaxation of a strained configuration takes place upon cleavage of the reactive center peptide bond, rather than a major rearrangement of the inhibitor structure. In this model, the native reactive center is part of an exposed loop, also called the strained loop (Loebermann, H., et. al. (1984) J Mol Biol, 177, 531–557; Carrell, R. W., & Boswell, D. R. (1986) In A. J. Barrett & G. Salvesen (Eds.), Proteinase Inhibitors. (pp. 403–420). Amsterdam: Elsevier Science Publishers (Biomedical Division); Sprang, S. R. (1992) Trends Biochem Sci, 17, 49–50). Upon cleavage, this loop moves or "snaps back", becoming one of the central strands in a major β-sheet structure (β-sheet A). This transformation is accompanied by a large increase in thermal stability (Carrell, R. W., & Owen, M. C. (1985) Nature, 317, 730–732; Gettins, P., & Harten, B. (1988) Biochemistry, 27, 3634–3639; Bruch, M., Weiss, V., & Engel, J. (1988) The Journal of Biological Chemistry, 263, 16626–16-630; Lawrence, D. A., et. al. (1994) The Journal of Biological Chemistry, 269, 27657–27662).

Recent crystallographic structures of several native serpins, with intact reactive center loops, have confirmed Loebermann's hypothesis that the overall native serpin structure is very similar to cleaved α1AT, but that the reactive center loop is exposed above the plane of the molecule (Schreuder, H. A., et. al. (1994) Nature Structural Biology, 1, 48–54; Carrell, R. W. et al. (1994) Structure, 2, 257–270; Stein, P. E., et. al. (1990) Nature, 347, 99–102; Wei, A., et. al. (1994) Nature Structural Biology, 1, 251–258). Additional evidence for this model has come from studies where synthetic peptides, homologous to the reactive center loops of α1AT, antithrombin III (ATIII), or PAI-1 when added in trans, incorporate into their respective molecules, presumably as a central strand of β-sheet A (Björk, I., et. al. (1992) The Journal of Biological Chemistry, 267, 1976–1982; Björk, I., et. al. (1992) The Journal of Biological Chemistry, 267, 19047–19050; Schulze, A. J., et. al. (1990) Eur J Biochem, 194, 51–56; Carrell, R. W., Evans, D. L., & Stein, P. E. (1991) Nature, 353, 576–578; Kvassman, (1995) J Biol Chem, 270, 27942–27947). This leads to an increase in thermal stability similar to that observed following cleavage of a serpin at its reactive center, and converts the serpin from an inhibitor to a substrate for its target proteinase. A third serpin structural form has also been identified, the so-called latent conformation. In this structure the reactive center loop is intact, but instead of being exposed, the entire amino-terminal side of the reactive center loop is inserted as the central strand into β-sheet A (Mottonen, J., et. al. (1992) Nature, 355, 270–273). This accounts for the increased stability of latent PAI-1 (Lawrence, et. al. (1994) Biochemistry, 33, 3643–3648) as well as its lack of inhibitory activity (Hekman, C. M., & Loskutoff, D. J. (1985) The Journal of Biological Chemistry, 260, 11581–11587). The ability to adopt this conformation is not unique to PAI-1, but has also now been shown for ATIII and β1AT (Carrell, R. W. et al. (1994) Structure, 2, 257–270; Lomas, D. A., et. al. (1995) J Biol Chem, 270, 5282–5288). Together, these data have led to the hypothesis that active serpins have mobile reactive center loops, and that this mobility is essential for inhibitor function (Lawrence, D. A., et. al. (1990) The Journal of Biological Chemistry, 265, 20293–20301; Carrell, R. W., Evans, D. L., & Stein, P. E. (1991) Nature, 353, 576–578; Carrell, R. W., & Evans, D. L. I. (1992) Curr Opin Struct Biol, 2, 438–446; Lawrence, D. A., et. al. (1994) The Journal of Biological Chemistry, 269, 27657–27662; Shore, J. D., et. al. (1994) The Journal of Biological Chemistry, 270, 5395–5398; Lawrence, D. A., et. al. (1995) J. Biol Chem, 270, 25309–25312; Fa, M., et. al., (1995) Biochemistry, 34, 13833–13840; Olson, S. T., et. al. (1995) J Biol Chem, 270, 30007–30017). The large increase in thermal stability observed with loop insertion, is presumably due to reorganization of the five stranded β-sheet A from a mixed parallel-antiparallel arrangement to a six stranded, predominantly antiparallel β-sheet (Carrell, R. W., & Owen, M. C. (1985) Nature, 317, 730–732; Gettins, P., & Harten, B. (1988) Biochemistry, 27, 3634–3639; Bruch, M., Weiss, V., & Engel, J. (1988) The Journal of Biological Chemistry, 263, 16626–16630; Lawrence, et. al. (1994) Biochemistry, 33, 3643–3648). This dramatic stabilization has led to the suggestion that native inhibitory serpins may be metastable structures, kinetically trapped in a state of higher free energy than their most stable thermodynamic state (Lawrence, D. A., et. al. (1995) J. Biol Chem, 270, 25309–25312; Lee, K. N., et. al. (1996) Nature Structural Biology, 3, 497–500). Such an energetically unfavorable structure would almost certainly be subject to negative selection, and thus its retention in all inhibitory serpins implies that it has been conserved for functional reasons.

The serpins act as "suicide inhibitors" that react only once with a target proteinase forming an SDS-stable complex. They interact by presenting a "bait" amino acid residue, in their reactive center, to the enzyme. This bait residue is thought to mimic the normal substrate of the enzyme and to associate with the specificity crevice, or S1 site, of the enzyme (Carrell, R. W., & Boswell, D. R. (1986) In A. J. Barrett & G. Salvesen (Eds.), Proteinase Inhibitors. (pp. 403–420). Amsterdam: Elsevier Science Publishers (Biomedical Division); Huber, R. (1989) Biochemistry, 28, 8951–8966; Bode, W., & Huber, R. (1994) Fibrinolysis, 8, 161–171.). The bait amino acid is called the P1 residue, with the amino acids toward the N-terminal side of the scissile reactive center bond labeled in order P 1 P2 P3 etc. and the amino acids on the carboxyl side labeled P I' P2' etc. (Carrell, R. W., & Boswell, D. R. (1986) In A. J. Barrett & G. Salvesen (Eds.), Proteinase Inhibitors. (pp. 403–420). Amsterdam: Elsevier Science Publishers (Biomedical Division)). The reactive center P1-P 1' residues, appear to play a major role in determining target specificity. This point was dramatically illustrated by the identification of a unique human mutation, α1AT "Pittsburgh", in which a single amino acid substitution of Arg for Met at the P1 residue converted α1AT from an inhibitor of elastase to an efficient inhibitor of thrombin, resulting in a unique and ultimately fatal bleeding disorder (Owen, M. C., et. al. (1983) N Engl J Med, 309, 694–698). Numerous mutant serpins have been constructed, demonstrating a wide range of changes in target specificity, particularly with substitutions at P1 (York, J. D., et. al. (1991) The Journal of Biological Chemistry, 266, 8495–8500; Strandberg, L., et. al. (1991) The Journal of Biological Chemistry, 266, 13852–13858; Shubeita, H. E., et. al. (1990) The Journal of Biological Chemistry, 265, 18379–18385; Lawrence, D. A., et. al. (1990) The Journal of Biological Chemistry, 265, 20293–20301; Sherman, P. M., et. al., (1992) The Journal of Biological Chemistry, 267, 7588–7595).

The exact structure of the complex between serpins and their target proteinases has been controversial. Originally it was thought that the complex was covalently linked via an ester bond between the active site serine residue of the proteinase and the new carboxyl-terminal end of the P1 residue, forming an acyl-enzyme complex (Moroi, M., & Yamasaki, M. (1974) Biochim Biophys Acta, 359, 130–141; Owen, W. G. (1975) Biochim Biophys Acta, 405, 380–387; Cohen, A. B., et al., (1977) Proceedings of the National Academy of Sciences, USA, 74, 4311–4314; Nilsson, T., & Wiman, B. (1982) FEBS Lett, 142, 111–114). However, in the late 1980s and early 1990s it was suggested that this interpretation was incorrect, and that the serpin-proteinase complex is instead trapped in a tight non-covalent association similar to the so called standard mechanism inhibitors of the Kazal and Kunitz family (Longstaff, C., & Gaffney, P., J. (1991) Biochemistry, 30, 979–986; Shieh, B. H., et. al. (1989) J Biol Chem, 264, 13420–13423; Potempa, J., et. al. (1994) The Journal of Biological Chemistry, 269, 15957–15960). Alternatively, one study suggested a hybrid of these two models where the complex was frozen in a covalent but un-cleaved tetrahedral transition state configuration (Matheson, N. R., et. al. (1991) The Journal of Biological Chemistry, 266, 13489–13491). Recently however, new data by several groups have suggested that the debate has come full circle, with various studies using independent methods indicating that the inhibitor is indeed cleaved in its reactive-center and that the complex is most likely trapped as a covalent acyl-enzyme complex (Lawrence, D. A., et. al. (1995) J. Biol Chem, 270, 25309–25312; Olson, S. T., et. al. (1995) J Biol Chem, 270, 30007–30017; Fa, M., et. al., (1995) Biochemistry, 34, 13833–13840; Wilczynska, M., et. al. (1995) The Journal of Biological Chemistry, 270, 29652–29655; Lawrence, D. A., et. al. (1994) The Journal of Biological Chemistry, 269, 27657–27662; Shore, J. D., et. al. (1994) The Journal of Biological Chemistry, 270, 5395–5398; Plotnick, M. I., et. al. (1996) Biochemistry, 35, 7586–7590).

Recently, three groups have almost simultaneously proposed similar mechanisms for serpin inhibition (Lawrence, D. A., et. al. (1995) J. Biol Chem, 270, 25309–25312; Wilczynska, M., et. al. (1995) The Journal of Biological Chemistry, 270, 29652–29655; Wright, H. T., & Scarsdale, J. N. (1995) Proteins, 22,210–225). This model suggests that upon encountering a target proteinase, a serpin binds to the enzyme forming a reversible complex that is similar to a Michaelis complex between an enzyme and substrate. Next, the proteinase cleaves the P1-P1' peptide bond resulting in formation of a covalent acyl-enzyme intermediate. This cleavage is coupled to a rapid insertion of the reactive center loop (RCL) into β-sheet A at least up to the P9 position. Since the RCL is covalently linked to the enzyme via the active-site Ser, this transition should also affect the proteinase, significantly changing its position relative to the inhibitor. If, during this transition, the RCL is prevented from attaining full insertion because of its association with the enzyme, and the complex becomes locked, with the RCL only partially inserted, then the resulting stress might be sufficient to distort the active site of the enzyme. This distortion would then prevent efficient deacylation of the acyl-enzyme intermediate, thus trapping the complex. However, if RCL insertion is prevented, or if deacylation occurs before RCL insertion then the cleaved serpin is turned over as a substrate and the active enzyme released. This means that what determines whether a serpin is an inhibitor or a substrate is the ratio of $k_{diss}$ to $k_{stab}$ If deacylation ($k_{diss}$) is faster than RCL insertion ($k_{stab}$) then the substrate reaction predominates. However, if RCL insertion and distortion of the active site can occur before deacylation then the complex is frozen as a covalent acyl-enzyme. A similar model was first proposed-in 1990 (Lawrence, D. A., et. al. (1990) The Journal of Biological Chemistry, 265, 20293–20301) and is consistent with studies demonstrating that RCL insertion is not required for proteinase binding but is necessary for stable inhibition (Lawrence, D. A., et. al. (1994) The Journal of Biological Chemistry, 269, 27657–27662) as well as the observation that only an active enzyme can induce RCL insertion (Olson, S. T., et. al. (1995) J Biol Chem, 270, 30007–30017). Very recently, direct evidence for this model was provided by Plotnick et al., who by NMR observed an apparent distortion of an enzyme's catalytic site in a serpin-enzyme complex (Plotnick, M. I., et. al. (1996) Biochemistry, 35, 7586–7590). In conclusion, these data suggest that serpins act as molecular springs where the native structure is kinetically trapped in a high energy state. Upon association with an enzyme some of the energy liberated by RCL insertion is used to distort the active site of the enzyme, preventing deacylation and trapping the complex.

Nervous System

During the development of the nervous system, neurons form axons which extend along a prespecified path into the target area, where they engage in the formation and refinement of synaptic connections. These stages depend critically on the capability of the axonal growth cones to interact with a variety of structures which they encounter along their way and at their destination. These structures include cell surfaces of neuronal and non-neuronal origin and the extracellular matrix. Along their trajectory and at their target sites, growth cones not only receive and respond to signals from their local environment, but also actively secrete macromolecules. In particular, secreted proteases have been implicated in supporting the growth cone advancement through the tissue. More than a decade ago, it was demonstrated that plasminogen activators are axonally secreted by neurons in culture. Recently, their occurrence in the developing rat nervous system during the period of axon outgrowth has been revealed. Moreover, several pieces of evidence were presented which indicated that serine proteases, such as plasminogen activators or thrombin, are involved in restructuring of the synaptic connectivity during development and regeneration. Such processes include elimination during development and synaptic plasticity associated with learning and memory in the adult. See, for instance, Osterwalder, T., et al., "Neuroserpin, an axonally secreted serine protease inhibitor," *EMBO J.* 15:2944–2953 (1996).

During normal development of the nervous system, about 50% of postmitotic lumbosacral motoneurons undergo naturally occurring (programmed) cell death during a period when these cells are forming synaptic connections with their target muscles. Naturally occurring motoneuron death has been described in many vertebrate species, including chicken, mouse, rat, and human embryos or fetuses. For example, programmed motoneuron death occurs between embryonic day (E)6 and E10 in the chicken. This system has been used as a biological model for testing different neurotrophic agents on motoneuron survival in vivo. See, for instance, Houenou, L. J., et al., "A serine protease inhibitor, protease nexin I, rescues motoneurons from naturally occurring and axotomy-induced cell death," *Proc. Natl. Acad. Sci. USA* 92:895–899 (1995).

Although programmed cell death is completed before birth in mammals, the maintenance of motoneurons continues to be dependent on support from the target for some time after birth. Thus, if transection of motor axons is performed in neonatal mammals and reinnervation is prevented, a large number of motoneurons degenerate and die. Axotomy-induced death of motoneurons has also been extensively used as a model for testing the survival effects of various agents, including neurotrophic and growth factors on motoneurons.

Protease nexin I (PNI), also known as glia-derived nexin, is a 43–47-kDa protein that was first found secreted by cultured fibroblasts but is also produced by glial (glioma and primary) and skeletal muscle cells. PNI has been shown to promote neurite outgrowth from different neuronal cell types. These include neuroblastoma cells, as well as primary hippocampal and sympathetic neurons. The neurite promoting activity of PNI in vitro is mediated by inhibition of thrombin, a potent serine protease. PNI (mRNA and protein) is transiently up-regulated in rat sciatic nerve after axotomy, and PNI-producing cells are localized distal to the lesion site. This up-regulation of PNI occurs 2–3 days after a similar up-regulation of prothrombin and thrombin in the distal stump. Free PNI protein is significantly decreased, while endogenous PNI-thrombin complexes are increased, in various anatomical brain regions, including hippocampus of patients with Alzheimer disease. When considered together with the recent demonstration that PNI can promote the in vitro survival of mixed mouse spinal chord neurons and that PNI is released from glia cells by neuropeptides such as vasoactive intestinal polypeptide, these observations suggest that PNI may play a physiological role in neuronal survival, differentiation, and/or axonal regeneration in vivo.

Recently, it has been reported that PNI rescues spinal motoneuron death in the neonatal mouse. Houenou, L. J. et al., 1995, supra. The survival effect of PNI on motoneurons during the period of programmed cell death was not associated with increased intramuscular nerve branching. PNI also significantly increased the nuclear size of motoneurons during the period of programmed cell death and prevented axotomy-induced atrophy of surviving motoneurons. These results indicate a possible role of PNI as a neurotrophic agent. They also support the idea that serine proteases or, more precisely, the balance of proteases and serpins may be involved in regulating the fate of neuronal cells during development.

More recently, a cDNA encoding an axonally secreted glycoprotein of central nervous system (CNS) and peripheral nervous system (PNS) neurons of the chicken has been cloned and sequenced. Osterwalder, T., et al., 1996) supra. Analysis of the primary structural features characterized this protein as a novel member of the serpin superfamily which was therefore called "neuroserpin." No demonstration of inhibition of any protease was included in this report, however. In situ hybridization revealed a predominately neuronal expression during the late stages of neurogenesis and in the adult brain in regions which exhibit synaptic plasticity. Thus, it has been suggested that neuroserpin may function as an axonally secreted regulator of the local extracellular proteolysis involved in the reorganization of the synaptic connectivity during development and synapse plasticity in the adult. A role for serine proteases and serpins in neuronal remodeling is further supported by the finding that elevated tPA mRNA and protein levels are found in cerebellar Purkinje neurons of rats undergoing motor learning (Seeds N W; Williams B L; Bickford P. C., "Tissue plasminogen activator induction in Purkinje neurons after cerebellar motor learning." *Science* 270:1992–4 (1995)).

The amplification of a human cDNA fragment of about 450 bp corresponding to the region of the chicken cDNA encoding the putative reactive site loop of the so-called neuroserpin, using a polymerase chain reaction with two pairs of nested primers flanking that region, has also been reported. Osterwalder, T., et al., 1996, supra, page 2946. The authors also reported that the deduced amino acid sequences of the human and corresponding mouse cDNA exhibited a sequence identity of 88% and 87% respectively, with chicken neuroserpin. However, the human DNA sequence in a related serpin derived from human hypothalamus is described in WO96/40922 published 19 Dec. 1996 is about 99% the same as the present invention.

Thus, there is a need for human polypeptides that function as serpins in the regulation of various serine proteases, particularly in the nervous system, since disturbances of such regulation may be involved in disorders relating to hemostasis, angiogenesis, tumor metastisis, cellular migration and ovulation, as well as neurogenesis; and, therefore, there is a need for identification and characterization of such human polypeptides which can play a role in preventing, ameliorating or correcting such disorders.

A related serpin (CAPE) derived from human hypothalamus is described in WO96/40922 published 19 Dec. 1996. This published CAPE serpin differs from the BAIT of the present invention by having 17 of its CAPE amino acids replaced by 23 different BAIT amino acids. Specifically when numbering from the first methionine, HGS Alamine (27) is replaced by CAPE Valine; HGS Aspartic Acid (173) replaces an unknown CAPE amino acid; the six HGS aminoacids 319–324 are replaced in CAPE by 5 different amino acids, and the 15 HGS amino acids 351–365 are replaced by only 10 CAPE amino acids. Thus the BAIT of the present invention contains 23 amino acids in 4 locations that are not found in the CAPE polypeptide.

Stroke

Stroke is the second most common cause of death in the world after heart disease and a leading cause of disability. The World Health Report 1999: Making A Difference. 1–121. 1999. Geneva, Switzerland, The World Health Organization. It is estimated that in United States there is a stroke approximately every minute and a person dies of stroke about every 3.5 minutes. Thorvaldsen P, et. al. Stroke (1995) 26:361–367. Various strategies have been employed to reduce stroke morbidity and mortality, one of which has been thrombolysis with tPA in order to restore cerebral blood flow to ischemic brain tissue. Thrombolysis with tPA produces arterial recanalization in 40–67% of patients (Caplan L R, et. al. N. Engl. J. Med. 1997;337:1309–1310), and is associated with absolute improvement in neurological function after 90 days in 12% of the patients treated within 3 hours of the onset of symptoms. N. Engl. J. Med. 1995;333: 1581–1587. However, in seeming contradiction to these results, animal studies have demonstrated that tPA-deficient mice have a 41% decrease in stroke size and a 61% increase in neuronal survival compared with wild type animals following middle cerebral artery occlusion. Wang Y F, et. al. Nat Med. 1998;4:228–231. Although these results have been recently challenged (Tabrizi P., et al. Arterioscler. Thromb. Vasc. Biol. 1999; 19:2801–2806; Klein G M, et al. Neurology 1999;52:1381–1384) they have also been reproduced by others. Nagai N, et al. Circulation 1999;99:2440–2444. Furthermore, this latter study also demonstrated that animals deficient in plasminogen had an increase in stroke volume, while animals deficient in the primary plasmin inhibitor, alpha2-antiplasmin, had a decrease in stroke size similar to tPA null mice, suggesting a plasminogen-independent function for tPA in cerebral ischemia.

In both rats and mice, tPA expression is increased by events that require neuronal plasticity, such as synaptic remodeling, long term potentiation, kindling and seizures. Qian Z, et. al. Nature 1993;361:453–457; Seeds N W, et. al. Science 1995;270:1992–1994; Carroll P M, et. al. Development 1994;120:3173–3183. Expression of tPA is also correlated with CNS development and maintenance, and in the modulation of cell—cell and cell-extracellular matrix interactions. As in stroke, tPA-deficient mice are protected from excitotoxin-induced neuronal death. Friedman G C, Brain Res. Dev. Brain Res. 1994; 81:41–49; Ware J H, et. al. Brain Res. Bull. 1995;37:275–281. However, in contrast to stroke, plasminogen-deficient mice are also protected from excitotoxic injury (Ware J H, et. al. Brain Res. Bull. 1995;37: 275–281; Sappino A P, et. al. J. Clin. Invest. 1993;92: 679–685; Tsirka S E, et. al. Nature 1995;377:340–344; Tsirka S E, et. al. Nature 1996;384:123–124; Tsirka S E, et. al. J. Neurosci. 1997;17:543–552) and it has been suggested that tPA and plasminogen may promote excitotoxin-induced neuronal death through proteolysis of the neuronal extracellular matrix (ECM). Chen Z L Cell 1997;91:917–925.

Following stroke there is a densely ischemic area where neurons are irreversibly damaged, surrounded by an area known as "ischemic penumbra", where cerebral blood flow is sufficiently decreased to abolish electrical potentials yet sufficient to allow maintenance of membrane potentials and cellular ionic homeostasis. Symon L., Acta Neurol. Scand. Suppl. 1980;78:175–90:175–190; Hakim A M, Can. J Neurol. Sci. 1987;14:557–559; Hossmann K A, Ann. Neurol. 1994;36:557–565. This zone of penumbra has also been observed in magnetic resonance image studies (MRI) of rats in the area surrounding the necrotic core. Pierce A R, et. al. J Cereb. Blood Flow Metab. 1997;17:183–190; Grohn O H, et al., J Cereb. Blood Flow Metab. 1998;18:911–920; Hoehn-Berlage M, et. al., J Cereb. Blood Flow Metab. 1995;15:1002–1011. With time, this potentially salvageable area of penumbra, or reversible ischemia, tends to become infarcted. In vivo microdialysis has demonstrated that after cerebral ischemia there is a large release of excitotoxins (Benveniste H, et. al., J. Neurochem. 1984;43:1369–1374; Globus M Y, J. Neurochem. 1988;51:1455–1464; Miyashita K, et. al., Neuroreport. 1994;5:945–948; Uchiyama-Tsuyuki Y, et. al., J. Neurochem. 1994;62:1074–1078) not only in the infarcted core but also in the area of ischemic penumbra (Takagi K, et. al. J Cereb. Blood Flow Metab. 1993;13: 575–585), where the presence of apoptotic cells has also been described. Li Y, et. al. J Cereb. Blood Flow Metab. 1995;15:389–397; Linnik M D, et. al., Stroke 1993;24: 2002–2008; Linnik M D, et. al., Brain Res. Mol. Brain Res. 1995;32:116–124. Since tPA may play an significant role in both excitotoxin- and ischemia-induced neuronal degenera-

SUMMARY OF THE INVENTION

The present invention provides isolated nucleic acid molecules comprising a polynucleotide encoding the human BAIT polypeptide having the amino acid sequence shown in FIGS. 1A–1B (SEQ ID NO:2) or the amino acid sequence encoded by the cDNA clone deposited in a bacterial host as ATCC™ (American Type Culture Collection™) Deposit Number 97722 on Sep. 18, 1996. The nucleotide sequence determined by sequencing the deposited BAIT clone, which is shown in FIGS. 1A–1B (SEQ ID NO:1), contains an open reading frame encoding a complete polypeptide of 410 amino acid residues, including an initiation codon at positions 89–91, and a predicted molecular weight of about 46.4 kDa. The encoded polypeptide has a leader sequence of 18 amino acids, underlined in FIGS. 1A–1B; and the amino acid sequence of the expressed mature BAIT protein is also shown in FIGS. 1A–1B, as amino acid residues 19–410 (SEQ ID NO: 2).

The human BAIT protein of the present invention has been shown to exhibit selective inhibition of tissue-type plasminogen activator (t-PA) with relatively little inhibition of trypsin, thrombin or urokinase-type plasminogen activator (u-PA). The human BAIT polypeptide also shares extensive sequence homology with the translation product of the mRNA for a serpin-related protein isolated from brain cDNA library which has been named "neuroserpin" (SEQ ID NO: 3) (see FIGS. 2A–2B). As noted above, neuroserpin in the chicken is thought to play an important role in regulation of local extracellular proteolysis involved in the reorganization of the synaptic connectivity during development and synapse plasticity in the adult. The homology between neuroserpin and BAIT (90% amino acid similarity) indicates that BAIT also may play a similar role in neurogenesis in humans.

Thus, one aspect of the invention provides an isolated nucleic acid molecule comprising a polynucleotide having a nucleotide sequence selected from the group consisting of: (a) a nucleotide sequence encoding the BAIT polypeptide having the complete amino acid sequence in FIGS. 1A–1B (SEQ ID NO: 2); (b) a nucleotide sequence encoding the expressed mature BAIT polypeptide having the amino acid sequence at positions 19–410 in FIGS. 1A–1B (SEQ ID NO: 2); (c) a nucleotide sequence encoding the BAIT polypeptide having the complete amino acid sequence encoded by the cDNA clone contained in ATCC™ Deposit No. 97722; (d) a nucleotide sequence encoding the mature BAIT polypeptide having the amino acid sequence encoded by the cDNA clone contained in ATCC™ Deposit No. 97722; and (e) a nucleotide sequence complementary to any of the nucleotide sequences in (a), (b), (c) or (d) above.

Further embodiments of the invention include isolated nucleic acid molecules that comprise a polynucleotide having a nucleotide sequence at least 99.1% identical, and more preferably at least 99.2%, 99.3%, 99.4%, 99.5%, 99.6. %, 99.7%, 99.8% or 99.9% identical, to any of the nucleotide sequences in (a), (b), (c), (d) or (e), above, or a polynucleotide which hybridizes under stringent hybridization conditions to a polynucleotide in (a), (b), (c), (d) or (e), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a BAIT polypeptide having an amino acid sequence in (a), (b), (c) or (d), above.

The present invention also relates to recombinant vectors, which include the isolated nucleic acid molecules of the present invention, and to host cells containing the recombinant vectors, as well as to methods of making such vectors and host cells and for using them for production of BAIT polypeptides or peptides by recombinant techniques.

The invention further provides an isolated BAIT polypeptide having an amino acid sequence selected from the group consisting of: (a) the amino acid sequence of the BAIT polypeptide having the complete amino acid sequence including the leader sequence shown in FIGS. 1A–1B (SEQ ID NO: 2); (b) the amino acid sequence of the mature BAIT polypeptide (without the leader) having the amino acid sequence at positions 19–410 in FIGS. 1A–1B (SEQ ID NO:2); (c) the amino acid sequence of the BAIT polypeptide having the complete amino acid sequence, including the leader, encoded by the cDNA clone contained in ATCC™ Deposit No. 97722; and (d) the amino acid sequence of the mature BAIT polypeptide having the amino acid sequence encoded by the cDNA clone contained in ATCC™ Deposit No. 97722. The polypeptides of the present invention also include polypeptides having an amino acid sequence at least 95% identical, more preferably at least 96% identical, and still more preferably 97%, 98% or 99% identical to those described in (a), (b), (c) or (d) above, as well as polypeptides having an amino acid sequence with at least 96% similarity, and more preferably at least 97%, 98% or 99% similarity, to those above.

An additional embodiment of this aspect of the invention relates to a peptide or polypeptide which has the amino acid sequence of an epitope-bearing portion of a BAIT polypeptide having an amino acid sequence described in (a), (b), (c) or (d), above. Peptides or polypeptides having the amino acid sequence of an epitope-bearing portion of a BAIT polypeptide of the invention include portions of such polypeptides with at least six or seven, preferably at least nine, and more preferably at least about 30 amino acids to about 50 amino acids, although epitope-bearing polypeptides of any length up to and including the complete amino acid sequence of a polypeptide of the invention described above also are included in the invention.

In another embodiment, the invention provides an isolated antibody that binds specifically to a BAIT polypeptide having an amino acid sequence described in (a), (b), (c) or (d) above. The invention further provides methods for isolating antibodies that bind specifically to a BAIT polypeptide having an amino acid sequence as described herein. Such antibodies are useful diagnostically or therapeutically as described below.

The present invention also provides a screening method for identifying compounds capable of enhancing or inhibiting a biological activity of the BAIT polypeptide, which involves contacting a protease which is inhibited by the BAIT polypeptide with the candidate compound in the presence of a partially inhibitory amount of BAIT polypeptide, assaying proteolytic activity of the protease on a susceptible substrate in the presence of the candidate compound and partially inhibitory amount of BAIT polypeptide, and comparing the proteolytic activity to a standard level of activity, the standard being assayed when contact is made between the protease and its substrate in the presence of the partially inhibitory amount of BAIT polypeptide and the absence of the candidate compound In this assay, an increase in inhibition of proteolytic activity over the standard indicates that the candidate compound is an agonist of BAIT inhibitory activity and a decrease in inhibition of proteolytic activity compared to the standard indicates that the compound is an antagonist of BAIT inhibitory activity.

In another aspect, a screening assay for agonists and antagonists is provided which involves determining the effect a candidate compound has on BAIT binding to the active site of a susceptible protease. In particular, the method involves contacting the BAIT-susceptible protease with a BAIT polypeptide and a candidate compound and determining whether BAIT polypeptide binding to the BAIT-susceptible protease is increased or decreased due to the presence of the candidate compound.

The present inventor has discovered that BAIT is expressed in whole human brain, and to a much lesser extent in adult pancreas and adult heart. For a number of disorders of the central or peripheral nervous system, significantly higher or lower levels of BAIT gene expression may be detected in certain tissues (e.g., adult brain, embryonic retina, cerebellum and spinal chord) or bodily fluids (e.g., serum, plasma, urine, synovial fluid or spinal fluid) taken from an individual having such a disorder, relative to a "standard" BAIT gene expression level, i.e., the BAIT expression level in healthy tissue from an individual not having the nervous system disorder. Thus, the invention provides a diagnostic method useful during diagnosis of nervous system disorders, which involves: (a) assaying BAIT gene expression level in cells or body fluid of an individual; (b) comparing the BAIT gene expression level with a standard BAIT gene expression level, whereby an increase or decrease in the assayed BAIT gene expression level compared to the standard expression level is indicative of disorder in the nervous system.

An additional aspect of the invention is related to a method for treating an individual in need of an increased level of BAIT activity in the body (i.e., insufficient protease inhibitory activity of BAIT and/or excessive protease activity of a protease inhabited by BAIT, particularly t-PA), which method comprises administering to such an individual a composition comprising a therapeutically effective amount of an isolated BAIT polypeptide of the invention or an agonist thereof. Preferred embodiments include a method of treating stroke, brain infarctions, or any other brain disease associated with the loss of oxygen.

A still further aspect of the invention is related to a method for treating an individual in need of a decreased level of BAIT activity in the body (i.e., less inhibition of a protease susceptible to BAIT) comprising, administering to such an individual a composition comprising a therapeutically effective amount of a BAIT antagonist. Preferred antagonists for use in the present invention are BAIT-specific antibodies. Preferred embodiments include a method of treating stroke, brain infarctions, or any other brain disease associated with the loss of oxygen.

BRIEF DESCRIPTION OF THE FIGURES

FIGS. 1A–1B shows the nucleotide sequence (SEQ ID NO:1) and deduced amino acid sequence (SEQ ID NO:2) of the human BAIT polypeptide. The leader sequence of 18 amino acids is underlined.

FIG. 2A show the regions of identity between the amino acid sequences of the human BAIT protein (SEQ ID NO: 2) and other indicated serpins with which the human BAIT polypeptide (SEQ ID NO: 2) shares significant homology, as follows: bovine plasminogen activator inhibitor-1 (BovPAI1; SEQ ID NO:4); rat glial-derived nexin I (RatGDNI; SEQ ID NO:5); mouse antithrombin III (MusATIII; SEQ ID NO:6); chicken neuroserpin (ChkNSP; SEQ ID NO:3). The sequence alignment was generated with the Pileup module of the Genetics Computer Group (Wisconsin Package, Version 8, using the parameters GapWeight=3.000, GapLengthWeight=0.100). The reactive site loops (from positions 415–452 in FIGS. 2A–2B (corresponding to BAIT residues 342–378 in FIGS. 1A–1B; SEQ ID NO:2) are double-underlined, and critical positions in this sequence are labeled $P_{17}$ to $P_1$ and $P_1'$ according to Schechter and Berger, *Biochem. Biopys. Res. Commun.* 27:157–162 (1967). The putative reactive site (cleaved by a target protease), between Arg at BAIT position 362 and Met at BAIT position 363, is marked with an arrow (⇑).

FIGS. 4A–4G show the relationship between the deposited cDNA clone (identified as clone HSDFB 5 50 1 X; SEQ ID NO:1) and three related cDNA clones of the invention, designated HPBCT06R (SEQ ID NO:7), HBPDG64R (SEQ ID NO: 8), and HPBCR79R (SEQ ID NO: 9).

FIG. 7A shows the area of penumbra, FIG. 7B shows a similar area of the cortex contralateral to the stroke and FIG. 7C and FIG. 7D show the hippocampus. FIGS. 7A and 7C are ipsilateral to the stroke and FIGS. 7B and 7D are contralateral. Magnification is 100× in 7A and 7B and 40× in 7C and 7D.

FIGS. 9A–9B show SDS-PAGE zymography of brain extracts. FIG. 9A is SDS-PAGE zymography of brain extracts. Lane 1 is human tPA, lane 2 is a rat kidney extract as a marker for rat uPA, lanes 3–6 are extracts of brain 6 hours after reperfusion and lanes 7–10 are extracts 72 hours after reperfusion. Lanes 3 and 7 are ipsilateral to the infarct of PBS treated animals, lanes 4 and 8 are contralateral to the infarct. Lanes 5 and 9 are ipsilateral to the infarct in BAIT treated animals and lanes 6 and 10 are contralateral. FIG. 9B shows quantitative image analysis of PA activity from SDS-PAGE zymography of brain extracts 6 hours following reperfusion. The results represent the average fold increase in either tPA or uPA activity ipsilateral to the stroke relative to normal baseline PA activities contralateral to the stroke. PBS and Ns represent animals treated with either PBS or BAIT respectively, and n≧3 for each condition tested. P values ≦0.05 relative to the contralateral activity are shown, and errors represent S.E.M.

FIGS. 10A and 10D are developed without plasminogen, and all other Figures are developed with plasminogen. FIGS. 10C and 10F also contain anti-tPA antibodies. The white arrows indicate the area of the infarct. Magnification is 3×. FIG. 10G is immunohistochemical staining of tPA 6 hours after reperfusion. The black arrows indicate tPA positive blood vessels. FIG. 10H is immunohistochemical staining of uPA in the area of penumbra 72 hours after reperfusion. The magnification in FIGS. 10G and 10H is 400×.

FIGS. 11A and 11B show normal cortex in an animal without stroke. FIG. 11A was developed with anti-laminin but without pretreatment in vitro of the section with proteinase. FIG. 11B is an adjacent section with in vitro proteinase treatment. FIGS. 11C–F are from stroked animals and developed with anti-laminin and no proteinase treatment. FIGS. 11C–D are 10 minutes after reperfusion and FIGS. 11E–F are 6 hours after reperfusion. FIGS. 11C and 11E represent PBS-treated and FIGS. 11D and 11F BAIT-treated animals. Magnification is 100×.

In FIG. 12A, NC indicates the necrotic core, and P indicates the area of the penumbra. FIGS. 12B–C are high magnification images of the penumbra in control (FIG. 12B) and BAIT treated animals (FIG. 12C). Examples of cells considered to be apoptotic for the purposes of quantification are indicated with the open arrows while cells considered as necrotic are indicated with the closed arrows. Magnification in FIG. 12A is 40× and in FIGS. 12B–C 400×. FIG. 12D, quantitative analysis of apoptosis in the area of penumbra 72 hours after reperfusion. Quantitation was performed as described in the Examples and only cells with apoptotic bodies present (see FIG. 12B) were counted. Control represents animals injected with PBS (n=6). BAIT indicates animals injected with BAIT (n=6). P values <0.05 are shown, and errors represent S.E.M. FIG. 12E, quantitation of apoptosis was performed as in FIG. 12D at the times indicated, (○) PBS treated animals, (□) BAIT treated.

DETAILED DESCRIPTION

Figure 1B:
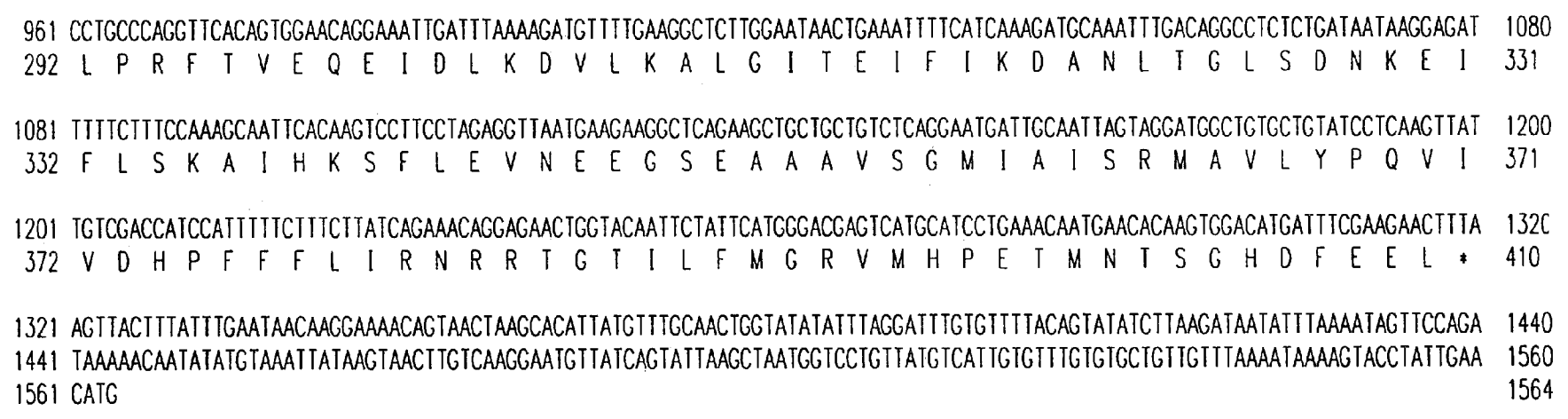
Figure 3:
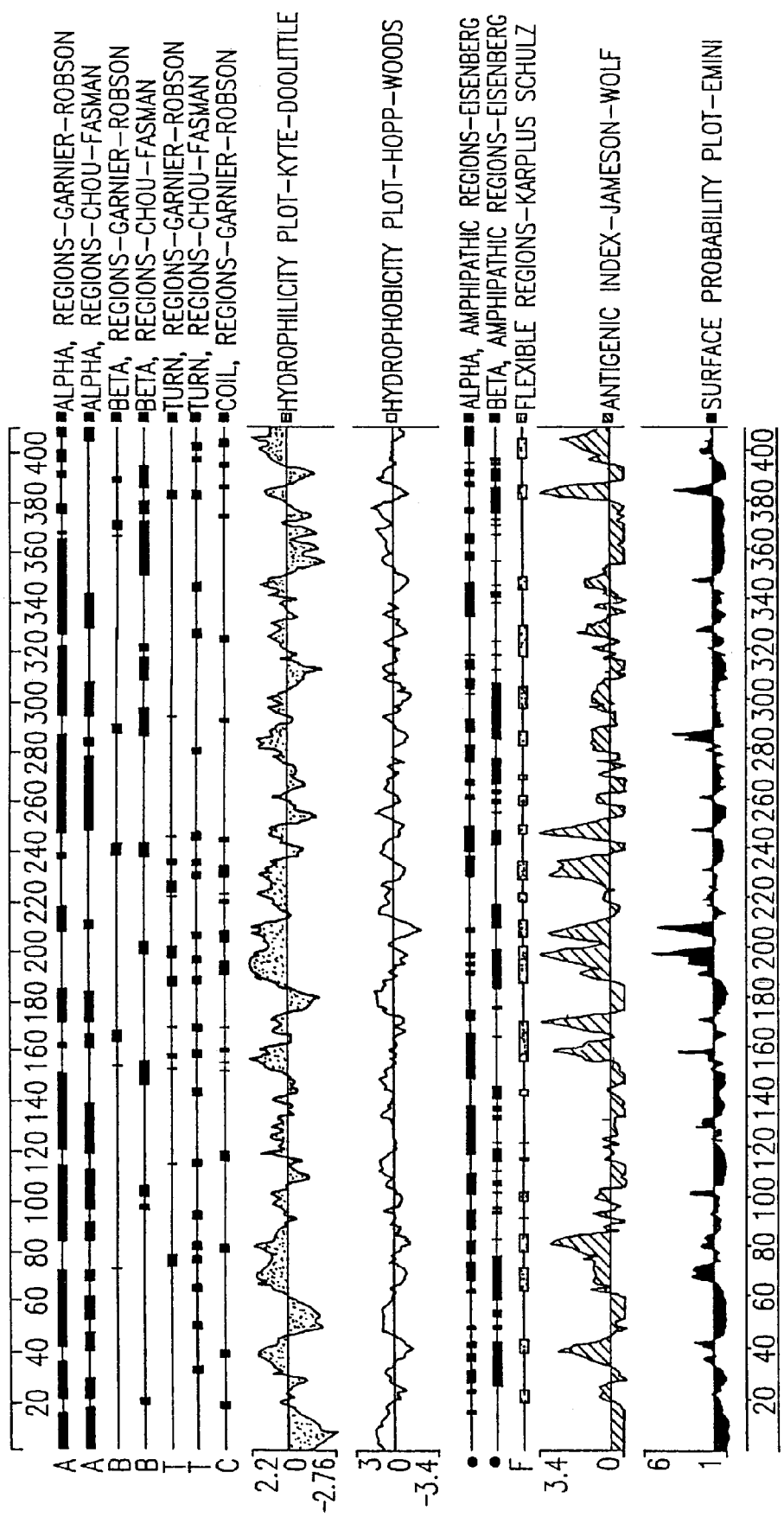
FIG. 3 shows an analysis of the BAIT amino acid sequence (SEQ ID NO;2). Alpha, beta, turn and coil regions; hydrophilicity and hydrophobicity; amphipathic regions; flexible regions; antigenic index and surface probability are shown. In the "Antigenic Index-Jameson-Wolf" graph, the location of the highly antigenic regions of the BAIT protein, i.e., regions from which epitope-bearing peptides of the invention may be obtained.

The present invention provides isolated nucleic acid molecules comprising a polynucleotide encoding a human BAIT polypeptide having the a-amino acid sequence shown in FIGS. 1A–1B (SEQ ID NO: 2), which was determined by sequencing a cloned cDNA. The nucleotide sequence shown in FIGS. 1A–1B (SEQ ID NO:1) was obtained by sequencing the HSDFB55SO1 clone, which was deposited on Sep. 18, 1996 at the American Type Culture Collection, 10801 University Boulevard, Manassas, Va. 20110, and given accession number ATCC™ 97722. The deposited clone is contained in the pBluescript SK(–) plasmid (Stratagene, La Jolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined as above approach, any nucleotide sequence determined herein may contain some errors. Nucleotide sequences determined by automation are typically at least about 99% identical, more typically at least about 99.1% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U. Using the information provided herein, such as the nucleotide sequence in FIGS. 1A–1B, a nucleic acid molecule of the present invention encoding a BAIT polypeptide may be obtained using standard cloning and screening procedures, such as those for cloning cDNAs using mRNA as starting material. Illustrative of the invention, the nucleic acid molecule described in FIGS. 1A–1B (SEQ ID NO:1) was discovered in a cDNA library derived from whole human brain. Additional cDNA clones of the BAIT gene were also identified in cDNA libraries from the following tissues: spinal cord, pineal gland and adrenal gland tumor. The determined nucleotide sequence of the BAIT cDNA of FIGS. 1A–1B (SEQ ID NO:1) contains an open reading frame encoding a protein of 410 amino acid residues, with an initiation codon at positions 89–91, and a predicted molecular weight of about 46.4 kDa. The encoded polypeptide has a leader sequence of 18 amino acids, underlined in FIGS. 1A–1B; and the amino acid sequence of the expressed mature protein is also shown in FIGS. 1A–1B, as amino acid residues 19–410 (SEQ ID NO: 2). The amino acid sequence of the BAIT protein shown in FIGS. 1A–1B (SEQ ID NO: 2) is about 80% identical to the published mRNA for chicken neuroserpin (Osterwalder, T., et al., 1996, supra) as shown in FIGS. 2A–2B. FIGS. 2A–2B shows the regions of identity between the amino acid sequences of the human BAIT protein and other indicated serpins with which the human BAIT polypeptide shares significant homology, as follows: bovine plasminogen activator inhibitor-1 (BovPAI1; SEQ ID NO: 4); rat glial-derived nexin I RatGDNI; SEQ ID NO: 5); mouse antithrombin III (MusATIII SEQ ID NO: 6); chicken neuroserpin (ChkNSP; SEQ ID NO: 3).

Sequence comparisons suggest that the chicken neuroserpin and BAIT are orthologs of one another and are distantly related to the better characterized mammalian serpins seen in FIGS. 2A–2B. There is 77% homology at the DNA level between BAIT and neuroserpin which translates into 90% and 80% amino acid similarity and identity, respectively. Amino acid identities between the non-human mammalian serpins and BAIT drop to about 30%. Moreover, within the functionally important reactive site loop, there is only one conservative amino acid change between BAIT and neuroserpin. There are 7 non-conservative changes between BAIT and PAI-1 in the same 38 amino acid region. The active site P1-P1' residues, however, are perfectly conserved between BAIT, neuroserpin, and PAI-1. The BAIT region corresponding to the ATIII heparin-binding site has 4 acidic amino acids which implies that heparin is not a co-factor as it is with ATIII. One potentially significant difference between BAIT and neuroserpin is the presence of 3 consensus N-linked glycosylation sites in the former versus 2 in the latter. Thus, BAIT and neuroserpin are likely to have similar enzymatic properties which may not overlap those of the related serpins.

Leader and Mature Sequences

The amino acid sequence of the complete BAIT protein includes a leader sequence and a mature protein, as shown in FIGS. 1A–1B (SEQ ID NO: 2). More in particular, the present invention provides nucleic acid molecules encoding one or more mature form(s) of the BAIT protein. Thus, according to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature BAIT polypeptide having the amino acid sequence encoded by the cDNA clone contained in the host identified as ATCC™ Deposit No. 97722. By the "mature BAIT polypeptide having the amino acid sequence encoded by the cDNA clone in ATCC™ Deposit No. 97722" is meant the mature form(s) of the BAIT protein produced by expression in a mammalian cell (e.g., COS cells, as described below) of the complete open reading frame encoded by the human DNA sequence of the clone contained in the vector in the deposited host.

In the present case, the deposited cDNA has been expressed in insect cells using a baculovirus expression vector, as described hereinbelow; and amino acid sequencing of the amino terminus of the secreted species indicated that the N-terminus of the mature BAIT protein comprises the amino acid sequence beginning at amino acid 19 of FIGS. 1A–1B (SEQ ID NO: 2). Thus, the leader sequence of the BAIT protein in the amino acid sequence of FIGS. 1A–1B are 18 amino acids, from position 1 to 18 in FIGS. 1A–1B (SEQ ID NO: 2).

The predicted 410 amino acids of the complete BAIT (prepro) polypeptide is expected to yield a 46.4 kDa band. The observed doublet band of 45 and 46 kDa upon expression in the baculovirus system was within the expected size range when the putative 18 amino acid signal peptide is removed. The approximate 1 kDa difference in the observed doublet bands may be explained by differential glycosylation. Evidence to support this includes the three consensus N-linked glycosylation site present in the nucleotide sequence (FIGS. 1A–1B) and the presence of oligosaccharide moieties on the purified protein determined experimentally.

N-Terminal and C-Terminal Deletion Mutants

In addition to the mature form of a protein being biologically active, it is known in the art for many proteins, including the mature form(s) of a secreted protein, that one or more amino acids may be deleted from the N-terminus without substantial loss of biological function. In the present case, deletions of at least up to 30 N-terminal amino acids from the end of the mature (secreted) polypeptide may retain some biological activity such as binding to the active site of at least one protease. However, even if deletion of one or more amino acids from the N-terminus of a protein results in modification of loss of one or more biological functions of the protein, other biological activities may still be retained. Thus, the ability of the shortened protein to induce and/or binding to antibodies which recognize the complete or mature protein generally will be retained when less than the majority of the residues of the complete or mature protein are removed from the N-terminus. Whether a particular polypeptide lacking N-terminal residues, of a complete protein retains such immunologic activities can readily be determined by routine methods described herein and otherwise known in the art. Similarly, deletion of one or more amino acids from the C-terminus of a protein also may provide shortened polypeptides which retain some or all biological activities.

In the baculovirus expression system the BAIT polypeptide was processed to produce multiple forms of BAIT. Beginning after the 18 amino acid leader, the next amino acids found on the baculovirus processed BAIT are as follows:

ATFPE: 40% (SEQ ID NO:19)
TFPEE: 30% (SEQ ID NO: 20)
MPEEA: 10% (SEQ ID NO: 21)

These are found within the first 7 amino acids of the mature BAIT in FIGS. 1A–1B. Therefor, there are multiple different N-terminal amino acids on the BAIT produced in the Baculovirus system.

Accordingly, the present invention further provides polypeptides having one or more residues from the amino terminus of the amino acid sequence of the complete BAIT polypeptide in SEQ ID NO: 2, up to 30 residues from the amino terminus after the leader cleavage site described above, and polynucleotides encoding such polypeptides. In particular, the present invention provides polypeptides having the amino acid sequence of residues n-410 of the amino acid sequence in SEQ ID NO: 2, where n is any integer in the range of 2–410, and preferably in the range of 2–49 specified range and 49 is the position of the 30th residue from the N-terminus of the mature polypeptide, after the above leader cleavage site, as shown in the amino acid sequence in SEQ ID NO:2. More in particular, the invention provides polypeptides having the amino acid sequence of residues 2–410, 3–410, 4–410, 5–410, 6–410, 7–410, 8–410, 9–410, 10–410, 11–410, 12–410, 13–410, 14–410, 15–410, 16–410, 17–410, 18–410, 19–410, 20–410, 21–410, 22–4101, 23–410, 24–410, 25-410, 26–410, 27–410, 28–410, 29–410, 30–410, 31–410, 32–410, 33–410, 34–410, 35–410, 36–410, 37–410, 38–410, 39–410, 40–410, 41–410, 42–410, 43–410, 44–410, 45–410, 46–410, 47–410, 48–410 and 49–410 of SEQ ID NO: 2. Polynucleotides encoding these polypeptides also are provided.

More in particular, the invention provides polynucleotides encoding polypeptides comprising, or alternatively consisting of, the amino acid sequence of residues of: A-2 to L-410; F-3 to L-410; L-4 to L-410; G-5 to L-410; L-6 to L-410; F-7 to L-410; S-8 to L-410; L-9 to L-410; L-10 to L-410; V-11 to L-410; L-12 to L-410; Q-13 to L-410; S-14 to L-410; M-15 to L-410; A-16 to L-410; T-17 to L-410; G-18 to L-410; A-19 to L-410; T-20 to L-410; F-21 to L-410; P-22 to L-410; E-23 to L-410; E-24 to L-410; A-25 to L-410; I-26 to L-410; A-27 to L-410; D-28 to L-410; L-29 to L-410; S-30 to L-410; V-31 to L-410; N-32 to L-410; M-33 to L-410; Y-34 to L-410; N-35 to L-410; R-36 to L-410; L-37 to L-410; R-38 to L-410; A-39 to L-410; T-40 to L-410; G-41 to L-410; E-42 to L-410; D-43 to L-410; E-44 to L-410; N-45 to L-410; I-46 to L-410; L-47 to L-410; F-48 to L-410; S-49 to L-410; P-50 to L-410; L-51 to L-410; S-52 to L-410; I-53 to L-410; A-54 to L-410; L-55 to L-410; A-56 to L-410; M-57 to L-410; G-58 to L-410; M-59 to L-410; M-60 to L-410; E-61 to L-410; L-62 to L-410; G-63 to L-410; A-64 to L-410; Q-65 to L-410; G-66 to L-410; S-67 to L-410; T-68 to L-410; Q-69 to L-410; K-70 to L-410; E-71 to L-410; I-72 to L-410; R-73 to L-410; H-74 to L-410; S-75 to L-410; M-76 to L-410; G-77 to L-410; Y-78 to L-410; D-79 to L-410; S-80 to L-410; L-81 to L-410; K-82 to L-410; N-83 to L-410; G-84 to L-410; E-85 to L-410; E-86 to L-410; F-87 to L-410; S-88 to L-410; F-89 to L-410; L-90 to L-410; K-91 to L-410; E-92 to L-410; F-93 to L-410; S-94 to L-410; N-95 to L-410; M-96 to L-410; V-97 to L-410; T-98 to L-410; A-99 to L-410; K-100 to L-410; E-101 to L-410; S-102 to L-410; Q-103 to L-410; Y-104 to L-410; V-105 to L-410; M-106 to L-410; K-107 to L-410; I-108 to L-410; A-109 to L-410; N-110 to L-410; S-111 to L-410; L-112 to L-410; F-113 to L-410; V-114 to L-410; Q-115 to L-410; N-116 to L-410; G-117 to L-410; F-118 to L-410; H-119 to L-410; V-120 to L-410; N-121 to L-410; E-122 to L-410; E-123 to L-410; F-124 to L-410; L-125 to L-410; Q-126 to L-410; M-127 to L-410; M-128 to L-410; K-129 to L-410; K-130 to L-410; Y-131 to L-410; F-132 to L-410; N-133 to L-410; A-134 to L-410; A-135 to L-410; V-136 to L-410; N-137 to L-410; H-138 to L-410; V-139 to L-410; D-140 to L-410; F-141 to L-410; S-142 to L-410; Q-143 to L-410; N-144 to L-410; V-145 to L-410; A-146 to L-410; V-147 to L-410; A-148 to L-410; N-149 to L-410; Y-150 to L-410; I-151 to L-410; N-152 to L-410; K-153 to L-410; W-154 to L-410; V-155 to L-410; E-156 to L-410; N-157 to L-410; N-158 to L-410; T-159 to L-410; N-160 to L-410; N-161 to L-410; L-162 to L-410; V-163 to L-410; K-164 to L-410; D-165 to L-410; L-166 to L-410; V-167 to L-410; S-168 to L-410; P-169 to L-410; R-170 to L-410; D-171 to L-410; F-172 to L-410; D-173 to L-410; A-174 to L-410; A-175 to L-410; T-176 to L-410; Y-177 to L-410; L-178 to L-410; A-179 to L-410; L-180 to L-410; I-181 to L-410; N-182 to L-410; A-183 to L-410; V-184 to L-410; Y-185 to L-410; F-186 to L-410; K-187 to L-410; G-188 to L-410; N-189 to L-410; W-190 to L-410; K-191 to L-410; S-192 to L-410; Q-193 to L-410; F-194 to L-410; R-195 to L-410; P-196 to L-410; E-197 to L-410; N-198 to L-410; T-199 to L-410; R-200 to L-410; T-201 to L-410; F-202 to L-410; S-203 to L-410; F-204 to L-410; T-205 to L-410; K-206 to L-410; D-207 to L-410; D-208 to L-410; E-209 to L-410; S-210 to L-410; E-211 to L-410; V-212 to L-410; Q-213 to L-410; I-214 to L-410; P-215 to L-410; M-216 to L-410; M-217 to L-410; Y-218 to L-410; Q-219 to L-410; Q-220 to L-410; G-221 to L-410; E-222 to L-410; F-223 to L-410; Y-224 to L-410; Y-225 to L-410; G-226 to L-410; E-227 to L-410; F-228 to L-410; S-229 to L-410; D-230 to L-410; G-231 to L-410; S-232 to L-410; N-233 to L-410; E-234 to L-410; A-235 to L-410; G-236 to L-410; G-237 to L-410; I-238 to L-410; Y-239 to L-410; Q-240 to L-410; V-241 to L-410; L-242 to L-410; E-243 to L-410; I-244 to L-410; P-245 to L-410; Y-246 to L-410; E-247 to L-410; G-248 to L-410; D-249 to L-410; E-250 to L-410; I-251 to L-410; S-252 to L-410; M-253 to L-410; M-254 to L-410; L-255 to L-410; V-256 to L-410; L-257 to L-410; S-258 to L-410; R-259 to L-410; Q-260 to L-410; E-261 to L-410; V-262 to L-410; P-263 to L-410; L-264 to L-410; A-265 to L-410; T-266 to L-410; L-267 to L-410; E-268 to L-410; P-269 to L-410; L-270 to L-410; V-271 to L-410; K-272 to L-410; A-273 to L-410; Q-274 to L-410; L-275 to L-410; V-276 to L-410; E-277 to L-410; E-278 to L-410; W-279 to L-410; A-280 to L-410; N-281 to L-410; S-282 to L-410; V-283 to L-410; K-284 to L-410; K-285 to L-410; Q-286 to L-410; K-287 to L-410; V-288 to L-410; E-289 to L-410; V-290 to L-410; Y-291 to L-410; L-292 to L-410; P-293 to L-410; R-294 to L-410; F-295 to L-410; T-296 to L-410; V-297 to L-410; E-298 to L-410; Q-299 to L-410; E-300 to L-410; I-301 to L-410; D-302 to L-410; L-303 to L-410; K-304 to L-410; D-305 to L-410; V-306 to L-410; L-307 to L-410; K-308 to L-410; A-309 to L-410; L-310 to L-410; G-311 to L-410; I-312 to L-410; T-313 to L-410; E-314 to L-410; I-315 to L-410; F-316 to L-410; I-317 to L-410; K-318 to L-410; D-319 to L-410; A-320 to L-410; N-321 to L-410; L-322 to L-410; T-323 to L-410; G-324 to L-410; L-325 to L-410; S-326 to L-410; D-327 to L-410; N-328 to L-410; K-329 to L-410; E-330 to L-410; I-331 to L-410; F-332 to L-410; L-333 to L-410; S-334 to L-410; K-335 to L-410; A-336 to L-410; I-337 to L-410; H-338 to L-410; K-339 to L-410; S-340 to L-410; F-341 to L-410; L-342 to L-410; E-343 to L-410; V-344 to L-410; N-345 to L-410; E-346 to L-410; E-347 to L-410; G-348 to L-410; S-349 to L-410; E-350 to L-410; A-351 to L-410; A-352 to L-410; A-353 to L-410; V-354 to L-410; S-355 to L-410; G-356 to L-410; M-357 to L-410; I-358 to L-410; A-359 to L-410; I-360 to L-410; S-361 to L-410; R-362 to L-410; M-363 to L-410; A-364 to L-410; V-365 to L-410; L-366 to L-410; Y-367 to L-410; P-368 to L-410; Q-369 to L-410; V-370 to L-410; I-371 to L-410; V-372 to L-410; D-373 to L-410; H-374 to L-410; P-375 to L-410; F-376 to L-410; F-377 to L-410; F-378 to L-410; L-379 to L-410; I-380 to L-410; R-381 to L-410; N-382 to L-410; R-383 to L-410; R-384 to L-410; T-385 to L-410; G-386 to L-410; T-387 to L-410; I-388 to L-410; L-389 to L-410; F-390 to L-410; M-391 to L-410; G-392 to L-410; R-393 to L-410; V-394 to L-410; M-395 to L-410; H-396 to L-410; P-397 to L-410; E-398 to L-410; T-399 to L-410; M-400 to L-410; N-401 to L-410; T-402 to L-410; S-403 to L-410; G-404 to L-410; and/or H-405 to L-410 of SEQ ID NO: 2. Polynucleotides encoding these polypeptides are also encompassed by the invention.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the BAIT polypeptide described above. The present invention also encompasses the above polynucleotide sequences fused to a heterologous polynucleotide sequence.

Similarly, the present invention further provides polypeptides having one or more residues from the carboxyl terminus of the amino acid sequence of the complete BAIT polypeptide in SEQ ID NO: 2, up to 30 residues from the carboxyl terminus, and polynucleotides encoding such polypeptides. In particular, the present invention provides polypeptides having the amino acid sequence of residues 1-m of the amino acid sequence in SEQ ID NO: 2, where m is any integer in the range of 2–410, and preferably in the range of 381–409, as shown in the amino acid sequence in SEQ ID NO: 2. More in particular, the invention provides polypeptides having the amino acid sequence of residues 1-381, 1-382, 1383, 1-384, 1-385, 1-386, 1-387, etc. up to 1-408 of SEQ ID NO: 2. Polynucleotides encoding these polypeptides also are provided. In addition, polypeptides (and polynucleotides encoding these) having both N-terminal and C-terminal deletions together, of the general formula n-m of SEQ ID NO: 2 are included, where n and m are integers as defined above.

Even if deletion of one or more amino acids from the N-terminus and/or the C-terminus of a protein results in modification of loss of one or more biological functions of the protein, other functional activities (e.g., biological activities, ability to multimerize, ability to bind BAIT ligand) may still be retained. For example the ability of the shortened BAIT mutein to induce and/or bind to antibodies which recognize the complete or mature forms of the polypeptide generally will be retained when less than the majority of the residues of the complete or mature polypeptide are removed from the N-terminus and/or the C-terminus. Whether a particular polypeptide lacking N-terminus and/or C-terminal residues of a complete polypeptide retains such immunologic activities can readily be determined by routine methods described herein and otherwise known in the art. It is not unlikely that an BAIT mutein with a large number of deleted N-terminal and/or C-terminal amino acid residues may retain some biological or immunogenic activities. In fact, peptides composed of as few as six BAIT amino acid residues may often evoke an immune response.

More in particular, the invention provides polynucleotides encoding polypeptides comprising, or alternatively consisting of, the amino acid sequence of residues of: P-22 to E-409; P-22 to E-408; P-22 to F-407; P-22 to D-406; P-22 to H-405; P-22 to G-404; P-22 to S-403; P-22 to T-402; P-22 to N-401; P-22 to M-400; P-22 to T-399; P-22 to E-398; P-22 to P-397; P-22 to H-396; P-22 to M-395; P-22 to V-394; P-22 to R-393; P-22 to G-392; P-22 to M-391; P-22 to F-390; P-22 to L-389; P-22 to I-388; P-22 to T-387; P-22 to G-386; P-22 to T-385; P-22 to R-384; P-22 to R-383; P-22 to N-382; P-22 to R-381; P-22 to I-380; P-22 to L-379; P-22 to F-378; P-22 to F-377; P-22 to F-376; P-22 to P-375; P-22 to H-374; P-22 to D-373; P-22 to V-372; P-22 to I-371; P-22 to V-370; P-22 to Q-369; P-22 to P-368; P-22 to Y-367; P-22 to L-366; P-22 to V-365; P-22 to A-364; P-22 to M-363; P-22 to R-362; P-22 to S-361; P-22 to I-360; P-22 to A-359; P-22 to I-358; P-22 to M-357; P-22 to G-356; P-22 to S-355; P-22 to V-354; P-22 to A-353; P-22 to A-352; P-22 to A-351; P-22 to E-350; P-22 to S-349; P-22 to G-348; P-22 to E-347; P-22 to E-346; P-22 to N-345; P-22 to V-344; P-22 to E-343; P-22 to L-342; P-22 to F-341; P-22 to S-340; P-22 to K-339; P-22 to H-338; P-22 to I-337; P-22 to A-336; P-22 to K-335; P-22 to S-334; P-22 to L-333; P-22 to F-332; P-22 to I-331; P-22 to E-330; P-22 to K-329; P-22 to N-328; P-22 to D-327; P-22 to S-326; P-22 to L-325; P-22 to G-324; P-22 to T-323; P-22 to L-322; P-22 to N-321; P-22 to A-320; P-22 to D-319; P-22 to K-318; P-22 to L-317; P-22 to F-316; P-22 to I-315; P-22 to E-314; P-22 to T-313; P-22 to I-312; P-22 to G-311; P-22 to L-310; P-22 to A-309; P-22 to K-308; P-22 to L-307; P-22 to V-306; P-22 to D-305; P-22 to K-304; P-22 to L-303; P-22 to D-302; P-22 to I-301; P-22 to E-300; P-22 to Q-299; P-22 to E-298; P-22 to V-297; P-22 to T-296; P-22 to F-295; P-22 to R-294; P-22 to P-293; P-22 to L-292; P-22 to Y-291; P-22 to V-290; P-22 to E-289; P-22 to V-288; P-22 to K-287; P-22 to Q-286; P-22 to K-285; P-22 to K-284; P-22 to V-283; P-22 to S-282; P-22 to N-281; P-22 to A-280; P-22 to W-279; P-22 to E-278; P-22 to E-277; P-22 to V-276; P-22 to L-275; P-22 to Q-274; P-22 to A-273; P-22 to K-272; P-22 to V-271; P-22 to L-270; P-22 to P-269; P-22 to E-268; P-22 to L-267; P-22 to T-266; P-22 to A-265; P-22 to L-264; P-22 to P-263; P-22 to V-262; P-22 to E-261; P-22 to Q-260; P-22 to R-259; P-22 to S-258; P-22 to L-257; P-22 to V-256; P-22 to L-255; P-22 to M-254; P-22 to M-253; P-22 to S-252; P-22 to I-251; P-22 to E-250; P-22 to D-249; P-22 to G-248; P-22 to E-247; P-22 to Y-246; P-22 to P-245; P-22 to I-244; P-22 to E-243; P-22 to L-242; P-22 to V-241; P-22 to Q-240; P-22 to Y-239; P-22 to I-238; P-22 to G-237; P-22 to G-236; P-22 to A-235; P-22 to E-234; P-22 to N-233; P-22 to S-232; P-22 to G-231; P-22 to D-230; P-22 to S-229; P-22 to F-228; P-22 to E-227; P-22 to G-226; P-22 to Y-225; P-22 to Y-224; P-22 to F-223; P-22 to E-222; P-22 to G-221; P-22 to Q-220; P-22 to Q-219; P-22 to Y-218; P-22 to M-217; P-22 to M-216; P-22 to P-215; P-22 to I-214; P-22 to Q-213; P-22 to V-212; P-22 to E-211; P-22 to S-210; P-22 to E-209; P-22 to D-208; P-22 to D-207; P-22 to K-206; P-22 to T-205; P-22 to F-204; P-22 to S-203; P-22 to F-202; P-22 to T-201; P-22 to R-200; P-22 to T-199; P-22 to N-198; P-22 to E-197; P-22 to P-196; P-22 to R-195; P-22 to F-194; P-22 to Q-193; P-22 to S-192; P-22 to K-191; P-22 to W-190; P-22 to N-189; P-22 to G-188; P-22 to K-187; P-22 to F-186; P-22 to Y-185; P-22 to V-184; P-22 to A-183; P-22 to N-182; P-22 to I-181; P-22 to L-180; P-22 to A-179; P-22 to L-178; P-22 to Y-177; P-22 to T-176; P-22 to A-175; P-22 to A-174; P-22 to D-173; P-22 to F-172; P-22 to D-171; P-22 to R-170; P-22 to P-169; P-22 to S-168; P-22 to V-167; P-22 to L-166; P-22 to D-165; P-22 to K-164; P-22 to V-163; P-22 to L-162; P-22 to N-161; P-22 to N-160; P-22 to T-159; P-22 to N-158; P-22 to N-157; P-22 to E-156; P-22 to V-155; P-22 to W-154; P-22 to K-153; P-22 to N-152; P-22 to I-151; P-22 to Y-150; P-22 to N-149; P-22 to A-148; P-22 to V-147; P-22 to A-146; P-22 to V-145; P-22 to N-144; P-22 to Q-143; P-22 to S-142; P-22 to F-141; P-22 to D-140; P-22 to V-139; P-22 to H-138; P-22 to N-137; P-22 to V-136; P-22 to A-135; P-22 to A-134; P-22 to N-133; P-22 to F-132; P-22 to Y-131; P-22 to K-130; P-22 to K-129; P-22 to M-128; P-22 to M-127; P-22 to Q-126; P-22 to L-125; P-22 to F-124; P-22 to E-123; P-22 to E-122; P-22 to N-121; P-22 to V-120; P-22 to H-19; P-22 to F-118; P-22 to G-117; P-22 to N-116; P-22 to Q-115; P-22 to V-114; P-22 to F-113; P-22 to L-112; P-22 to S-111; P-22 to N-110; P-22 to A-109; P-22 to I-108; P-22 to K-107; P-22 to M-106; P-22 to V-105; P-22 to Y-104; P-22 to Q-103; P-22 to S-102; P-22 to E-101; P-22 to K-100; P-22 to A-99; P-22 to T-98; P-22 to V-97; P-22 to M-96; P-22 to N-95; P-22 to S-94; P-22 to F-93; P-22 to E-92; P-22 to K-91; P-22 to L-90; P-22 to F-89; P-22 to S-88; P-22 to F-87; P-22 to E-86; P-22 to E-85; P-22 to G-84; P-22 to N-83; P-22 to K-82; P-22 to L-81; P-22 to S-80; P-22 to D-79; P-22 to Y-78; P-22 to G-77; P-22 to M-76; P-22 to S-75; P-22 to H-74; P-22 to R-73; P-22 to I-72; P-22 to E-71; P-22 to K-70; P-22 to Q-69; P-22 to T-68; P-22 to S-67; P-22 to G-66; P-22 to Q-65; P-22 to A-64; P-22 to G-63; P-22 to L-62; P-22 to E-61; P-22 to M-60; P-22 to M-59; P-22 to G-58; P-22 to M-57; P-22 to A-56; P-22 to L-55; P-22 to A-54; P-22 to I-53; P-22 to S-52; P-22 to L-51; P-22 to P-50; P-22 to S-49; P-22 to F-48; P-22 to L-47; P-22 to I-46; P-22 to N-45; P-22 to E-44; P-22 to D-43; P-22 to E-42; P-22 to G-41; P-22 to T-40; P-22 to A-39; P-22 to R-38; P-22 to L-37; P-22 to R-36; P-22 to N-35; P-22 to Y-34; P-22 to M-33; P-22 to N-32; P-22 to V-31; P-22 to S-30; P-22 to L-29; and/or P-22 to D-28 of SEQ ID NO: 2. Polynucleotides encoding these polypeptides are also encompassed by the invention.

Moreover, a signal sequence may be added to these C-terminal contructs. For example, amino acids 1–21 of SEQ ID NO:2, amino acids 2–21 of SEQ ID NO:2, amino acids 3–21 of SEQ ID NO:2, amino acids 4–21 of SEQ ID NO:2, amino acids 5–21 of SEQ ID NO:2, amino acids 6–21 of SEQ ID NO:2, amino acids 7–21 of SEQ ID NO:2, amino acids 8–21 of SEQ ID NO:2, amino acids 9–21 of SEQ ID NO:2, amino acids 10–21 of SEQ ID NO:2, amino acids 11–21 of SEQ ID NO:2, amino acids 12–21 of SEQ ID NO:2, amino acids 13–21 of SEQ ID NO:2, amino acids 14–21 of SEQ ID NO:2, amino acids 15–21 of SEQ ID NO:2, amino acids 16–21 of SEQ ID NO:2, amino acids 17–21 of SEQ ID NO:2, amino acids 18–21 of SEQ ID NO:2, amino acids 19–21 of SEQ ID NO:2, amino acids 20–21 of SEQ ID NO:2, and/or amino acids 21 of SEQ ID NO:2 can be added to the N-terminus of each C-terminal constructs listed above. Additionally, a methioine can be added to these constructs.

The present application is also directed to nucleic acid molecules comprising, or alternatively, consisting of, a polynucleotide sequence at least 90%, 92%, 95%, 96%, 97%, 98%, or 99% identical to the polynucleotide sequence encoding the BAIT polypeptide described above. The present invention also encompasses the above polynucleotide sequences fused to a heterologous polynucleotide sequence. In addition, any of the above listed N- or C-terminal deletions can be combined to produce a N- and C-terminal deleted BAIT polypeptide. The invention also provides polypeptides having one or more amino acids deleted from both the amino and the carboxyl termini, which may be described generally as having residues m–n of SEQ ID NO:2, where n and m are integers as described above. Polynucleotides encoding these polypeptides are also encompassed by the invention.

Also included are a nucleotide sequence encoding a polypeptide consisting of a portion of the complete BAIT amino acid sequence encoded by the cDNA clone contained in ATCC™ Deposit No. 97722, where this portion excludes any integer of amino acid residues from 1 to about 400 amino acids from the amino terminus of the complete amino acid sequence encoded by the cDNA clone contained in ATCC™ Deposit No. 97722, or any integer of amino acid residues from 1 to about 400 amino acids from the carboxy terminus, or any combination of the above amino terminal and carboxy terminal deletions, of the complete amino acid sequence encoded by the cDNA clone contained in ATCC™ Deposit No. 97722. Polynucleotides encoding all of the above deletion mutant polypeptide forms also are provided.

The present application is also directed to proteins containing polypeptides at least 90%, 92%, 93%, 94%, 95%, 96%, 97%, 98% or 99% identical to the polypeptide sequence set forth herein m–n. In preferred embodiments, the application is directed to proteins containing polypeptides at least 90%, 95%, 96%, 97%, 98% or 99% identical to polypeptides having the amino acid sequence of the specific BAIT N- and C-terminal deletions recited herein. Polynucleotides encoding these polypeptides are also encompassed by the invention.

As indicated, nucleic acid molecules of the present invention may be in the form of RNA, such as mRNA, are in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at positions 89–91 of the nucleotide sequence shown in FIGS. 1A–1B (SEQ ID NO:1); DNA molecules comprising the coding sequence for the mature BAIT protein shown in FIGS. 1A–1B (amino acids 19–410) (SEQ ID NO:2); and DNA molecules which comprise a sequence substantially different from those described above but which, due to the degeneracy of the genetic code, still encode the BAIT protein. Of course, the genetic code is well known in the art. Thus, it would be routine for one skilled in the art to generate the degenerate variants described above.

In another aspect, the invention provides isolated nucleic acid molecules encoding the BAIT polypeptide having an amino acid sequence encoded by the cDNA clone contained in the plasmid deposited as ATCC™ Deposit No. 97722. Preferably, this nucleic acid molecule will encode the mature polypeptide encoded by the above-described deposited cDNA clone. The invention further provides an isolated nucleic acid molecule having the nucleotide sequence shown in FIGS. 1A–1B (SEQ ID NO:1) or the nucleotide sequence of the BAIT cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the BAIT gene in human tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of SEQ ID NO:1 which consists of positions 1–410 of SEQ ID NO:1. In addition, the invention provides nucleic acid molecules having related nucleotide sequences determined from the following related cDNA clones: HPBCT06R (SEQ ID NO:7), HBPDG64R (SEQ ID NO: 8), and HPBCR79R (SEQ ID NO: 9); see FIGS. 4A–4G. More generally, by a fragment of an isolated nucleic acid molecule having the nucleotide sequence of the deposited cDNA or the nucleotide sequence shown in FIGS. 1A–1B (SEQ ID NO: 1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIGS. 1A–1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A–1B (SEQ ID NO:1). Since the gene has been deposited and the nucleotide sequence shown in FIGS. 1A–1B (SEQ ID NO:1) is provided, generating such DNA fragments would be routine to the skilled artisan. For example, restriction endonuclease cleavage or shearing by sonication could easily be used to generate fragments of various sizes. Alternatively, such fragments could be generated synthetically.

Preferred nucleic acid fragments of the present invention include nucleic acid molecules encoding epitope-bearing portions of the BAIT polypeptide as identified in FIG. 3 and described in more detail below.

In another aspect, the invention provides an isolated nucleic acid molecule comprising a polynucleotide which hybridizes under stringent hybridization conditions, to a portion of the polynucleotide in a nucleic acid molecule of the invention described above, for instance, the cDNA clone contained in ATCC™ Deposit 97722. By "stringent hybridization conditions" is intended overnight incubation at 42 C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 g/ml denatured, sheared salmon sperm DNA, followed by washing the filters in 0.1× SSC at about 65 C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 50–70 nt of the reference polynucleotide. These are useful as diagnostic probes and primers as discussed above and in more detail below.

Of course, polynucleotides hybridizing to a larger portion of the reference polynucleotide (e.g., the deposited cDNA clone), for instance, a portion 50–300 nt in length, or even to the entire length of the reference polynucleotide, are also useful as probes according to the present invention, as are polynucleotides corresponding to most, if not all, of the nucleotide sequence of the deposited cDNA or the nucleotide sequence as shown in FIGS. 1A–1B (SEQ ID NO:1). By a portion of a polynucleotides "at least 20 nt in length," for example, is intended 20 or more contiguous nucleotides from the nucleotide sequence of the reference polynucleotide (e.g., the deposited cDNA or the nucleotide sequence as shown in FIGS. 1A–1B (SEQ ID NO:1)). As indicated, such portions are useful diagnostically either as a probe according to conventional DNA hybridization techniques or as primers for amplification of a target sequence by the polymerase chain reaction (PCR), as described, for instance, in *Molecular Cloning, A Laboratory Manual,* 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a BAIT cDNA clone has been deposited and its determined nucleotide sequence is provided in FIGS. 1A–1B (SEQ ID NO:1), generating polynucleotides which hybridize to a portion of the BAIT cDNA molecule would be routine to the skilled artisan. For example, restriction endonuclease cleavage or shearing by sonication of the BAIT cDNA clone could easily be used to generate DNA portions of various sizes which are polynucleotides that hybridize to a portion of the BAIT cDNA molecule. Alternatively, the hybridizing polynucleotides of the present invention could be generated synthetically according to known techniques. Of course, a polynucleotide which hybridizes only to a poly A sequence (such as the 3 terminal poly(A) tract of the BAIT cDNA shown in FIGS. 1A–1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a BAIT polypeptide may include, but are not limited to those encoding the amino acid sequence of the mature polypeptide, by itself; the coding sequence for the mature polypeptide and additional sequences, such as those encoding the about 18 amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexahistidine peptide, such as the tag provided in a pQE vector (QIAGEN, Inc.), among others, many of which are commercially available. As described in Gentz et al., *Proc. Natl. Acad. Sci. USA* 86:821–824 (1989), for instance, hexahistidine provides for convenient purification of the fusion protein. The "HA" tag is another peptide useful for purification which corresponds to an epitope derived from the influenza hemagglutinin protein, which has been described by Wilson et al., Cell 37:767 (1984). As discussed below, other such fusion proteins include the BAIT fused to Fc at the N- or C-terminus.

The present invention further relates to variants of the nucleic acid molecules of the present invention, which encode portions, analogs or derivatives of the BAIT protein. Variants may occur naturally, such as a natural allelic variant. By an "allelic variant" is intended one of several alternate forms of a gene occupying a given locus on a chromosome of an organism. *GenesIII*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the BAIT protein or portions thereof. Also especially preferred in this regard are conservative substitutions. Most highly preferred are nucleic acid molecules encoding the mature protein having the amino acid sequence shown in FIGS. 1A–1B (SEQ ID NO:2) or the mature BAIT amino acid sequence encoded by the deposited cDNA clone.

Further embodiments of the invention include isolated nucleic acid molecules comprising a polynucleotide having a nucleotide sequence at least 99% identical, and more preferably at least 99.1% 99.9% identical to (a) a nucleotide sequence encoding the full-length BAIT polypeptide having the complete amino acid sequence in FIGS. 1A–1B (SEQ ID NO:2), including the leader sequence; (b) a nucleotide sequence encoding the mature BAIT polypeptide (full-length polypeptide with the leader removed) having the amino acid sequence at positions 19–94 in FIGS. 1A–1B (SEQ ID NO:2); (c) a nucleotide sequence encoding the full-length BAIT polypeptide having the complete amino acid sequence including the leader encoded by the cDNA clone contained in ATCC™ Deposit No. 97722; (d) a nucleotide sequence encoding the mature BAIT polypeptide having the amino acid sequence encoded by the cDNA clone contained in ATCC™ Deposit No. 97722; or (e) a nucleotide sequence complementary to any of the nucleotide sequences in (a), (b), (c) or (d).

By a polynucleotide having a nucleotide sequence at least, for example, 99% "identical" to a reference nucleotide sequence encoding a BAIT polypeptide is intended that the nucleotide sequence of the polynucleotide is identical to the reference sequence except that the polynucleotide sequence may include up to one point mutations per each 100 nucleotides of the reference nucleotide sequence encoding the BAIT polypeptide. In other words, to obtain a polynucleotide having a nucleotide sequence at least 99% identical to a reference nucleotide sequence, up to 1% of the nucleotides in the reference sequence may be deleted or substituted with another nucleotide, or a number of nucleotides up to 1% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 99.1%, to 99.9% identical to, for instance, the nucleotide sequence shown in FIGS. 1A–1B or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Watennan, *Advances in Applied Mathematics* 2:482–489 (1981), to find the best segment of homology between two sequences. When using Bestfit or any other sequence alignment program to determine whether a particular sequence is, for instance, 99% identical to a reference sequence according to the present invention, the parameters are set, of course, such that the percentage of identity is calculated over the full length of the reference nucleotide sequence and that gaps in homology of up to 1% of the total number of nucleotides in the reference sequence are allowed.

The present application is directed to nucleic acid molecules at least 96%, 96.1%, 96.2%, 96.3% to 99.9% identical to the nucleic acid sequence shown in FIGS. 1A–1B (SEQ ID NO:1) or to the nucleic acid sequence of the deposited cDNA, irrespective of whether they encode a polypeptide having BAIT activity. This is because even where a particular nucleic acid molecule does not encode a polypeptide having BAIT activity, one of skill in the art would still know how to use the nucleic acid molecule, for instance, as a hybridization probe or a polymerase chain reaction (PCR) primer. Uses of the nucleic acid molecules of the present invention that do not encode a polypeptide having BAIT activity include, inter alia, (1) isolating the BAIT gene or allelic variants thereof in a cDNA library; (2) in situ hybridization (e.g., "FISH") to metaphase chromosomal spreads to provide precise chromosomal location of the BAIT gene, as described in Verma et al., Human Chromosomes: A Manual of Basic Techniques, Pergamon Press, New York (1988); and Northern Blot analysis for detecting BAIT mRNA expression in specific tissues.

Preferred, however, are nucleic acid molecules having sequences at least 99%, to 99.9% identical to the nucleic acid sequence shown in FIGS. 1A–1B (SEQ ID NO:1) or to the nucleic acid sequence of the deposited cDNA which do, in fact, encode a polypeptide having BAIT protein activity. By "a polypeptide having BAIT activity" is intended polypeptides exhibiting activity similar, but not necessarily identical, to an activity of the BAIT protein of the invention (either the full-length protein or, preferably, the mature protein), as measured in a particular biological assay. For example, the BAIT protein of the present invention inhibits the proteolytic activity of tissue-type plasminogen activator (t-PA). Briefly, the assay involves measuring the inhibitory activity against various proteases, particularly tPA, using a single step chromogenic assay essentially as described (Lawrence, D. A., et. al. (1990) The Journal of Biological Chemistry, 265, 20293–20301).

BAIT protein inhibits proteolytic activity of t-PA in a dose-dependent manner in the above-described assay. Thus, "a polypeptide having BAIT protein activity" includes polypeptides that also exhibit any of the same t-PA-inhibiting activities in the above-described assay in a dose-dependent manner. Although the degree of dose dependent activity need not be identical to that of the BAIT protein, preferably, "a polypeptide having BAIT protein activity" will exhibit substantially similar dose dependence in a given activity as compared to the BAIT protein (i.e., the candidate polypeptide will exhibit greater activity or not more than about 25-fold less and, preferably, not more than about tenfold less activity relative to the reference BAIT protein).

Of course, due to the degeneracy of the genetic code, one of ordinary skill in the art will immediately recognize that a large number of the nucleic acid molecules having a sequence at least 99% identical to the nucleic acid sequence of the deposited cDNA or the nucleic acid sequence shown in FIGS. 1A–1B (SEQ ID NO:1) will encode a polypeptide "having BAIT protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having BAIT protein activity. This is because the skilled artisan is fully aware of amino acid substitutions that are either less likely or not likely to significantly effect protein function (e.g., replacing one aliphatic amino acid with a second aliphatic amino acid), as further described below.

BAIT Polypeptides and Fragments

The invention further provides an isolated BAIT polypeptide having the amino acid sequence encoded by the deposited cDNA, or the amino acid sequence in FIGS. 1A–1B (SEQ ID NO:2), or a peptide or polypeptide comprising a portion of the above polypeptides. The terms "peptide" and "oligopeptide" are considered synonymous (as is commonly recognized)—and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

In addition to mature and N-terminal deletion forms of the protein discussed above, it will be recognized by one of ordinary skill in the art that some amino acid sequences of the BAIT polypeptide can be varied without significant effect of the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the BAIT polypeptide which show substantial BAIT polypeptide activity or which include regions of BAIT protein such as the protein portions discussed below. Such mutants include deletions, insertions, inversions, repeats, and type substitutions selected according to general rules known in the art so as have little effect on activity.

For example, guidance concerning how to make phenotypically silent amino acid substitutions is provided in Bowie et al., "Deciphering the Message in Protein Sequences: Tolerance to Amino Acid Substitutions," Science 247:1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA, the nucleic acid sequence shown in FIGS. 1A–1B (SEQ ID NO:1), or fragments thereof, will encode polypeptides "having BAIT functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having BAIT functional activity. This is because the skilled artisan is fully aware of amino acid substitutions that are either less likely or not likely to significantly effect protein function (e.g., replacing one aliphatic amino acid with a second aliphatic amino acid), as further described below.

For example, site directed changes at the amino acid level of BAIT can be made by replacing a particular amino acid with a conservative amino acid. Preferred conservative mutations include: M1 replaced with A, G, I, L, S, T, or V; A2 replaced with G, I, L, S, T, M, or V; F3 replaced with W, or Y; L4 replaced with A, G, I, S, T, M, or V; G5 replaced with A, I, L, S, T, M, or V; L6 replaced with A, G, I, S, T, M, or V; F7 replaced with W, or Y; S8 replaced with A, G, I, L, T, M, or V; L9 replaced with A, G, I, S, T, M, or V; L10 replaced with A, G, I, S, T, M, or V; V11 replaced with A, G, I, L, S, T, or M; L12 replaced with A, G, I, S, T, M, or V; Q13 replaced with N; S14 replaced with A, G, I, L, T, M, or V; M15 replaced with A, G, I, L, S, T, or V; A16 replaced with G, I, L, S, T, M, or V; T17 replaced with A, G, I, L, S, M, or V; G18 replaced with A, I, L, S, T, M, or V; A19 replaced with G, I, L, S, T, M, or V; T20 replaced with A, G, I, L, S, M, or V; F21 replaced with W, or Y; E23 replaced with D; E24 replaced with D; A25 replaced with G, I, L, S, T, M, or V; I26 replaced with A, G, L, S, T, M, or V; A27 replaced with G, I, L, S, T, M, or V; D28 replaced with E; L29 replaced with A, G, I, S, T, M, or V; S30 replaced with A, G, I, L, T, M, or V; V31 replaced with A, G, I, L, S, T, or M; N32 replaced with Q; M33 replaced with A, G, I, L, S, T, or V; Y34 replaced with F, or W; N35 replaced with Q; R36 replaced with H, or K; L37 replaced with A, G, I, S, T, M, or V; R38 replaced with H, or K; A39 replaced with G, I, L, S, T, M, or V; T40 replaced with A, G, I, L, S, M, or V; G41 replaced with A, I, L, S, T, M, or V; E42 replaced with D; D43 replaced with E; E44 replaced with D; N45 replaced with Q; I46 replaced with A, G, L, S, T, M, or V; L47 replaced with A, G, I, S, T, M, or V; F48 replaced with W, or Y; S49 replaced with A, G, I, L, T, M, or V; L51 replaced with A, G, I, S, T, M, or V; S52 replaced with A, G, I, L, T, M, or V; I53 replaced with A, G, L, S, T, M, or V; A54 replaced with G, I, L, S, T, M, or V; L55 replaced with A, G, I, S, T, M, or V; A56 replaced with G, I, L, S, T, M, or V; M57 replaced with A, G, I, L, S, T, or V; G58 replaced with A, I, L, S, T, M, or V; M59 replaced with A, G, I, L, S, T, or V; M60 replaced with A, G, I, L, S, T, or V; E61 replaced with D; L62 replaced with A, G, I, S, T, M, or V; G63 replaced with A, I, L, S, T, M, or V; A64 replaced with G, I, L, S, T, M, or V; Q65 replaced with N; G66 replaced with A, I, L, S, T, M, or V; S67 replaced with A, G, I, L, T, M, or V; T68 replaced with A, G, I, L, S, M, or V; Q69 replaced with N; K70 replaced with H, or R; E71 replaced with D; I72 replaced with A, G, L, S, T, M, or V; R73 replaced with H, or K; H74 replaced with K, or R; S75 replaced with A, G, I, L, T, M, or V; M76 replaced with A, G, I, L, S, T, or V; G77 replaced with A, I, L, S, T, M, or V; Y78 replaced with F, or W; D79 replaced with E; S80 replaced with A, G, I, L, T, M, or V; L81 replaced with A, G, I, S, T, M, or V; K82 replaced with H, or R; N83 replaced with Q; G84 replaced with A, I, L, S, T, M, or V; E85 replaced with D; E86 replaced with D; F87 replaced with W, or Y; S88 replaced with A, G, I, L, T, M, or V; F89 replaced with W, or Y; L90 replaced with A, G, I, S, T, M, or V; K91 replaced with H, or R; E92 replaced with D; F93 replaced with W, or Y; S94 replaced with A, G, I, L, T, M, or V; N95 replaced with Q; M96 replaced with A, G, I, L, S, T, or V; V97 replaced with A, G, I, L, S, T, or M; T98 replaced with A, G, I, L, S, M, or V; A99 replaced with G, I, L, S, T, M, or V; K100 replaced with H, or R; E101 replaced with D; S102 replaced with A, G, I, L, T, M, or V; Q103 replaced with N; Y104 replaced with F, or W; V105 replaced with A, G, I, L, S, T, or M; M106 replaced with A, G, I, L, S, T, or V; K107 replaced with H, or R; 1108 replaced with A, G, L, S, T, M, or V; A109 replaced with G, I, L, S, T, M, or V; N110 replaced with Q; S111 replaced with A, G, I, L, T, M, or V; L112 replaced with A, G, I, S, T, M, or V; F113 replaced with W, or Y; V114 replaced with A, G, I, L, S, T, or M; Q115 replaced with N; N116 replaced with Q; G117 replaced with A, I, L, S, T, M, or V; F118 replaced with W, or Y; H119 replaced with K, or R; V120 replaced with A, G, I, L, S, T, or M; N121 replaced with Q; E122 replaced with D; E123 replaced with D; F124 replaced with W, or Y; L125 replaced with A, G, I, S, T, M, or V; Q126 replaced with N; M127 replaced with A, G, I, L, S, T, or V; M128 replaced with A, G, I, L, S, T, or V; K129 replaced with H, or R; K130 replaced with H, or R; Y131 replaced with F, or W; F132 replaced with W, or Y; N133 replaced with Q; A134 replaced with G, I, L, S, T, M, or V; A135 replaced with G, I, L, S, T, M, or V; V136 replaced with A, G, I, L, S, T, or M; N137 replaced with Q; H138 replaced with K, or R; V139 replaced with A, G, I, L, S, T, or M; D140 replaced with E; F141 replaced with W, or Y; S142 replaced with A, G, I, L, T, M, or V; Q143 replaced with N; N144 replaced with Q; V145 replaced with A, G, I, L, S, T, or M; A146 replaced with G, I, L, S, T, M, or V; V147 replaced with A, G, I, L, S, T, or M; A148 replaced with G, I, L, S, T, M, or V; N149 replaced with Q; Y150 replaced with F, or W; I151 replaced with A, G, L, S, T, M, or V; N152 replaced with Q; K153 replaced with H, or R; W154 replaced with F, or Y; V155 replaced with A, G, I, L, S, T, or M; E156 replaced with D; N157 replaced with Q; N158 replaced with Q; T159 replaced with A, G, I, L, S, M, or V; N160 replaced with Q; N161 replaced with Q; L162 replaced with A, G, I, S, T, M, or V; V163 replaced with A, G, I, L, S, T, or M; K164 replaced with H, or R; D165 replaced with E; L166 replaced with A, G, I, S, T, M, or V; V167 replaced with A, G, I, L, S, T, or M; S168 replaced with A, G, I, L, T, M, or V; R170 replaced with H, or K; D171 replaced with E; F172 replaced with W, or Y; D173 replaced with E; A174 replaced with G, I, L, S, T, M, or V; A175 replaced with G, I, L, S, T, M, or V; T176 replaced with A, G, I, L, S, M, or V; Y177 replaced with F, or W; L178 replaced with A, G, I, S, T, M, or V; A179 replaced with G, I, L, S, T, M, or V; L180 replaced with A, G, I, S, T, M, or V; 1181 replaced with A, G, L, S, T, M, or V; N182 replaced with Q; A183 replaced with G, I, L, S, T, M, or V; V184 replaced with A, G, I, L, S, T, or M; Y185 replaced with F, or W; F186 replaced with W, or Y; K187 replaced with H, or R; G188 replaced with A, I, L, S, T, M, or V; N189 replaced with Q; W190 replaced with F, or Y; K191 replaced with H, or R; S192 replaced with A, G, I, L, T, M, or V; Q193 replaced with N; F194 replaced with W, or Y; R195 replaced with H, or K; E197 replaced with D; N198 replaced with Q; T199 replaced with A, G, I, L, S, M, or V; R200 replaced with H, or K; T201 replaced with A, G, I, L, S, M, or V; F202 replaced with W, or Y; S203 replaced with A, G, I, L, T, M, or V; F204 replaced with W, or Y; T205 replaced with A, G, I, L, S, M, or V; K206 replaced with H, or R; D207 replaced with E; D208 replaced with E; E209 replaced with D; S210 replaced with A, G, I, L, T, M, or V; E211 replaced with D; V212 replaced with A, G, I, L, S, T, or M; Q213 replaced with N; I214 replaced with A, G, L, S, T, M, or V; M216 replaced with A, G, I, L, S, T, or V; M217 replaced with A, G, I, L, S, T, or V; Y218 replaced with F, or W; Q219 replaced with N; Q220 replaced with N; G221 replaced with A, I, L, S, T, M, or V; E222 replaced with D; F223 replaced with W, or Y; Y224 replaced with F, or W; Y225 replaced with F, or W; G226 replaced with A, I, L, S, T, M, or V; E227 replaced with D; F228 replaced with W, or Y; S229 replaced with A, G, I, L, T, M, or V; D230 replaced with E; G231 replaced with A, I, L, S, T, M, or V; S232 replaced with A, G, I, L, T, M, or V; N233 replaced with Q; E234 replaced with D; A235 replaced with G, I, L, S, T, M, or V; G236 replaced with A, I, L, S, T, M, or V; G237 replaced with A, I, L, S, T, M, or V; I238 replaced with A, G, L, S, T, M, or V; Y239 replaced with F, or W; Q240 replaced with N; V241 replaced with A, G, I, L, S, T, or M; L242 replaced with A, G, I, S, T, M, or V; E243 replaced with D; I244 replaced with A, G, L, S, T, M, or V; Y246 replaced with F, or W; E247 replaced with D; G248 replaced with A, I, L, S, T, M, or V; D249 replaced with E; E250 replaced with D; I251 replaced with A, G, L, S, T, M, or V; S252 replaced with A, G, I, L, T, M, or V; M253 replaced with A, G, I, L, S, T, or V; M254 replaced with A, G, I, L, S, T, or V; L255 replaced with A, G, I, S, T, M, or V; V256 replaced with A, G, I, L, S, T, or M; L257 replaced with A, G, I, S, T, M, or V; S258 replaced with A, G, I, L, T, M, or V; R259 replaced with H, or K; Q260 replaced with N; E261 replaced with D; V262 replaced with A, G, I, L, S, T, or M; L264 replaced with A, G, I, S, T, M, or V; A265 replaced with G, I, L, S, T, M, or V; T266 replaced with A, G, I, L, S, M, or V; L267 replaced with A, G, I, S, T, M, or V; E268 replaced with D; L270 replaced with A, G, I, S, T, M, or V; V271 replaced with A, G, I, L, S, T, or M; K272 replaced with H, or R; A273 replaced with G, I, L, S, T, M, or V; Q274 replaced with N; L275 replaced with A, G, I, S, T, M, or V; V276 replaced with A, G, I, L, S, T, or M; E277 replaced with D; E278 replaced with D; W279 replaced with F, or Y; A280 replaced with G, I, L, S, T, M, or V; N281 replaced with Q; S282 replaced with A, G, I, L, T, M, or V; V283 replaced with A, G, I, L, S, T, or M; K284 replaced with H, or R; K285 replaced with H, or R; Q286 replaced with N; K287 replaced with H, or R; V288 replaced with A, G, I, L, S, T, or M; E289 replaced with D; V290 replaced with A, G, I, L, S, T, or M; Y291 replaced with F, or W; L292 replaced with A, G, I, S, T, M, or V; R294 replaced with H, or K; F295 replaced with W, or Y; T296 replaced with A, G, I, L, S, M, or V; V297 replaced with A, G, I, L, S, T, or M; E298 replaced with D; Q299 replaced with N; E300 replaced with D; I301 replaced with A, G, L, S, T, M, or V; D302 replaced with E; L303 replaced with A, G, I, S, T, M, or V; K304 replaced with H, or R; D305 replaced with E; V306 replaced with A, G, I, L, S, T, or M; L307 replaced with A, G, I, S, T, M, or V; K308 replaced with H, or R; A309 replaced with G, I, L, S, T, M, or V; L310 replaced with A, G, I, S, T, M, or V; G311 replaced with A, I, L, S, T, M, or V; 1312 replaced with A, G, L, S, T, M, or V; T313 replaced with A, G, I, L, S, M, or V; E314 replaced with D; I315 replaced with A, G, L, S, T, M, or V; F316 replaced with W, or Y; 1317 replaced with A, G, L, S, T, M, or V; K318 replaced with H, or R; D319 replaced with E; A320 replaced with G, I, L, S, T, M, or V; N321 replaced with Q; L322 replaced with A, G, I, S, T, M, or V; T323 replaced with A, G, I, L, S, M, or V; G324 replaced with A, I, L, S, T, M, or V; L325 replaced with A, G, I, S, T, M, or V; S326 replaced with A, G, I, L, T, M, or V; D327 replaced with E; N328 replaced with Q; K329 replaced with H, or R; E330 replaced with D; I331 replaced with A, G, L, S, T, M, or V; F332 replaced with W, or Y; L333 replaced with A, G, I, S, T, M, or V; S334 replaced with A, G, I, L, T, M, or V; K335 replaced with H, or R; A336 replaced with G, I, L, S, T, M, or V; I337 replaced with A, G, L, S, T, M, or V; H338 replaced with K, or R; K339 replaced with H, or R; S340 replaced with A, G, I, L, T, M, or V; F341 replaced with W, or Y; L342 replaced with A, G, I, S, T, M, or V; E343 replaced with D; V344 replaced with A, G, I, L, S, T, or M; N345 replaced with Q; E346 replaced with D; E347 replaced with D; G348 replaced with A, I, L, S, T, M, or V; S349 replaced with A, G, I, L, T, M, or V; E350 replaced with D; A351 replaced with G, I, L, S, T, M, or V; A352 replaced with G, I, L, S, T, M, or V; A353 replaced with G, I, L, S, T, M, or V; V354 replaced with A, G, I, L, S, T, or M; S355 replaced with A, G, I, L, T, M, or V; G356 replaced with A, I, L, S, T, M, or V; M357 replaced with A, G, I, L, S, T, or V; I358 replaced with A, G, L, S, T, M, or V; A359 replaced with G, I, L, S, T, M, or V; I360 replaced with A, G, L, S, T, M, or V; S361 replaced with A, G, I, L, T, M, or V; R362 replaced with H, or K; M363 replaced with A, G, I, L, S, T, or V; A364 replaced with G, I, L, S, T, M, or V; V365 replaced with A, G, I, L, S, T, or M; L366 replaced with A, G, I, S, T, M, or V; Y367 replaced with F, or W; Q369 replaced with N; V370 replaced with A, G, I, L, S, T, or M; I371 replaced with A, G, L, S, T, M, or V; V372 replaced with A, G, I, L, S, T, or M; D373 replaced with E; H374 replaced with K, or R; F376 replaced with W, or Y; F377 replaced with W, or Y; F378 replaced with W, or Y; L379 replaced with A, G, I, S, T, M, or V; I380 replaced with A, G, L, S, T, M, or V; R381 replaced with H, or K; N382 replaced with Q; R383 replaced with H, or K; R384 replaced with H, or K; T385 replaced with A, G, I, L, S, M, or V; G386 replaced with A, I, L, S, T, M, or V; T387 replaced with A, G, I, L, S, M, or V; I388 replaced with A, G, L, S, T, M, or V; L389 replaced with A, G, I, S, T, M, or V; F390 replaced with W, or Y; M391 replaced with A, G, I, L, S, T, or V; G392 replaced with A, I, L, S, T, M, or V; R393 replaced with H, or K; V394 replaced with A, G, I, L, S, T, or M; M395 replaced with A, G, I, L, S, T, or V; H396 replaced with K, or R; E398 replaced with D; T399 replaced with A, G, I, L, S, M, or V; M400 replaced with A, G, I, L, S, T, or V; N401 replaced with Q; T402 replaced with A, G, I, L, S, M, or V; S403 replaced with A, G, I, L, T, M, or V; G404 replaced with A, I, L, S, T, M, or V; H405 replaced with K, or R; D406 replaced with E; F407 replaced with W, or Y; E408 replaced with D; E409 replaced with D; and/or L410 replaced with A, G, I, S, T, M, or V of SEQ ID NO:2.

The resulting constructs can be routinely screened for activities or functions described throughout the specification and known in the art. Preferably, the resulting constructs have an increased and/or a decreased BAIT activity or function, while the remaining BAIT activities or functions are maintained. More preferably, the resulting constructs have more than one increased and/or decreased BAIT activity or function, while the remaining BAIT activities or functions are maintained.

Besides conservative amino acid substitution, variants of BAIT include (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polye0thylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, BAIT polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

For example, preferred non-conservative substitutions of BAIT include: M1 replaced with D, E, H, K, R, N, Q, F, W, Y, P, or C; A2 replaced with D, E, H, K, R, N, Q, F, W, Y, P, or C; F3 replaced with D, E, H, K, R, N, Q, A, G, I, L, S, T, M, V, P, or C; L4 replaced with D, E, H, K, R, N, Q, F, W, Y, P, or C; G5 replaced with D, E, H, K, R, N, Q, F, W, Y, P, or C; L6 replaced with D, E, H, K, R, N, Q, F, W, Y, P, or C; F7 replaced with D, E, H, K, R, N, Q, A, G, I, L, S, T, M, V, P, or C; S8 replaced with D, E, H, K, R, N, Q, F, W, Y, P, or C; L9 replaced with D, E, H, K, R, N, Q, F, W, Y, P, or C; L10 replaced with D, E, H, K, R, N, Q, F, W, Y, P, or C; V11 replaced with D, E, H, K, R, N, Q, F, W, Y, P, or C; L12 replaced with D, E, H, K, R, N, Q, F, W, Y, P, or C; Q13 replaced with D, E, H, K, R, A, G, I, L, S, T, M, V, F, W, Y, P, or C; S14 replaced with D, E, H, K, R, N, Q, F, W, Y, P, or C; M15 replaced with D, E, H, K, R, N, Q, F, W, Y, P, or C; A16 replaced with D, E, H, K, R, N, Q, F, W, Y, P, or C; T17 replaced with D, E, H, K, R, N, Q, F, W, Y, P, or C; G18 replaced with D, E, H, K, R, N, Q, F, W, Y, P, or C; A19 replaced with D, E, H, K, R, N, Q, F, W, Y, P, or C; T20 replaced with D, E, H, K, R, N, Q, F, W, Y, P, or C; F21 replaced with D, E, H, K, R, N, Q, A, G, I, L, S, T, M, V, P, or C; P22 replaced with D, E, H, K, R, A, G, I, L, S, T, M, V, N, Q, F, W, Y, or C; E23 replaced with H, K, R, A, G, I, L, S, T, M, V, N, Q, F, W, Y, P, or C; E24 replaced with H, K, R, A, G, I, L, S, T, M, V, N, Q, F, W, Y, P, or C; A25 replaced with D, E, H, K, R, N, Q, F, W, Y, P, or C; I26 replaced with D, E, H, K, R, N, Q, F, W, Y, P, or C; A27 replaced with D, E, H, K, R, N, Q, F, W, Y, P, or C; D28 replaced with H, K, R, A, G, I, L, S, T, M, V, N, Q, F, W, Y, P, or C; L29 replaced with D, E, H, K, R, N, Q, F, W, Y, P, or C; S30 replaced with D, E, H, K, R, N, Q, F, W, Y, P, or C; V31 replaced with D, E, H, K, R, N, Q, F, W, Y, P, or C; N32 replaced with D, E, H, K, R, A, G, I, L, S, T, M, V, F, W, Y, P, or C; M33 replaced with D, E, H, K, R, N, Q, F, W, Y, P, or C; Y34 replaced with D, E, H, K, R, N, Q, A, G, I, L, S, T, M, V, P, or C; N35 replaced with D, E, H, K, R, A, G, I, L, S, T, M, V, F, W, Y, P, or C; R36 replaced with D, E, A, G, I, L, S, T, M, V, N, Q, F, W, Y, P, or C; L37 replaced with D, E, H, K, R, N, Q, F, W, Y, P, or C; R38 replaced with D, E, A, G, I, L, S, T, M, V, N, Q, F, W, Y, P, or C; A39 replaced with D, E, H, K, R, N, Q, F, W, Y, P, or C; T40 replaced with D, E, H, K, R, N, Q, F, W, Y, P, or C; G41 replaced with D, E, H, K, R, N, Q, F, W, Y, P, or C; E42 replaced with H, K, R, A, G, I, L, S, T, M, V, N, Q, F, W, Y, P, or C; D43 replaced with H, K, R, A, G, I, L, S, T, M, V, N, Q, F, W, Y, P, or C; E44 replaced with H, K, R, A, G, I, L, S, T, M, V, N, Q, F, W, Y, P, or C; N45 replaced with D, E, H, K, R, A, G, I, L, S, T, M, V, F, W, Y, P, or C; I46 replaced with D, E, H, K, R, N, Q, F, W, Y, P, or C; L47 replaced with D, E, H, K, R, N, Q, F, W, Y, P, or C; F48 replaced with D, E, H, K, R, N, Q, A, G, I, L, S, T, M, V, P, or C; S49 replaced with D, E, H, K, R, N, Q, F, W, Y, P, or C; P50 replaced with D, E, H, K, R, A, G, I, L, S, T, M, V, N, Q, F, W, Y, or C; L51 replaced with D, E, H, K, R, N, Q, F, W, Y, P, or C; S52 replaced with D, E, H, K, R, N, Q, F, W, Y, P, or C; I53 replaced with D, E, H, K, R, N, Q, F, W, Y, P, or C; A54 replaced with D, E, H, K, R, N, Q, F, W, Y, P, or C; L55 replaced with D, E, H, K, R, N, Q, F, W, Y, P, or C; A56 replaced with D, E, H, K, R, N, Q, F, W, Y, P, or C; M57 replaced with D, E, H, K, R, N, Q, F, W, Y, P, or C; G58 replaced with D, E, H, K, R, N, Q, F, W, Y, P, or C; M59 replaced with D, E, H, K, R, N, Q, F, W, Y, P, or C; M60 replaced with D, E, H, K, R, N, Q, F, W, Y, P, or C; E61 replaced with H, K, R, A, G, I, L, S, T, M, V, N, Q, F, W, Y, P, or C; L62 replaced with D, E, H, K, R, N, Q, F, W, Y, P, or C; G63 replaced with D, E, H, K, R, N, Q, F, W, Y, P, or C; A64 replaced with D, E, H, K, R, N, Q, F, W, Y, P, or C; Q65 replaced with D, E, H, K, R, A, G, I, L, S, T, M, V, F, W, Y, P, or C; G66 replaced with D, E, H, K, R, N, Q, F, W, Y, P, or C; S67 replaced with D, E, H, K, R, N, Q, F, W, Y, P, or C; T68 replaced with D, E, H, K, R, N, Q, F, W, Y, P, or C; Q69 replaced with D, E, H, K, R, A, G, I, L, S, T, M, V, F, W, Y, P, or C; K70 replaced with D, E, A, G, I, L, S, T, M, V, N, Q, F, W, Y, P, or C; E71 replaced with H, K, R, A, G, I, L, S, T, M, V, N, Q, F, W, Y, P, or C; I72 replaced with D, E, H, K, R, N, Q, F, W, Y, P, or C; R73 replaced with D, E, A, G, I, L, S, T, M, V, N, Q, F, W, Y, P, or C; H74 replaced with D, E, A, G, I, L, S, T, M, V, N, Q, F, W, Y, P, or C; S75 replaced with D, E, H, K, R, N, Q, F, W, Y, P, or C; M76 replaced with D, E, H, K, R, N, Q, F, W, Y, P, or C; G77 replaced with D, E, H, K, R, N, Q, F, W, Y, P, or C; Y78 replaced with D, E, H, K, R, N, Q, A, G, I, L, S, T, M, V, P, or C; D79 replaced with H, K, R, A, G, I, L, S, T, M, V, N, Q, F, W, Y, P, or C; S80 replaced with D, E, H, K, R, N, Q, F, W, Y, P, or C; L81 replaced with D, E, H, K, R, N, Q, F, W, Y, P, or C; K82 replaced with D, E, A, G, I, L, S, T, M, V, N, Q, F, W, Y, P, or C; N83 replaced with D, E, H, K, R, A, G, I, L, S, T, M, V, F, W, Y, P, or C; G84 replaced with D, E, H, K, R, N, Q, F, W, Y, P, or C; E85 replaced with H, K, R, A, G, I, L, S, T, M, V, N, Q, F, W, Y, P, or C; E86 replaced with H, K, R, A, G, I, L, S, T, M, V, N, Q, F, W, Y, P, or C; F87 replaced with D, E, H, K, R, N, Q, A, G, I, L, S, T, M, V, P, or C; S88 replaced with D, E, H, K, R, N, Q, F, W, Y, P, or C; F89 replaced with D, E, H, K, R, N, Q, A, G, I, L, S, T, M, V, P, or C; L90 replaced with D, E, H, K, R, N, Q, F, W, Y, P, or C; K91 replaced with D, E, A, G, I, L, S, T, M, V, N, Q, F, W, Y, P, or C; E92 replaced with H, K, R, A, G, I, L, S, T, M, V, N, Q, F, W, Y, P, or C; F93 replaced with D, E, H, K, R, N, Q, A, G, I, L, S, T, M, V, P, or C; S94 replaced with D, E, H, K, R, N, Q, F, W, Y, P, or C; N95 replaced with D, E, H, K, R, A, G, I, L, S, T, M, V, F, W, Y, P, or C; M96 replaced with D, E, H, K, R, N, Q, F, W, Y, P, or C; V97 replaced with D, E, H, K, R, N, Q, F, W, Y, P, or C; T98 replaced with D, E, H, K, R, N, Q, F, W, Y, P, or C; A99 replaced with D, E, H, K, R, N, Q, F, W, Y, P, or C; K100 replaced with D, E, A, G, I, L, S, T, M, V, N, Q, F, W, Y, P, or C; E101 replaced with H, K, R, A, G, I, L, S, T, M, V, N, Q, F, W, Y, P, or C; S102 replaced with D, E, H, K, R, N, Q, F, W, Y, P, or C; Q103 replaced with D, E, H, K, R, A, G, I, L, S, T, M, V, F, W, Y, P, or C; Y104 replaced with D, E, H, K, R, N, Q, A, G, I, L, S, T, M, V, P, or C; V105 replaced with D, E, H, K, R, N, Q, F, W, Y, P, or C; M106 replaced with D, E, H, K, R, N, Q, F, W, Y, P, or C; K107 replaced with D, E, A, G, I, L, S, T, M, V, N, Q, F, W, Y, P, or C; I108 replaced with D, E, H, K, R, N, Q, F, W, Y, P, or C; A109 replaced with D, E, H, K, R, N, Q, F, W, Y, P, or C; N110 replaced with D, E, H, K, R, A, G, I, L, S, T, M, V, F, W, Y, P, or C; S111 replaced with D, E, H, K, R, N, Q, F, W, Y, P, or C; L112 replaced with D, E, H, K, R, N, Q, F, W, Y, P, or C; F113 replaced with D, E, H, K, R, N, Q, A, G, I, L, S, T, M, V, P, or C; V114 replaced with D, E, H, K, R, N, Q, F, W, Y, P, or C; Q115 replaced with D, E, H, K, R, A, G, I, L, S, T, M, V, F, W, Y, P, or C; N116 replaced with D, E, H, K, R, A, G, I, L, S, T, M, V, F, W, Y, P, or C; G117 replaced with D, E, H, K, R, N, Q, F, W, Y, P, or C; F118 replaced with D, E, H, K, R, N, Q, A, G, I, L, S, T, M, V, P, or C; H119 replaced with D, E, A, G, I, L, S, T, M, V, N, Q, F, W, Y, P, or C; V120 replaced with D, E, H, K, R, N, Q, F, W, Y, P, or C; N121 replaced with D, E, H, K, R, A, G, I, L, S, T, M, V, F, W, Y, P, or C; E122 replaced with H, K, R, A, G, I, L, S, T, M, V, N, Q, F, W, Y, P, or C; E123 replaced with H, K, R, A, G, I, L, S, T, M, V, N, Q, F, W, Y, P, or C; F124 replaced with D, E, H, K, R, N, Q, A, G, I, L, S, T, M, V, P, or C; L125 replaced with D, E, H, K, R, N, Q, F, W, Y, P, or C; Q126 replaced with D, E, H, K, R, A, G, I, L, S, T, M, V, F, W, Y, P, or C; M127 replaced with D, E, H, K, R, N, Q, F, W, Y, P, or C; M128 replaced with D, E, H, K, R, N, Q, F, W, Y, P, or C; K129 replaced with D, E, A, G, I, L, S, T, M, V, N, Q, F, W, Y, P, or C; K130 replaced with D, E, A, G, I, L, S, T, M, V, N, Q, F, W, Y, P, or C; Y131 replaced with D, E, H, K, R, N, Q, A, G, I, L, S, T, M, V, P, or C; F132 replaced with D, E, H, K, R, N, Q, A, G, I, L, S, T, M, V, P, or C; N133 replaced with D, E, H, K, R, A, G, I, L, S, T, M, V, F, W, Y, P, or C; A134 replaced with D, E, H, K, R, N, Q, F, W, Y, P, or C; A135 replaced with D, E, H, K, R, N, Q, F, W, Y, P, or C; V136 replaced with D, E, H, K, R, N, Q, F, W, Y, P, or C; N137 replaced with D, E, H, K, R, A, G, I, L, S, T, M, V, F, W, Y, P, or C; H138 replaced with D, E, A, G, I, L, S, T, M, V, N, Q, F, W, Y, P, or C; V139 replaced with D, E, H, K, R, N, Q, F, W, Y, P, or C; D140 replaced with H, K, R, A, G, I, L, S, T, M, V, N, Q, F, W, Y, P, or C; F141 replaced with D, E, H, K, R, N, Q, A, G, I, L, S, T, M, V, P, or C; S142 replaced with D, E, H, K, R, N, Q, F, W, Y, P, or C; Q143 replaced with D, E, H, K, R, A, G, I, L, S, T, M, V, F, W, Y, P, or C; N144 replaced with D, E, H, K, R, A, G, I, L, S, T, M, V, F, W, Y, P, or C; V145 replaced with D, E, H, K, R, N, Q, F, W, Y, P, or C; A146 replaced with D, E, H, K, R, N, Q, F, W, Y, P, or C; V147 replaced with D, E, H, K, R, N, Q, F, W, Y, P, or C; A148 replaced with D, E, H, K, R, N, Q, F, W, Y, P, or C; N149 replaced with D, E, H, K, R, A, G, I, L, S, T, M, V, F, W, Y, P, or C; Y150 replaced with D, E, H, K, R, N, Q, A, G, I, L, S, T, M, V, P, or C; I151 replaced with D, E, H, K, R, N, Q, F, W, Y, P, or C; N152 replaced with D, E, H, K, R, A, G, I, L, S, T, M, V, F, W, Y, P, or C; K153 replaced with D, E, A, G, I, L, S, T, M, V, N, Q, F, W, Y, P, or C; W154 replaced with D, E, H, K, R, N, Q, A, G, I, L, S, T, M, V, P, or C; V155 replaced with D, E, H, K, R, N, Q, F, W, Y, P, or C; E156 replaced with H, K, R, A, G, I, L, S, T, M, V, N, Q, F, W, Y, P, or C; N157 replaced with D, E, H, K, R, A, G, I, L, S, T, M, V, F, W, Y, P, or C; N158 replaced with D, E, H, K, R, A, G, I, L, S, T, M, V, F, W, Y, P, or C; T159 replaced with D, E, H, K, R, N, Q, F, W, Y, P, or C; N160 replaced with D, E, H, K, R, A, G, I, L, S, T, M, V, F, W, Y, P, or C; N161 replaced with D, E, H, K, R, A, G, I, L, S, T, M, V, F, W, Y, P, or C; L162 replaced with D, E, H, K, R, N, Q, F, W, Y, P, or C; V163 replaced with D, E, H, K, R, N, Q, F, W, Y, P, or C; K164 replaced with D, E, A, G, I, L, S, T, M, V, N, Q, F, W, Y, P, or C; D165 replaced with H, K, R, A, G, I, L, S, T, M, V, N, Q, F, W, Y, P, or C; L166 replaced with D, E, H, K, R, N, Q, F, W, Y, P, or C; V167 replaced with D, E, H, K, R, N, Q, F, W, Y, P, or C; S168 replaced with D, E, H, K, R, N, Q, F, W, Y, P, or C; P169 replaced with D, E, H, K, R, A, G, I, L, S, T, M, V, N, Q, F, W, Y, or C; R170 replaced with D, E, A, G, I, L, S, T, M, V, N, Q, F, W, Y, P, or C; D171 replaced with H, K, R, A, G, I, L, S, T, M, V, N, Q, F, W, Y, P, or C; F172 replaced with D, E, H, K, R, N, Q, A, G, I, L, S, T, M, V, P, or C; D173 replaced with H, K, R, A, G, I, L, S, T, M, V, N, Q, F, W, Y, P, or C; A174 replaced with D, E, H, K, R, N, Q, F, W, Y, P, or C; A175 replaced with D, E, H, K, R, N, Q, F, W, Y, P, or C; T176 replaced with D, E, H, K, R, N, Q, F, W, Y, P, or C; Y177 replaced with D, E, H, K, R, N, Q, A, G, I, L, S, T, M, V, P, or C; L178 replaced with D, E, H, K, R, N, Q, F, W, Y, P, or C; A179 replaced with D, E, H, K, R, N, Q, F, W, Y, P, or C; L180 replaced with D, E, H, K, R, N, Q, F, W, Y, P, or C; I181 replaced with D, E, H, K, R, N, Q, F, W, Y, P, or C; N182 replaced with D, E, H, K, R, A, G, I, L, S, T, M, V, F, W, Y, P, or C; A183 replaced with D, E, H, K, R, N, Q, F, W, Y, P, or C; V184 replaced with D, E, H, K, R, N, Q, F, W, Y, P, or C; Y185 replaced with D, E, H, K, R, N, Q, A, G, I, L, S, T, M, V, P, or C; F186 replaced with D, E, H, K, R, N, Q, A, G, I, L, S, T, M, V, P, or C; K187 replaced with D, E, A, G, I, L, S, T, M, V, N, Q, F, W, Y, P, or C; G188 replaced with D, E, H, K, R, N, Q, F, W, Y, P, or C; N189 replaced with D, E, H, K, R, A, G, I, L, S, T, M, V, F, W, Y, P, or C; W190 replaced with D, E, H, K, R, N, Q, A, G, I, L, S, T, M, V, P, or C; K191 replaced with D, E, A, G, I, L, S, T, M, V, N, Q, F, W, Y, P, or C; S192 replaced with D, E, H, K, R, N, Q, F, W, Y, P, or C; Q193 replaced with D, E, H, K, R, A, G, I, L, S, T, M, V, F, W, Y, P, or C; F194 replaced with D, E, H, K, R, N, Q, A, G, I, L, S, T, M, V, P, or C; R195 replaced with D, E, A, G, I, L, S, T, M, V, N, Q, F, W, Y, P, or C; P196 replaced with D, E, H, K, R, A, G, I, L, S, T, M, V, N, Q, F, W, Y, or C; E197 replaced with H, K, R, A, G, I, L, S, T, M, V, N, Q, F, W, Y, P, or C; N198 replaced with D, E, H, K, R, A, G, I, L, S, T, M, V, F, W, Y, P, or C; T199 replaced with D, E, H, K, R, N, Q, F, W, Y, P, or C; R200 replaced with D, E, A, G, I, L, S, T, M, V, N, Q, F, W, Y, P, or C; T201 replaced with D, E, H, K, R, N, Q, F, W, Y, P, or C; F202 replaced with D, E, H, K, R, N, Q, A, G, I, L, S, T, M, V, P, or C; S203 replaced with D, E, H, K, R, N, Q, F, W, Y, P, or C; F204 replaced with D, E, H, K, R, N, Q, A, G, I, L, S, T, M, V, P, or C; T205 replaced with D, E, H, K, R, N, Q, F, W, Y, P, or C; K206 replaced with D, E, A, G, I, L, S, T, M, V, N, Q, F, W, Y, P, or C; D207 replaced with H, K, R, A, G, I, L, S, T, M, V, N, Q, F, W, Y, P, or C; D208 replaced with H, K, R, A, G, I, L, S, T, M, V, N, Q, F, W, Y, P, or C; E209 replaced with H, K, R, A, G, I, L, S, T, M, V, N, Q, F, W, Y, P, or C; S210 replaced with D, E, H, K, R, N, Q, F, W, Y, P, or C; E211 replaced with H, K, R, A, G, I, L, S, T, M, V, N, Q, F, W, Y, P, or C; V212 replaced with D, E, H, K, R, N, Q, F, W, Y, P, or C; Q213 replaced with D, E, H, K, R, A, G, I, L, S, T, M, V, F, W, Y, P, or C; I214 replaced with D, E, H, K, R, N, Q, F, W, Y, P, or C; P215 replaced with D, E, H, K, R, A, G, I, L, S, T, M, V, N, Q, F, W, Y, or C; M216 replaced with D, E, H, K, R, N, Q, F, W, Y, P, or C; M217 replaced with D, E, H, K, R, N, Q, F, W, Y, P, or C; Y218 replaced with D, E, H, K, R, N, Q, A, G, I, L, S, T, M, V, P, or C; Q219 replaced with D, E, H, K, R, A, G, I, L, S, T, M, V, F, W, Y, P, or C; Q220 replaced with D, E, H, K, R, A, G, I, L, S, T, M, V, F, W, Y, P, or C; G221 replaced with D, E, H, K, R, N, Q, F, W, Y, P, or C; E222 replaced with H, K, R, A, G, I, L, S, T, M, V, N, Q, F, W, Y, P, or C; F223 replaced with D, E, H, K, R, N, Q, A, G, I, L, S, T, M, V, P, or C; Y224 replaced with D, E, H, K, R, N, Q, A, G, I, L, S, T, M, V, P, or C; Y225 replaced with D, E, H, K, R, N, Q, A, G, I, L, S, T, M, V, P, or C; G226 replaced with D, E, H, K, R, N, Q, F, W, Y, P, or C; E227 replaced with H, K, R, A, G, I, L, S, T, M, V, N, Q, F, W, Y, P, or C; F228 replaced with D, E, H, K, R, N, Q, A, G, I, L, S, T, M, V, P, or C; S229 replaced with D, E, H, K, R, N, Q, F, W, Y, P, or C; D230 replaced with H, K, R, A, G, I, L, S, T, M, V, N, Q, F, W, Y, P, or C; G231 replaced with D, E, H, K, R, N, Q, F, W, Y, P, or C; S232 replaced with D, E, H, K, R, N, Q, F, W, Y, P, or C; N233 replaced with D, E, H, K, R, A, G, I, L, S, T, M, V, F, W, Y, P, or C; E234 replaced with H, K, R, A, G, I, L, S, T, M, V, N, Q, F, W, Y, P, or C; A235 replaced with D, E, H, K, R, N, Q, F, W, Y, P, or C; G236 replaced with D, E, H, K, R, N, Q, F, W, Y, P, or C; G237 replaced with D, E, H, K, R, N, Q, F, W, Y, P, or C; I238 replaced with D, E, H, K, R, N, Q, F, W, Y, P, or C; Y239 replaced with D, E, H, K, R, N, Q, A, G, I, L, S, T, M, V, P, or C; Q240 replaced with D, E, H, K, R, A, G, I, L, S, T, M, V, F, W, Y, P, or C; V241 replaced with D, E, H, K, R, N, Q, F, W, Y, P, or C; L242 replaced with D, E, H, K, R, N, Q, F, W, Y, P, or C; E243 replaced with H, K, R, A, G, I, L, S, T, M, V, N, Q, F, W, Y, P, or C; I244 replaced with D, E, H, K, R, N, Q, F, W, Y, P, or C; P245 replaced with D, E, H, K, R, A, G, I, L, S, T, M, V, N, Q, F, W, Y, or C; Y246 replaced with D, E, H, K, R, N, Q, A, G, I, L, S, T, M, V, P, or C; E247 replaced with H, K, R, A, G, I, L, S, T, M, V, N, Q, F, W, Y, P, or C; G248 replaced with D, E, H, K, R, N, Q, F, W, Y, P, or C; D249 replaced with H, K, R, A, G, I, L, S, T, M, V, N, Q, F, W, Y, P, or C; E250 replaced with H, K, R, A, G, I, L, S, T, M, V, N, Q, F, W, Y, P, or C; I125 replaced with D, E, H, K, R, N, Q, F, W, Y, P, or C; S252 replaced with D, E, H, K, R, N, Q, F, W, Y, P, or C; M253 replaced with D, E, H, K, R, N, Q, F, W, Y, P, or C; M254 replaced with D, E, H, K, R, N, Q, F, W, Y, P, or C; L255 replaced with D, E, H, K, R, N, Q, F, W, Y, P, or C; V256 replaced with D, E, H, K, R, N, Q, F, W, Y, P, or C; L257 replaced with D, E, H, K, R, N, Q, F, W, Y, P, or C; S258 replaced with D, E, H, K, R, N, Q, F, W, Y, P, or C; R259 replaced with D, E, A, G, I, L, S, T, M, V, N, Q, F, W, Y, P, or C; Q260 replaced with D, E, H, K, R, A, G, I, L, S, T, M, V, F, W, Y, P, or C; E261 replaced with H, K, R, A, G, I, L, S, T, M, V, N, Q, F, W, Y, P, or C; V262 replaced with D, E, H, K, R, N, Q, F, W, Y, P, or C; P263 replaced with D, E, H, K, R, A, G, I, L, S, T, M, V, N, Q, F, W, Y, or C; L264 replaced with D, E, H, K, R, N, Q, F, W, Y, P, or C; A265 replaced with D, E, H, K, R, N, Q, F, W, Y, P, or C; T266 replaced with D, E, H, K, R, N, Q, F, W, Y, P, or C; L267 replaced with D, E, H, K, R, N, Q, F, W, Y, P, or C; E268 replaced with H, K, R, A, G, I, L, S, T, M, V, N, Q, F, W, Y, P, or C; P269 replaced with D, E, H, K, R, A, G, I, L, S, T, M, V, N, Q, F, W, Y, or C; L270 replaced with D, E, H, K, R, N, Q, F, W, Y, P, or C; V271 replaced with D, E, H, K, R, N, Q, F, W, Y, P, or C; K272 replaced with D, E, A, G, I, L, S, T, M, V, N, Q, F, W, Y, P, or C; A273 replaced with D, E, H, K, R, N, Q, F, W, Y, P, or C; Q274 replaced with D, E, H, K, R, A, G, I, L, S, T, M, V, F, W, Y, P, or C; L275 replaced with D, E, H, K, R, N, Q, F, W, Y, P, or C; V276 replaced with D, E, H, K, R, N, Q, F, W, Y, P, or C; E277 replaced with H, K, R, A, G, I, L, S, T, M, V, N, Q, F, W, Y, P, or C; E278 replaced with H, K, R, A, G, I, L, S, T, M, V, N, Q, F, W, Y, P, or C; W279 replaced with D, E, H, K, R, N, Q, A, G, I, L, S, T, M, V, P, or C; A280 replaced with D, E, H, K, R, N, Q, F, W, Y, P, or C; N281 replaced with D, E, H, K, R, A, G, I, L, S, T, M, V, F, W, Y, P, or C; S282 replaced with D, E, H, K, R, N, Q, F, W, Y, P, or C; V283 replaced with D, E, H, K, R, N, Q, F, W, Y, P, or C; K284 replaced with D, E, A, G, I, L, S, T, M, V, N, Q, F, W, Y, P, or C; K285 replaced with D, E, A, G, I, L, S, T, M, V, N, Q, F, W, Y, P, or C; Q286 replaced with D, E, H, K, R, A, G, I, L, S, T, M, V, F, W, Y, P, or C; K287 replaced with D, E, A, G, I, L, S, T, M, V, N, Q, F, W, Y, P, or C; V288 replaced with D, E, H, K, R, N, Q, F, W, Y, P, or C; E289 replaced with H, K, R, A, G, I, L, S, T, M, V, N, Q, F, W, Y, P, or C; V290 replaced with D, E, H, K, R, N, Q, F, W, Y, P, or C; Y291 replaced with D, E, H, K, R, N, Q, A, G, I, L, S, T, M, V, P, or C; L292 replaced with D, E, H, K, R, N, Q, F, W, Y, P, or C; P293 replaced with D, E, H, K, R, A, G, I, L, S, T, M, V, N, Q, F, W, Y, or C; R294 replaced with D, E, A, G, I, L, S, T, M, V, N, Q, F, W, Y, P, or C; F295 replaced with D, E, H, K, R, N, Q, A, G, I, L, S, T, M, V, P, or C; T296 replaced with D, E, H, K, R, N, Q, F, W, Y, P, or C; V297 replaced with D, E, H, K, R, N, Q, F, W, Y, P, or C; E298 replaced with H, K, R, A, G, I, L, S, T, M, V, N, Q, F, W, Y, P, or C; Q299 replaced with D, E, H, K, R, A, G, I, L, S, T, M, V, F, W, Y, P, or C; E300 replaced with H, K, R, A, G, I, L, S, T, M, V, N, Q, F, W, Y, P, or C; I301 replaced with D, E, H, K, R, N, Q, F, W, Y, P, or C; D302 replaced with H, K, R, A, G, I, L, S, T, M, V, N, Q, F, W, Y, P, or C; L303 replaced with D, E, H, K, R, N, Q, F, W, Y, P, or C; K304 replaced with D, E, A, G, I, L, S, T, M, V, N, Q, F, W, Y, P, or C; D305 replaced with H, K, R, A, G, I, L, S, T, M, V, N, Q, F, W, Y, P, or C; V306 replaced with D, E, H, K, R, N, Q, F, W, Y, P, or C; L307 replaced with D, E, H, K, R, N, Q, F, W, Y, P, or C; K308 replaced with D, E, A, G, I, L, S, T, M, V, N, Q, F, W, Y, P, or C; A309 replaced with D, E, H, K, R, N, Q, F, W, Y, P, or C; L310 replaced with D, E, H, K, R, N, Q, F, W, Y, P, or C; G311 replaced with D, E, H, K, R, N, Q, F, W, Y, P, or C; I312 replaced with D, E, H, K, R, N, Q, F, W, Y, P, or C; T313 replaced with D, E, H, K, R, N, Q, F, W, Y, P, or C; E314 replaced with H, K, R, A, G, I, L, S, T, M, V, N, Q, F, W, Y, P, or C; I315 replaced with D, E, H, K, R, N, Q, F, W, Y, P, or C; F316 replaced with D, E, H, K, R, N, Q, A, G, I, L, S, T, M, V, P, or C; I317 replaced with D, E, H, K, R, N, Q, F, W, Y, P, or C; K318 replaced with D, E, A, G, I, L, S, T, M, V, N, Q, F, W, Y, P, or C; D319 replaced with H, K, R, A, G, I, L, S, T, M, V, N, Q, F, W, Y, P, or C; A320 replaced with D, E, H, K, R, N, Q, F, W, Y, P, or C; N321 replaced with D, E, H, K, R, A, G, I, L, S, T, M, V, F, W, Y, P, or C; L322 replaced with D, E, H, K, R, N, Q, F, W, Y, P, or C; T323 replaced with D, E, H, K, R, N, Q, F, W, Y, P, or C; G324 replaced with D, E, H, K, R, N, Q, F, W, Y, P, or C; L325 replaced with D, E, H, K, R, N, Q, F, W, Y, P, or C; S326 replaced with D, E, H, K, R, N, Q, F, W, Y, P, or C; D327 replaced with H, K, R, A, G, I, L, S, T, M, V, N, Q, F, W, Y, P, or C; N328 replaced with D, E, H, K, R, A, G, I, L, S, T, M, V, F, W, Y, P, or C; K329 replaced with D, E, A, G, I, L, S, T, M, V, N, Q, F, W, Y, P, or C; E330 replaced with H, K, R, A, G, I, L, S, T, M, V, N, Q, F, W, Y, P, or C; I331 replaced with D, E, H, K, R, N, Q, F, W, Y, P, or C; F332 replaced with D, E, H, K, R, N, Q, A, G, I, L, S, T, M, V, P, or C; L333 replaced with D, E, H, K, R, N, Q, F, W, Y, P, or C; S334 replaced with D, E, H, K, R, N, Q, F, W, Y, P, or C; K335 replaced with D, E, A, G, I, L, S, T, M, V, N, Q, F, W, Y, P, or C; A336 replaced with D, E, H, K, R, N, Q, F, W, Y, P, or C; I337 replaced with D, E, H, K, R, N, Q, F, W, Y, P, or C; H338 replaced with D, E, A, G, I, L, S, T, M, V, N, Q, F, W, Y, P, or C; K339 replaced with D, E, A, G, I, L, S, T, M, V, N, Q, F, W, Y, P, or C; S340 replaced with D, E, H, K, R, N, Q, F, W, Y, P, or C; F341 replaced with D, E, H, K, R, N, Q, A, G, I, L, S, T, M, V, P, or C; L342 replaced with D, E, H, K, R, N, Q, F, W, Y, P, or C; E343 replaced with H, K, R, A, G, I, L, S, T, M, V, N, Q, F, W, Y, P, or C; V344 replaced with D, E, H, K, R, N, Q, F, W, Y, P, or C; N345 replaced with D, E, H, K, R, A, G, I, L, S, T, M, V, F, W, Y, P, or C; E346 replaced with H, K, R, A, G, I, L, S, T, M, V, N, Q, F, W, Y, P, or C; E347 replaced with H, K, R, A, G, I, L, S, T, M, V, N, Q, F, W, Y, P, or C; G348 replaced with D, E, H, K, R, N, Q, F, W, Y, P, or C; S349 replaced with D, E, H, K, R, N, Q, F, W, Y, P, or C; E350 replaced with H, K, R, A, G, I, L, S, T, M, V, N, Q, F, W, Y, P, or C; A351 replaced with D, E, H, K, R, N, Q, F, W, Y, P, or C; A352 replaced with D, E, H, K, R, N, Q, F, W, Y, P, or C; A353 replaced with D, E, H, K, R, N, Q, F, W, Y, P, or C; V354 replaced with D, E, H, K, R, N, Q, F, W, Y, P, or C; S355 replaced with D, E, H, K, R, N, Q, F, W, Y, P, or C; G356 replaced with D, E, H, K, R, N, Q, F, W, Y, P, or C; M357 replaced with D, E, H, K, R, N, Q, F, W, Y, P, or C; I358 replaced with D, E, H, K, R, N, Q, F, W, Y, P, or C; A359 replaced with D, E, H, K, R, N, Q, F, W, Y, P, or C; I360 replaced with D, E, H, K, R, N, Q, F, W, Y, P, or C; S361 replaced with D, E, H, K, R, N, Q, F, W, Y, P, or C; R362 replaced with D, E, A, G, I, L, S, T, M, V, N, Q, F, W, Y, P, or C; M363 replaced with D, E, H, K, R, N, Q, F, W, Y, P, or C; A364 replaced with D, E, H, K, R, N, Q, F, W, Y, P, or C; V365 replaced with D, E, H, K, R, N, Q, F, W, Y, P, or C; L366 replaced with D, E, H, K, R, N, Q, F, W, Y, P, or C; Y367 replaced with D, E, H, K, R, N, Q, A, G, I, L, S, T, M, V, P, or C; P368 replaced with D, E, H, K, R, A, G, I, L, S, T, M, V, N, Q, F, W, Y, or C; Q369 replaced with D, E, H, K, R, A, G, I, L, S, T, M, V, F, W, Y, P, or C; V370 replaced with D, E, H, K, R, N, Q, F, W, Y, P, or C; I371 replaced with D, E, H, K, R, N, Q, F, W, Y, P, or C; V372 replaced with D, E, H, K, R, N, Q, F, W, Y, P, or C; D373 replaced with H, K, R, A, G, I, L, S, T, M, V, N, Q, F, W, Y, P, or C; H374 replaced with D, E, A, G, I, L, S, T, M, V, N, Q, F, W, Y, P, or C; P375 replaced with D, E, H, K, R, A, G, I, L, S, T, M, V, N, Q, F, W, Y, or C; F376 replaced with D, E, H, K, R, N, Q, A, G, I, L, S, T, M, V, P, or C; F377 replaced with D, E, H, K, R, N, Q, A, G, I, L, S, T, M, V, P, or C; F378 replaced with D, E, H, K, R, N, Q, A, G, I, L, S, T, M, V, P, or C; L379 replaced with D, E, H, K, R, N, Q, F, W, Y, P, or C; I380 replaced with D, E, H, K, R, N, Q, F, W, Y, P, or C; R381 replaced with D, E, A, G, I, L, S, T, M, V, N, Q, F, W, Y, P, or C; N382 replaced with D, E, H, K, R, A, G, I, L, S, T, M, V, F, W, Y, P, or C; R383 replaced with D, E, A, G, I, L, S, T, M, V, N, Q, F, W, Y, P, or C; R384 replaced with D, E, A, G, I, L, S, T, M, V, N, Q, F, W, Y, P, or C; T385 replaced with D, E, H, K, R, N, Q, F, W, Y, P, or C; G386 replaced with D, E, H, K, R, N, Q, F, W, Y, P, or C; T387 replaced with D, E, H, K, R, N, Q, F, W, Y, P, or C; I388 replaced with D, E, H, K, R, N, Q, F, W, Y, P, or C; L389 replaced with D, E, H, K, R, N, Q, F, W, Y, P, or C; F390 replaced with D, E, H, K, R, N, Q, A, G, I, L, S, T, M, V, P, or C; M391 replaced with D, E, H, K, R, N, Q, F, W, Y, P, or C; G392 replaced with D, E, H, K, R, N, Q, F, W, Y, P, or C; R393 replaced with D, E, A, G, I, L, S, T, M, V, N, Q, F, W, Y, P, or C; V394 replaced with D, E, H, K, R, N, Q, F, W, Y, P, or C; M395 replaced with D, E, H, K, R, N, Q, F, W, Y, P, or C; H396 replaced with D, E, A, G, I, L, S, T, M, V, N, Q, F, W, Y, P, or C; P397 replaced with D, E, H, K, R, A, G, I, L, S, T, M, V, N, Q, F, W, Y, or C; E398 replaced with H, K, R, A, G, I, L, S, T, M, V, N, Q, F, W, Y, P, or C; T399 replaced with D, E, H, K, R, N, Q, F, W, Y, P, or C; M400 replaced with D, E, H, K, R, N, Q, F, W, Y, P, or C; N401 replaced with D, E, H, K, R, A, G, I, L, S, T, M, V, F, W, Y, P, or C; T402 replaced with D, E, H, K, R, N, Q, F, W, Y, P, or C; S403 replaced with D, E, H, K, R, N, Q, F, W, Y, P, or C; G404 replaced with D, E, H, K, R, N, Q, F, W, Y, P, or C; H405 replaced with D, E, A, G, I, L, S, T, M, V, N, Q, F, W, Y, P, or C; D406 replaced with H, K, R, A, G, I, L, S, T, M, V, N, Q, F, W, Y, P, or C; F407 replaced with D, E, H, K, R, N, Q, A, G, I, L, S, T, M, V, P, or C; E408 replaced with H, K, R, A, G, I, L, S, T, M, V, N, Q, F, W, Y, P, or C; E409 replaced with H, K, R, A, G, I, L, S, T, M, V, N, Q, F, W, Y, P, or C; and/or L410 replaced with D, E, H, K, R, N, Q, F, W, Y, P, or C of SEQ ID NO:2.

The resulting constructs can be routinely screened for activities or functions described throughout the specification and known in the art. Preferably, the resulting constructs have an increased and/or decreased BAIT activity or function, while the remaining BAIT activities or functions are maintained. More preferably, the resulting constructs have more than one increased and/or decreased BAIT activity or function, while the remaining BAIT activities or functions are maintained.

Additionally, more than one amino acid (e.g., 2, 3, 4, 5, 6, 7, 8, 9 and 10) can be replaced with the substituted amino acids as described above (either conservative or nonconservative). The substituted amino acids can occur in the full length, mature, or proprotein form of BAIT protein, as well as the N- and C-terminal deletion mutants, having the general formula m–n.

A further embodiment of the invention relates to a polypeptide which comprises the amino acid sequence of a BAIT polypeptide having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a polypeptide to have an amino acid sequence which comprises the amino acid sequence of a BAIT polypeptide, which contains at least one, but not more than 10, 9, 8, 7, 6, 5, 4, 3, 2 or 1 amino acid substitutions. In specific embodiments, the number of additions, substitutions, and/or deletions in the amino acid sequence of FIGS. 1A–1B or fragments thereof (e.g., the mature form and/or other fragments described herein), is 1–5, 5–10, 5–25, 5–50, 10–50 or 50–150, conservative amino acid substitutions are preferable.

As described above, the BAIT polypeptide includes a reactive center loop (RCL) which interacts with its target proteinase. Short peptides (e.g., 8–30 residues) containing this loop sequence will bind to BAIT and convert it to a substrate for the target proteinase. Such peptides are therefore antagonists of BAIT and also form part of the present invention. Further, mutants of BAIT with enhanced function are also provided by the invention, including: RCL replacements to increase inhibitory activity with tPA, trypsin or thrombin; mutations that increase structural stability or clearance half-life; and mutations which enhance or block association with cofactors. One of ordinary skill would appreciate that such mutants can be designed and tested using, for instance, the methods described for other serpins in the references cited in the section above on "Serpin Mechanism."

The polypeptides of the present invention are preferably provided in an isolated form, and preferably are substantially purified. A recombinantly produced version of the BAIT polypeptide can be substantially purified by the method described in Osterwalder et al., 1996, supra The polypeptides of the present invention include the polypeptide encoded by the deposited cDNA including the leader, the mature polypeptide encoded by the deposited cDNA minus the leader (i.e., the mature protein), the polypeptide of FIGS. 1A–1B (SEQ ID NO:2) including the leader, the polypeptide of FIGS. 1A–1B (SEQ ID NO:2) minus the leader, as well as polypeptides which have at least 90% similarity, more preferably at least 95% similarity, and still more preferably at least 96%, 97%, 98% or 99% similarity to those described above. Further polypeptides of the present invention include polypeptides at least 80% identical, more preferably at least 90% or 95% identical, still more preferably at least 96%, 97%, 98% or 99% identical to the polypeptide encoded by the deposited cDNA, to the polypeptide of FIGS. 1A–1B (SEQ ID NO:2), and also include portions of such polypeptides with at least 30 amino acids and more preferably at least 50 amino acids.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a BAIT polypeptide is intended that the amino acid sequence of the polypeptide is identical to the reference sequence except that the polypeptide sequence may include up to five amino acid alterations per each 100 amino acids of the reference amino acid of the BAIT polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIGS. 1A–1B (SEQ ID NO:2) or to the amino acid sequence encoded by deposited cDNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art. As described in detail below, the polypeptides of the present invention can also be used to raise polyclonal and monoclonal antibodies, which are useful in assays for detecting BAIT protein expression as described below or as antagonists capable of enhancing or inhibiting BAIT protein function. Further, such polypeptides can be used in the yeast two-hybrid system to "capture" BAIT protein binding proteins which are candidate target proteins for BAIT inhibition, according to the present invention. The yeast two hybrid system is described in Fields and Song, *Nature* 340:245–246 (1989).

Additional preferred polypeptide fragments comprise, or alternatively consist of, the amino acid sequence of residues: M-1 to M-15; A-2 to A-16; F-3 to T-17; L-4 to G-18; G-5 to A-19; L-6 to T-20; F-7 to F-21; S-8 to P-22; L-9 to E-23; L-10 to E-24; V-11 to A-25; L-12 to I-26; Q-13 to A-27; S-14 to D-28; M-15 to L-29; A-16 to S-30; T-17 to V-31; G-18 to N-32; A-19 to M-33; T-20 to Y-34; F-21 to N-35; P-22 to R-36; E-23 to L-37; E-24 to R-38; A-25 to A-39; I-26 to T-40; A-27 to G-41; D-28 to E-42; L-29 to D-43; S-30 to E-44; V-31 to N-45; N-32 to I-46; M-33 to L-47; Y-34 to F-48; N-35 to S-49; R-36 to P-50; L-37 to L-51; R-38 to S-52; A-39 to I-53; T-40 to A-54; G-41 to L-55; E-42 to A-56; D-43 to M-57; E-44 to G-58; N-45 to M-59; I-46 to M-60; L-47 to E-61; F-48 to L-62; S-49 to G-63; P-50 to A-64; L-51 to Q-65; S-52 to G-66; I-53 to S-67; A-54 to T-68; L-55 to Q-69; A-56 to K-70; M-57 to E-71; G-58 to I-72; M-59 to R-73; M-60 to H-74; E-61 to S-75; L-62 to M-76; G-63 to G-77; A-64 to Y-78; Q-65 to D-79; G-66 to S-80; S-67 to L-81; T-68 to K-82; Q-69 to N-83; K-70 to G-84; E-71 to E-85; I-72 to E-86; R-73 to F-87; H-74 to S-88; S-75 to F-89; M-76 to L-90; G-77 to K-91; Y-78 to E-92; D-79 to F-93; S-80 to S-94; L-81 to N-95; K-82 to M-96; N-83 to V-97; G-84 to T-98; E-85 to A-99; E-86 to K-100; F-87 to E-101; S-88 to S-102; F-89 to Q-103; L-90 to Y-104; K-91 to V-105; E-92 to M-106; F-93 to K-107; S-94 to I-108; N-95 to A-109; M-96 to N-110; V-97 to S-111; T-98 to L-112; A-99 to F-113; K-100 to V-114; E-101 to Q-115; S-102 to N-116; Q-103 to G-117; Y-104 to F-118; V-105 to H-119; M-106 to V-120; K-107 to N-121; I-108 to E-122; A-109 to E-123; N-110 to F-124; S-111 to L-125; L-112 to Q-126; F-113 to M-127; V-114 to M-128; Q-115 to K-129; N-116 to K-130; G-117 to Y-131; F-118 to F-132; H-119 to N-133; V-120 to A-134; N-121 to A-135; E-122 to V-136; E-123 to N-137; F-124 to H-138; L-125 to V-139; Q-126 to D-140; M-127 to F-141; M-128 to S-142; K-129 to Q-143; K-130 to N-144; Y-131 to V-145; F-132 to A-146; N-133 to V-147; A-134 to A-148; A-135 to N-149; V-136 to Y-150; N-137 to I-151; H-138 to N-152; V-139 to K-153; D-140 to W-154; F-141 to V-155; S-142 to E-156; Q-143 to N-157; N-144 to N-158; V-145 to T-159; A-146 to N-160; V-147 to N-161; A-148 to L-162; N-149 to V-163; Y-150 to K-164; I-151 to D-165; N-152 to L-166; K-153 to V-167; W-154 to S-168; V-155 to P-169; E-156 to R-170; N-157 to D-171; N-158 to F-172; T-159 to D-173; N-160 to A-174; N-161 to A-175; L-162 to T-176; V-163 to Y-177; K-164 to L-178; D-165 to A-179; L-166 to L-180; V-167 to I-181; S-168 to N-182; P-169 to A-183; R-170 to V-184; D-171 to Y-185; F-172 to F-186; D-173 to K-187; A-174 to G-188; A-175 to N-189; T-176 to W-190; Y-177 to K-191; L-178 to S-192; A-179 to Q-193; L-180 to F-194; I-181 to R-195; N-182 to P-196; A-183 to E-197; V-184 to N-198; Y-185 to T-199; F-186 to R-200; K-187 to T-201; G-188 to F-202; N-189 to S-203; W-190 to F-204; K-191 to T-205; S-192 to K-206; Q-193 to D-207; F-194 to D-208; R-195 to E-209; P-196 to S-210; E-197 to E-211; N-198 to V-212; T-199 to Q-213; R-200 to I-214; T-201 to P-215; F-202 to M-216; S-203 to M-217; F-204 to Y-218; T-205 to Q-219; K-206 to Q-220; D-207 to G-221; D-208 to E-222; E-209 to F-223; S-210 to Y-224; E-211 to Y-225; V-212 to G-226; Q-213 to E-227; I-214 to F-228; P-215 to S-229; M-216 to D-230; M-217 to G-231; Y-218 to S-232; Q-219 to N-233; Q-220 to E-234; G-221 to A-235; E-222 to G-236; F-223 to G-237; Y-224 to I-238; Y-225 to Y-239; G-226 to Q-240; E-227 to V-241; F-228 to L-242; S-229 to E-243; D-230 to I-244; G-231 to P-245; S-232 to Y-246; N-233 to E-247; E-234 to G-248; A-235 to D-249; G-236 to E-250; G-237 to I-251; I-238 to S-252; Y-239 to M-253; Q-240 to M-254; V-241 to L-255; L-242 to V-256; E-243 to L-257; I-244 to S-258; P-245 to R-259; Y-246 to Q-260; E-247 to E-261; G-248 to V-262; D-249 to P-263; E-250 to L-264; I-251 to A-265; S-252 to T-266; M-253 to L-267; M-254 to E-268; L-255 to P-269; V-256 to L-270; L-257 to V-271; S-258 to K-272; R-259 to A-273; Q-260 to Q-274; E-261 to L-275; V-262 to V-276; P-263 to E-277; L-264 to E-278; A-265 to W-279; T-266 to A-280; L-267 to N-281; E-268 to S-282; P-269 to V-283; L-270 to K-284; V-271 to K-285; K-272 to Q-286; A-273 to K-287; Q-274 to V-288; L-275 to E-289; V-276 to V-290; E-277 to Y-291; E-278 to L-292; W-279 to P-293; A-280 to R-294; N-281 to F-295; S-282 to T-296; V-283 to V-297; K-284 to E-298; K-285 to Q-299; Q-286 to E-300; K-287 to I-301; V-288 to D-302; E-289 to L-303; V-290 to K-304; Y-291 to D-305; L-292 to V-306; P-293 to L-307; R-294 to K-308; F-295 to A-309; T-296 to L-310; V-297 to G-311; E-298 to I-312; Q-299 to T-313; E-300 to E-314; I-301 to I-315; D-302 to F-316; L-303 to I-317; K-304 to K-318; D-305 to D-319; V-306 to A-320; L-307 to N-321; K-308 to L-322; A-309 to T-323; L-310 to G-324; G-311 to L-325; I-312 to S-326; T-313 to D-327; E-314 to N-328; I-315 to K-329; F-316 to E-330; I-317 to I-331; K-318 to F-332; D-319 to L-333; A-320 to S-334; N-321 to K-335; L-322 to A-336; T-323 to I-337; G-324 to H-338; L-325 to K-339; S-326 to S-340; D-327 to F-341; N-328 to L-342; K-329 to E-343; E-330 to V-344; I-331 to N-345; F-332 to E-346; L-333 to E-347; S-334 to G-348; K-335 to S-349; A-336 to E-350; I-337 to A-351; H-338 to A-352; K-339 to A-353; S-340 to V-354; F-341 to S-355; L-342 to G-356; E-343 to M-357; V-344 to I-358; N-345 to A-359; E-346 to I-360; E-347 to S-361; G-348 to R-362; S-349 to M-363; E-350 to A-364; A-351 to V-365; A-352 to L-366; A-353 to Y-367; V-354 to P-368; S-355 to Q-369; G-356 to V-370; M-357 to I-371; I-358 to V-372; A-359 to D-373; I-360 to H-374; S-361 to P-375; R-362 to F-376; M-363 to F-377; A-364 to F-378; V-365 to L-379; L-366 to I-380; Y-367 to R-381; P-368 to N-382; Q-369 to R-383; V-370 to R-384; I-371 to T-385; V-372 to G-386; D-373 to T-387; H-374 to I-388; P-375 to L-389; F-376 to F-390; F-377 to M-391; F-378 to G-392; L-379 to R-393; I-380 to V-394; R-381 to M-395; N-382 to H-396; R-383 to P-397; R-384 to E-398; T-385 to T-399; G-386 to M-400; T-387 to N-401; I-388 to T-402; L-389 to S-403; F-390 to G-404; M-391 to H-405; G-392 to D-406; R-393 to F-407; V-394 to E-408; M-395 to E-409; and/or H-396 to L-410 of SEQ ID NO:2. These polypeptide fragments may retain the biological activity of the BAIT polypeptides of the invention and/or may be useful to generate or screen for antibodies, as described further below. Polynucleotides encoding these polypeptide fragments are also encompassed by the invention.

Epitopes and Antibodies

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC™ deposit No. 97722 or encoded by a polynucleotide that hybridizes to the complement of the sequence of SEQ ID NO:1 or contained in ATCC™ deposit No. 97722 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:2), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Specifically preferred are epitopes comprising, or consisting of: a polypeptide comprising amino acid residues from about Val 31 to about Leu 47 (SEQ ID NO:2); a polypeptide comprising amino acid residues from about Leu 62 to about Ser 88 (SEQ ID NO:2); a polypeptide comprising amino acid residues from about Val 155 to about Ala 175 (SEQ ID NO:2); a polypeptide comprising amino acid residues from about Phe 186 to about Pro 215 (SEQ ID NO:2); a polypeptide comprising amino acid residues from about Tyr 225 to about Ile 239 (SEQ ID NO:2); a polypeptide comprising amino acid residues from about Leu 243 to about Leu 255 (SEQ ID NO:2); a polypeptide comprising amino acid residues from about Arg 380 to about Gly 386 (SEQ ID NO:2); and a polypeptide comprising amino acid residues from about Met 395 to about Leu 410. (SEQ ID NO:2). Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimido-benzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86

(1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag onsisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC™. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5): 489–498 (1991); Studnicka et al., Protein Engineering 7(6): 805–814 (1994); Roguska. et al., PNAS 91:969–973 (1994)), and chain shuffling (U.S. Pat. No. 5,565,332).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633, 425; 5,569,825; 5,661,016; 5,545,806; 5,814,318; 5,885, 793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/ receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., E. coli, B. subtilis) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays For Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10. 16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5\times10^{-2}$ M, $10^{-2}$ M, $5\times10^{-3}$ M, $5\times10^{-4}$ M, $10^{-4}$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $5\times10^{-9}$ M, $10^{-9}$ M, $5\times10^{-14}$ M, $10^{-14}$ M, $5\times10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Additionally, nucleic acids comprising sequences encoding BAIT polypeptides of the invention, are administered to treat, inhibit, or prevent a disease or disorder associated with aberrant expression and/or activity of a polypeptide of the invention, by way of gene therapy.

Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342:435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest: 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration. In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. Diagnosis and Imaging Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared t the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99 mTc. The labeled antibody or antibody fragment, will then preferentially accumulate at the location of cells which contain the specific protein. In vivo tumor imaging is described in S. W. Burchiel et al., "Immunopharmacokinetics of Radiolabeled Antibodies and Their Fragments." Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because secreted proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Also, peptide moieties may be added to the polypeptide to facilitate purification. Such regions may be removed prior to final preparation of the polypeptide. The addition of peptide moieties to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).)

Moreover, the polypeptides of the present invention can be fused to marker sequences, such as a peptide which facilitates purification of the fused polypeptide. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984).) Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, supplied by a complementing vector or supplied by the vector itself upon introduction into the host.

In certain preferred embodiments in this regard, the vectors provide for specific expression, which may be inducible and/or cell type-specific. Particularly preferred among such vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophage, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

The DNA insert should be operatively linked to an appropriate. Among known bacterial promoters suitable for use in the present invention include the E. coli lacI and lacZ promoters, the T3 and T7 promoters, the gpt promoter, the phage lambda PR and PL promoters, the phoA promoter and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter. Other suitable promoters will be known to the skilled artisan.

The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, Streptomyces and Salmonella typhimurium cells; fungal cells, such as yeast cells (e.g., Saccharomyces cerevisiae or Pichia pastoris (ATCC™ Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlbad, Calif.). Other suitable vectors will be readily apparent to the skilled artisan.

It is specifically contemplated that the polypeptides of the present invention may in fact be expressed by a host cell lacking a recombinant vector.

Recombinant constructs may be introduced into host cells using well known techniques such as infection, transduction, transfection, transvection, electroporation and transformation. For instance, introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

Transcription of the DNA encoding the polypeptides of the present invention by higher eukaryotes may be increased by inserting an enhancer sequence into the vector. Enhancers are cis-acting elements of DNA, usually about from 10 to 300 bp in length that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, immunoglobulin enhancer and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-0 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5 has been fused with Fc portions for the purpose of high-throughput screening assays to identify antagonists of hIL-5. See, D. Bennett et al., *Journal of Molecular Recognition* 8:52–58 (1995) and K. et al., *The Journal of Biological Chemistry* 270:9459–9471 (1995).

Peptides and polypeptides of the present invention can be produced by chemical synthetic procedures known to those of ordinary skill in the art. For example, polypeptides up to about 80–90 amino acid residues in length may be produced on a commercially available peptide synthesizer model 433A (Applied Biosystems, Inc., Foster City, Calif.). Thus, as will be readily appreciated, the full-length mature BAIT polypeptide can be produced synthetically.

The BAIT protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., *Mol. Cell. Biol.* 5:1111–21 (1985); Koutz, P. J, et al., *Yeast* 5:167–77 (1989); Tschopp, J. F., et al., *Nucl. Acids Res.* 15:3859–76 (1987). Thus, a heterologous coding sequence, such as, for example, a polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., *Nature*, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:Y or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

Diagnosis of Nervous System-Related Disorders

The present inventors have discovered that BAIT is expressed in whole human brain, and to a much lesser extent in adult pancreas and adult heart. More particularly, by Northern blotting a 2 kb mRNA was expressed mostly in adult brain (at a relative level of ~5x) and to a much lesser extent in adult pancreas (1x) and adult heart (~0.5x). Adult tissues not expressing significant amounts of mRNA include placenta, lung, liver, skeletal muscle, kidney, spleen, thymus, prostate, testis, ovary, small intestine, colon, and peripheral blood leukocytes. In addition, in the nervous system a 2 kb mRNA was seen in cerebral cortex, medulla, occipital lobe, frontal lobe, temporal lobe, putamen, and spinal cord but not in cerebellum. In the chicken, neuroserpin, the presumptive ortholog of the human BAIT protein, was found to be secreted from axons of both CNS and PNS neurons. Osterwalder et al., supra. The most prominent expression of neuroserpin in adult chickens is found in the hyperstriatum accessorium, the neostriaum and the hippocampus, plastic regions of the adult brain involved in processes of learning and memory where a subtle balance between and anti-proteolytic activities seems to be required for appropriate synaptic function. Id. at 295 1. Further, transgenic mice with an enhanced proteolytic activity in the cortex and hippocampus due to overexpression of urokinase-type plasminogen activator (u-PA) have been found to exhibit impaired spatial, olfactory and taste aversion learning. Id. Further still, elimination of a serpin inhibitor of u-PA, PNI (described above) by homologous recombination leads to reduced long-term potentiation (LTP) of learning, whereas overexpression of PNI results in enhanced LTP of hippocampal neurons. Id. The available observations on temporal-spatial patterns of expression of neuroserpin the chicken and BAIT polypeptide in human tissues implicate BAIT as a regulator for synaptogenesis and the subsequent remodelling processes including synapse elimination rather than neurite outgrowth. Id.

Accordingly, for a number of disorders of the central or peripheral nervous system, significantly higher or lower levels of BAIT gene expression may be detected in certain tissues (e.g., adult brain, embryonic retina, cerebellum and spinal chord), or bodily fluids (e.g., serum, plasma, urine, synovial fluid or spinal fluid) taken from an individual having such a disorder, relative to a "standard" BAIT gene expression level, i.e., the BAIT expression level in healthy tissue from an individual not having the nervous system disorder. Thus, the invention provides a diagnostic method useful during diagnosis of nervous system disorders, which involves: (a) assaying BAIT gene expression level in cells or body fluid of an individual; (b) comparing the BAIT gene expression level with a standard BAIT gene expression level, whereby an increase or decrease in the assayed BAIT gene expression level compared to the standard expression level is indicative of disorder in the nervous system.

By individual is intended mammalian individuals, preferably humans, including adults, children, babies and embryos or fetuses at all stages of development of the nervous system. By "measuring the expression level of the gene encoding the BAIT protein" is intended qualitatively or quantitatively measuring or estimating the level of the BAIT protein or the level of the mRNA encoding the BAIT protein in a first biological sample either directly (e.g., by determining or estimating absolute protein level or mRNA level) or relatively (e.g., by comparing to the BAIT protein level or mRNA level in a second biological sample). Preferably, the BAIT protein level or mRNA level in the first biological sample is measured or estimated and compared to a standard BAIT protein level or mRNA level, the standard being taken from a second biological sample obtained from an individual not having the disorder or being determined by averaging levels from a population of individuals not having a disorder of the immune system. As will be appreciated in the art, once a standard BAIT protein level or mRNA level is known, it can be used repeatedly as a standard for comparison.

By "biological sample" is intended any biological sample obtained from an individual, body fluid, cell line, tissue culture, or other source which contains BAIT protein or mRNA. As indicated, biological samples include body fluids (such as sera, plasma, urine, synovial fluid and spinal fluid) which contain secreted mature BAIT protein, nervous system tissue, and other tissue sources found to express BAIT or a BAIT receptor. Methods for obtaining tissue biopsies and body fluids from mammals are well known in the art. Where the biological sample is to include mRNA, a tissue biopsy is the preferred source.

The present invention is useful for diagnosis of various nervous system-related disorders in mammals, preferably humans. Such disorders include impaired processes of learning and memory, including impaired spatial, olfactory and taste aversion learning, learning and memory impairments associated with Alzheimer's disease, and the like.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the BAIT protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., *Cell* 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. BAIT protein cDNA labeled according to any appropriate method (such as the $^{32}$P-multiprimed DNA labeling system (Amersham)) is used as probe. After hybridization overnight, the filter is washed and exposed to x-ray film. cDNA for use as probe according to the present invention is described in the sections above and will preferably be at least 15 bp in length.

S1 mapping can be performed as described in Fujita et al., *Cell* 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the BAIT protein). Northern blot analysis can be performed as described above.

Preferably, levels of mRNA encoding the BAIT protein are assayed using the RT-PCR method described in Makino et al., *Technique* 2:295–301 (1990). By this method, the radioactivities of the "amplicons" in the polyacrylamide gel bands are linearly related to the initial concentration of the target mRNA. Briefly, this method involves adding total RNA isolated from a biological sample in a reaction mixture containing a RT primer and appropriate buffer. After incubating for primer annealing, the mixture can be supplemented with a RT buffer, dNTPs, DTT, RNase inhibitor and reverse transcriptase. After incubation to achieve reverse transcription of the RNA, the RT products are then subject to PCR using labeled primers. Alternatively, rather than labeling the primers, a labeled dNTP can be included in the PCR reaction mixture. PCR amplification can be performed in a DNA thermal cycler according to conventional techniques. After a suitable number of rounds to achieve amplification, the PCR reaction mixture is electrophoresed on a polyacrylamide gel. After drying the gel, the radioactivity of the appropriate bands (corresponding to the mRNA encoding the BAIT protein)) is quantified using an imaging analyzer. RT and PCR reaction ingredients and conditions, reagent and gel concentrations, and labeling methods are well known in the art. Variations on the RT-PCR method will be apparent to the skilled artisan. Any set of oligonucleotide primers which will amplify reverse transcribed target mRNA can be used and can be designed as described in the sections above.

Assaying BAIT protein levels in a biological sample can occur using any art-known method. Preferred for assaying BAIT protein levels in a biological sample are antibody-based techniques. For example, BAIT protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g., with urea and neutral detergent, for the liberation of BAIT protein for Western-blot or dot/slot assay (Jalkanen, M., et al., *J. Cell. Biol.* 101:976–985 (1985); Jalkanen, M., et al., *J. Cell Biol.* 105:3087–3096 (1987)). In this technique, which is based on the use of cationic solid phases, quantitation of BAIT protein can be accomplished using isolated BAIT protein as a standard. This technique can also be applied to body fluids. With these samples, a molar concentration of BAIT protein will aid to set standard values of BAIT protein content for different body fluids, like serum, plasma, urine, spinal fluid, etc. The normal appearance of BAIT protein amounts can then be set using values from healthy individuals, which can be compared to those obtained from a test subject.

Other antibody-based methods useful for detecting BAIT protein gene expression include immunoassays, such as the enzyme linked immunosorbent assay (ELISA) and the radioimmunoassay (RIA). For example, a BAIT protein-specific monoclonal antibody can be used both as an immunoadsorbent and as an enzyme-labeled probe to detect and quantify the BAIT protein. The amount of BAIT protein present in the sample can be calculated by reference to the amount present in a standard preparation using a linear regression computer algorithm. Such an ELISA for detecting a tumor antigen is described in Iacobelli et al., *Breast Cancer Research and Treatment* 11: 19–30 (1988). In another ELISA assay, two distinct specific monoclonal antibodies can be used to detect BAIT protein in a body fluid. In this assay, one of the antibodies is used as the immunoadsorbent and the other as the enzyme-labeled probe.

The above techniques may be conducted essentially as a "one-step" or "two-step" assay. The "one-step" assay involves contacting BAIT protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I, carbon ($^{14}$C), sulfur ($^{35}$S), tritium ($^{3}$H), indium ($^{112}$In), and technetium ($^{99m}$Tc), and fluorescent labels, such as fluorescein and rhodamine, and biotin.

In addition to assaying BAIT protein levels in a biological sample obtained from an individual, BAIT protein can also be detected in vivo by imaging. Antibody labels or markers for in vivo imaging of BAIT protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A BAIT protein-specific antibody or antibody fragment which has been labeled with an appropriate detectable imaging moiety, such as a radioisotope (for example, $^{131}$I, $^{112}$In, $^{99m}$Tc), a radio-opaque substance, or a material detectable by nuclear magnetic resonance, is introduced (for example, parenterally, subcutaneously or intraperitoneally) into the mammal to be examined for immune system disorder. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$m Tc. The labeled antibody or antibody fragment will then preferentially accumulate at the location of cells which contain BAIT protein. In vivo tumor imaging is described in S. W. Burchiel et al., "Immunopharmaco-kinetics of Radiolabeled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

BAIT-protein specific antibodies for use in the present invention can be raised against the intact BAIT protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to BAIT protein. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the BAIT protein or an antigenic fragment thereof can be administered to an animal in order to induce the production of sera containing polyclonal antibodies. In a preferred method, a preparation of BAIT protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or BAIT protein binding fragments thereof). Such monoclonal antibodies can be prepared using hybridoma technology (Kohler et al. *Nature* 256:495 (1975); Kohler et al., *Eur. J. Immunol.* 6:511 (1976); Kohler et al., *Eur. J. Immunol.* 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a BAIT protein antigen or, more preferably, with a BAIT protein-expressing cell. Suitable cells can be recognized by their capacity to bind anti-BAIT protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 g/ml of streptomycin. The splenocytes of such mice are extracted and fused with a suitable myeloma cell line. Any suitable myeloma cell line may be employed in accordance with the present invention; however, it is preferable to employ the parent myeloma cell line (SP$_2$0), available from the American Type Culture Collection, Manassas, Va. After fusion, the resulting hybridoma cells are selectively maintained in HAT medium, and then cloned by limiting dilution as described by Wands et al. (*Gastroenterology* 80:225–232 (198 1)). The hybridoma cells obtained through such a selection are then assayed to identify clones which secrete antibodies capable of binding the BAIT protein antigen.

Alternatively, additional antibodies capable of binding to the BAIT protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, BAIT-protein specific antibodies are used to immunize an animal, preferably a mouse. The splenocytes of such an animal are then used to produce hybridoma cells, and the hybridoma cells are screened to identify clones which produce an antibody whose ability to bind to the BAIT protein-specific antibody can be blocked by the BAIT protein antigen. Such antibodies comprise anti-idiotypic antibodies to the BAIT protein-specific antibody and can be used to immunize an animal to induce formation of further BAIT protein-specific antibodies.

It will be appreciated that Fab and F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, BAIT protein-binding fragments can be produced through the application of recombinant DNA technology or through synthetic chemistry.

Where in vivo imaging is used to detect enhanced levels of BAIT protein for diagnosis in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

Further suitable labels for the BAIT protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since it avoids the problem of dehalogenation of the $^{125}$I or $^{131}$I-labeled monoclonal antibody by the liver. In addition, this radionucleotide has a more favorable gamma emission energy for imaging (Perkins et al., *Eur. J. Nucl. Med.* 10:296–301 (1985); Carasquillo et al., *J Nucl. Med.* 28:281–287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., *J. Nucl. Med.* 28:861–870 (1987)). Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{112}$Eu label, a fluorescein label, an isothiocyanate label, a rhodamine label, a phycoerythrin label, a phycocyanin label, an allophycocyanin label, an ophthaldehyde label, and a fluorescamine label. Examples of suitable toxin labels include diphtheria toxin, ricin, and cholera toxin. Examples of chemiluminescent labels include a luminal label, an isoluminal label, an aromatic acridinium ester label, an imidazole label, an acridinium salt label, an oxalate ester label, a luciferin label, a luciferase label, and an aequorin label. Examples of nuclear magnetic resonance contrasting agents include heavy metal nuclei such as Gd, Mn, and iron.

Typical techniques for binding the above-described labels to antibodies are provided by Kennedy et al., *Clin. Chim. Acta* 70:1–31 (1976), and Schurs et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Treatment of Nervous System-Related and Other Disorders

As noted above, BAIT polynucleotides, polypeptides and other aspects of this invention are useful for diagnosis of various nervous system-related disorders in mammals, including impaired processes of learning and memory, including impaired spatial, olfactory and taste-aversion learning, learning and memory impairments associated with Alzheimer's disease, and the like. Given the activities modulated by BAIT, it is readily apparent that a substantially altered (increased or decreased) level of expression of BAIT in an individual compared to the standard or "normal" level produces pathological conditions such as those described above in relation to diagnosis of nervous system-related disorders. It will also be appreciated by one of ordinary skill that, since the BAIT protein of the invention is translated with a leader peptide suitable for secretion of the mature protein from the cells which express BAIT, when BAIT protein (particularly the mature form) is added from an exogenous source to cells, tissues or the body of an individual, the protein will exert its modulating activities on any of its target cells of that individual. Therefore, it will be appreciated that conditions caused by a decrease in the standard or normal level of BAIT activity in an individual, or an increase in a protease susceptible to inhibition by BAIT, particularly disorders of the nervous system, can be treated by administration of BAIT protein.

Figure 5:
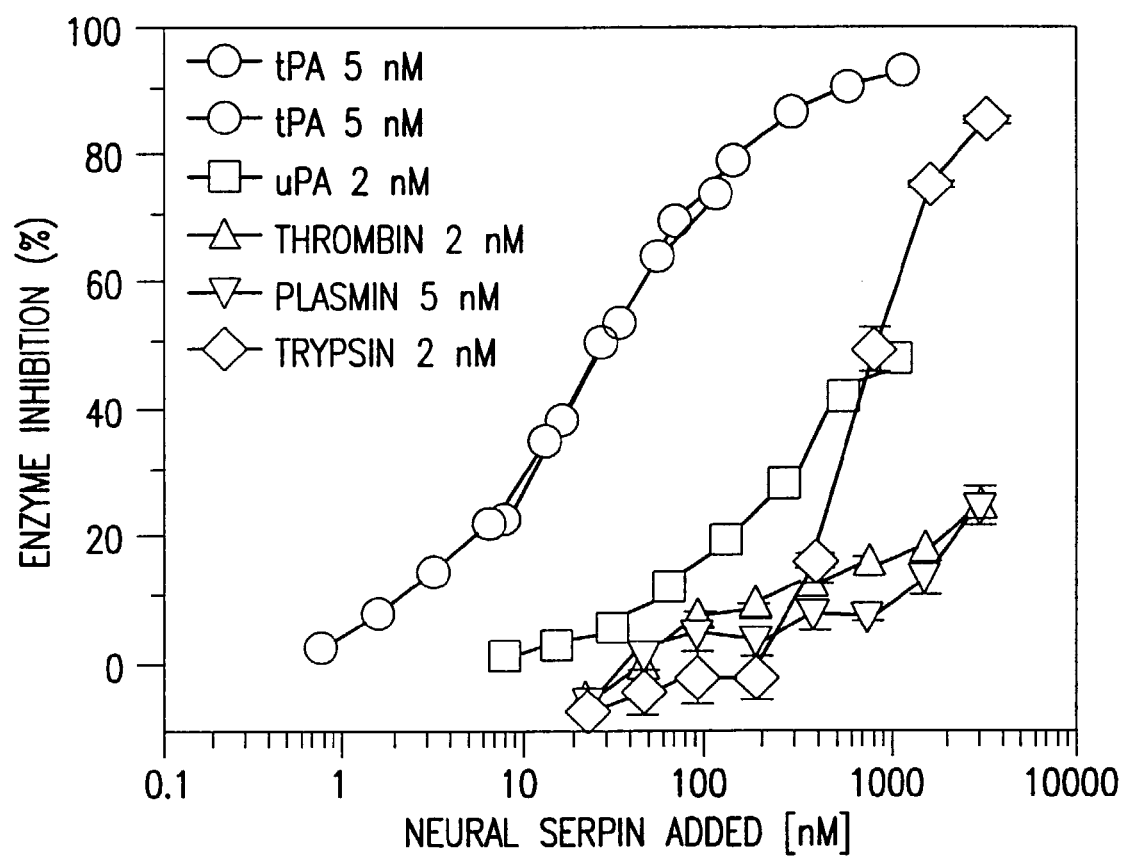
FIG. 5 shows the results of tests for inhibitory activity of purified human BAIT polypeptide on several proteolytic enzymes including thrombin (2 nM; -Δ-); tissue-type plasminogen activator (tPA, 5 nM; -○-), urokinase-type plasminogen activator (uPA, 2 nM; -□-), plasmin (5 nM; -∇-), and trypsin (2 nM; -◇-).

The human BAIT protein of the present invention has been shown to exhibit selective inhibition of tissue-type plasminogen activator (t-PA) with a lesser degree of inhibition of trypsin, thrombin or urokinase-type plasminogen activator (u-PA). More in particular, in vitro enzymatic activity has been demonstrated for the baculovirus expressed purified protein. FIG. 5 shows the inhibition of t-PA, u-PA, plasmin, trypsin, and thrombin proteolytic activity with increasing amounts of purified protein expressed and purified as described below. t-PA was inhibited with a half-maximal inhibitory concentration IC$_{50}$) of 200 nM, u-PA and trypsin were inhibited at an IC$_{50}$ of 1 μM and 0.7 μM, respectively. No other protease was inhibited to 50% of control. The rate constant for BAIT reaction with tPA is about $7.8 \pm 1.5 \times 10^4$ mol/sec.

More in particular, the inhibitory activity against various tPA (Genentech), uPA (Serono), plasmin (a gift of Dr. D. Strickland), thrombin (a gift of Dr. S. T. Olson), and β-trypsin (a gift of Dr. S. T. Olson), was determined in a single step chromogenic assay essentially as Lawrence, D. A., et. al. (1990) The Journal of Biological Chemistry, 265, 20293–20301. Briefly, BAIT containing samples were serially diluted in microtiter plates into 0.15 M NaCl, 0.05 M Tris-HCl, pH 7.5 containing 100 μg/ml bovine serum albumin, and 0.01% Tween 80, 100 μl final volume. Enzyme was added (5 nM for tPA and plasmin, and 2 nM for thrombin, uPA, and trypsin), and the samples incubated for 30 minutes at 23° C. Next, 100 μl of the same buffer containing 0.5 mM substrate, (Spectrozyme tPA (BioPool) for tPA, S2444 (Chromogenix) for uPA, S2390 (Chromogenix) for plasmin, and chromozym TRY (Boehringer Mannheim) for trypsin and thrombin. The plates were then were incubated at 37° C. in a ThermoMax plate reader and the change in absorbance at 405 nM monitored for 30 minutes. The amount of inhibition was calculated from the residual enzyme activity.

These results of these assays are shown in FIG. 5 where the % inhibition of each enzyme is plotted against the concentration of BAIT ("neural serpin").

Thus, the invention also provides a method of treatment of an individual in need of an increased level of BAIT activity (or, preferably, of decreased proteolytic activity of a BAIT-susceptible protease, particularly t-PA, trypsin, thrombin and/or urokinase-type plasminogen activator (u-PA)) comprising administering to such an individual a pharmaceutical composition comprising an amount of an isolated BAIT polypeptide, polynucleotide, agonist, antagonist, including antibodies, of the invention, particularly a mature form of the BAIT protein of the invention, effective to increase the BAIT activity level (and, preferably, thereby decreasing the BAIT-susceptible protease activity) in such an individual.

Additionally, the invention also provides a method of treatment of an individual in need of a decreased level of BAIT activity (or, preferably, of increased proteolytic activity of a BAIT-susceptible protease, particularly t-PA, trypsin, thrombin and/or urokinase-type plasminogen activator (u-PA)) comprising administering to such an individual a pharmaceutical composition comprising an amount of an isolated BAIT polypeptide, polynucleotide, agonist, antagonist, including antibodies, of the invention, particularly a mature form of the BAIT protein of the invention, effective to decrease the BAIT activity level (and, preferably, thereby decreasing the BAIT-susceptible protease activity) in such an individual.

Moreover, the invention also provides a method of treatment of an individual in need of an increase or decreased level of apoptosis comprising administering to such an individual a pharmaceutical composition comprising an amount of an isolated BAIT polypeptide, polynucleotide, agonist, antagonist, including antibodies, of the invention, particularly a mature form of the BAIT protein of the invention, effective to increase or decrease the BAIT activity level in such an individual.

In one preferred embodiment, the invention provides a method of treatment of an individual who has lacked oxygen and/or blood in the brain (e.g., stroke, ischemia, etc.) comprising administering to such an individual a pharmaceutical composition comprising an amount of an isolated BAIT polypeptide, polynucleotide, agonist, antagonist, including antibodies, of the invention, particularly a mature form of the BAIT protein of the invention, effective to treat such an individual.

As noted above, one member in the serpin family closely related to BAIT is protease nexin I (PNI) or glia-derived nexin (GDN) which has been shown to inhibit thrombin specifically and to promote, in vitro, neurite extension in neuroblastoma cell lines as well as primary hippocampal, and sympathetic neurons. The PNI gene is induced transcriptionally and protein levels are increased following rat sciatic nerve axotomy. Other neurotrophic factors like nerve growth factor, brain-derived neurotrophic factor, and insulin-like growth factor I respond likewise to peripheral nerve damage. Treatment of chick developing motoneurons, i.e. E6–E9 lumbrosacral motoneurons which normally undergo apoptosis, with PNI results in increased survival of motoneurons. Motoneuron death experimentally induced by sciatic nerve lesioning in mouse is also decreased by PNI addition. Alzheimer-diseased brain regions contain higher PNI/thrombin complexes compared with free PNI than do normal brains suggesting that PNI may have a role in CNS pathology.

Thus, BAIT can be used for treating peripheral neuropathies such as ALS or multiple sclerosis. Motoneuron or sensory neuron damage resulting from spinal cord injury also may be prevented by treatment with BAIT. In addition, central nervous system diseases like Alzheimer's disease may be treated with BAIT or, preferably, a small molecule analog capable of crossing the blood-brain barrier, which analog can be identified according to the methods of the present invention.

Aside from the nervous system-related disorders described above, under diagnostic uses of the invention based on detecting BAIT expression, the protease inhibitory activity of BAIT protein of the present invention also indicates that this protein may be used for therapeutic treatment of other conditions where excessive proteolytic activity of a BAIT susceptible protease may be involved, particularly t-PA. Thus, BAIT may be used to modulate the process of clot breakdown, for instance, in combination with Activase (recombinant t-PA) which Genentech is marketing for clot dissolution after stroke. A major problem with the present Activase therapy is that frequently excessive hemorrhaging occurs. BAIT provides a specific inhibitor of t-PA which would fine tune the treatment process and not interact with other serine proteases in the nervous system. Similarly, a product called Trasylol (aprotinin), a protease inhibitor, is being marketed by Bayer for bleeding disorders. The beneficial action of this serine protease inhibitor in limiting blood loss after cardiopulmonary bypass has been widely reported.

PNI has been shown to inhibit breakdown of extracellular matrix in a fibroblast tumor cell line. Such breakdown is thought to enable tumor cells to metastasize by weakening of extracellular matrix which normally prevents penetration of unrelated cells through a tissue. BAIT also may be used to inhibit extracellular matrix destruction associated with tumors secreting a BAIT-susceptible protease, for instance, neural tissue tumors secreting t-PA.

The BAIT composition will be formulated and dosed in a fashion consistent with good medical practice, taking into account the clinical condition of the individual patient (especially the side effects of treatment with BAIT composition alone), the site of delivery of the BAIT composition, the method of administration, the scheduling of administration, and other factors known to practitioners. The "effective amount" of BAIT composition for purposes herein is thus determined by such considerations.

As a general proposition, the total pharmaceutically effective amount of BAIT polypeptide administered parenterally per dose will be in the range of about 1 g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the BAIT polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the BAIT of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The BAIT composition is also suitably administered by sustained-release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547–556 (1983)), poly (2-hydroxyethyl methacrylate) (R. Langer et al., J. Biomed. Mater. Res. 15:167–277 (198 1), and R. Langer, Chem. Tech. 12:98–105 (1982)), ethylene vinyl acetate (R. Langer et al., Id.) or poly-D-(–)-3-hydroxybutyric acid (EP 133,988). Sustained-release BAIT compositions also include liposomally entrapped BAIT polypeptide. Liposomes containing BAIT are prepared by methods known per se: DE 3,218,12 1; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal BAIT polypeptide therapy.

For parenteral administration, in one embodiment, the BAIT is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the BAIT composition (and, optionally, any cofactor which may enhance its activity) uniformly and intimately with liquid carriers or finely divided solid carriers or both. Then, if necessary, the product, is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The BAIT polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of BAIT polypeptide salts.

BAIT composition to be used for therapeutic administration must be sterile. Sterility is readily accomplished by filtration through sterile filtration membranes (e.g., 0.2 micron membranes). Therapeutic BAIT compositions generally are placed into a container having a sterile access port, for example, an intravenous solution bag or vial having a stopper pierceable by a hypodermic injection needle.

BAIT composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous BAIT polypeptide solution, and the resulting mixture is lyophilized. The infusion solution is prepared by reconstituting the lyophilized BAIT polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of BAIT on proteases, such as its interaction with proteases or with protein cofactors such as extracellular matrix proteins. Thus, protease-inhibiting activity of another serpin, plasminogen activator inhibitor-I (PAI-1), is known to be modulated by its protein cofactor, vitronectin, which binds to active PAI-1 and prevents its spontaneous conversion to a latent form. See, for instance, Reilly, T. M., et al., supra. Similarly, heparin is known to enhance the activity of antithrombin III and several other serpins. The present invention provides an assay for identifying such a protein or other cofactor which binds to BAIT and thereby modulates its anti-proteolytic activity. In general, therefore, an agonist in the present context is a compound which increases the natural biological functions of BAIT or which functions in a manner similar to BAIT, while antagonists decrease or eliminate such functions.

For example, a cellular compartment, such as a membrane or a preparation thereof, such as a membrane-preparation, may be prepared from a cell that expresses a molecule that binds BAIT, such as a molecule of a signaling or regulatory pathway modulated by BAIT. The preparation is incubated with labeled BAIT in the absence or the presence of a candidate molecule which may be a BAIT agonist or antagonist. The ability of the candidate molecule to bind the binding molecule is reflected in decreased binding of the labeled ligand. Molecules which bind gratuitously, i.e., without inducing the effects of BAIT on binding the BAIT binding molecule, are most likely to be good antagonists.

Molecules that bind well and elicit effects that are the same as or closely related to BAIT are agonists.

BAIT-like effects of potential agonists and antagonists may be measured, for instance, by determining activity of a second messenger system following interaction of the candidate molecule with a cell or appropriate cell preparation, and comparing the effect with that of BAIT or molecules that elicit the same effects as BAIT. Second messenger systems that may be useful in this regard include but are not limited to AMP guanylate cyclase, ion channel or phosphoinositide hydrolysis second messenger systems.

Another example of an assay for BAIT antagonists is a competitive assay that combines BAIT and a potential antagonist BAIT-susceptible protease, particularly t-PA, under appropriate conditions for a competitive inhibition assay. BAIT can be labeled, such as by radioactivity, such that the number of BAIT molecules bound to protease molecules can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as BAIT susceptible protease molecule, without inducing BAIT-induced activities, thereby preventing the action of BAIT by excluding BAIT from binding.

Other potential antagonists include antisense molecules. Antisense technology can be used to control gene expression through antisense DNA or RNA or through triple-helix formation. Antisense techniques are discussed, for example, in Okano, J. *Neurochem.* 56: 560 (1991); "Oligodeoxynucleotides as Antisense Inhibitors of Gene Expression," CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of BAIT. The antisense RNA oligonucleotide hybridizes to the mRNA in vivo and blocks translation of the mRNA molecule into BAIT polypeptide. The oligonucleotides described above can also be delivered to cells such that the antisense RNA or DNA may be expressed in vivo to inhibit production of BAIT.

The agonists and antagonists may be employed in a composition with a pharmaceutically acceptable carrier, e.g., as described above.

The BAIT agonists may be employed in place of a BAIT polypeptide, for instance, for treating peripheral neuropathies such as ALS or multiple sclerosis. Motoneuron or sensory neuron damage resulting from spinal cord injury also may be prevented by treatment with BAIT agonists. In addition, central nervous system diseases like Alzheimer's disease may be treated a small molecule agonist capable of crossing the blood-brain barrier, which analog can be identified according to the methods of the present invention. BAIT agonists also may be used for therapeutic treatment of other conditions where excessive proteolytic activity of a BAIT susceptible protease may be involved, particularly t-PA. Thus, BAIT may be used to modulate the process of clot breakdown, for instance, in combination with Activase (recombinant t-PA) for clot dissolution after stroke. Further, BAIT agonists also may be used to inhibit extracellular matrix destruction associated with tumors secreting a BAIT-susceptible protease, for instance, neural tissue tumors secreting t-PA.

The BAIT antagonists may be used in a method for treating an individual in need of a decreased level of BAIT activity in the body (i.e., less inhibition of a protease susceptible to BAIT) comprising administering to such an individual a composition comprising a therapeutically effective amount of a BAIT antagonist. As noted above, elimination of a serpin inhibitor of u-PA, PNI (described above) by homologous recombination leads to reduced long-term potentiation (LTP) of learning, whereas overexpression of PNI results in enhanced LTP of hippocampal neurons. Id. Similarly, antagonists of BAIT activity capable of passing the blood-brain barrier, by mimicking overexpression of BAIT, can be used to enhance LTP of hippocampal neurons in nervous system conditions characterized by excessive BAIT expression.

Neurological Diseases

Nervous system diseases, disorders, and/or conditions, which can be treated, prevented, and/or diagnosed with the compositions of the invention (e.g., polypeptides, polynucleotides, and/or agonists or antagonists, including antibodies), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors), or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, *Drosophila*, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labelled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605, 793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be alterred by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, *Pseudomonas* exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Anitsense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric ligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-O-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Chromosome Assays

Chromosome mapping studies have shown that the BAIT gene maps in the human genome to the location 4q31.2–31.3. Thus, the nucleic acid molecules of the present invention are also valuable for chromosome identification. The sequence is specifically targeted to and can hybridize with the above particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a BAIT protein gene. This can be accomplished using a variety of well known techniques and libraries, which generally are available commercially. The genomic DNA then is used for in situ chromosome mapping using well known techniques for this purpose. Typically, in accordance with routine procedures for chromosome mapping, some trial and error may be necessary to identify a genomic probe that gives a good in situ hybridization signal.

In addition, in some cases, sequences can be mapped to chromosomes by preparing PCR primers (preferably 15–25 bp) from the cDNA. Computer analysis of the 3 untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified portion.

PCR mapping of somatic cell hybrids is a rapid procedure for assigning a particular DNA to a particular chromosome.

Using the present invention with the same oligonucleotide primers, sublocalization can be achieved with panels of portions from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. This assumes 1 megabase mapping resolution and one gene per 20 kb.

EXAMPLES

Example 1

Expression and Purification of BAIT in *E. coli*

Having generally described the invention, the same will be more readily understood by reference to the following examples, which are provided by way of illustration and are not intended as limiting.

The bacterial expression vector pQE9 (pD10) was used for bacterial expression in this example. (QIAGEN, Inc., 9259 Eton Avenue, Chatsworth, Calif., 91311). pQE9 encodes ampicillin antibiotic resistance ("Ampr") and contains a bacterial origin of replication ("ori"), an IPTG inducible promoter, a ribosome binding site ("RBS"), six codons encoding histidine residues that allow affinity purification using nickel-nitrilo-triacetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the amino terminus of that polypeptide.

The DNA sequence encoding the desired portion BAIT protein lacking the hydrophobic leader sequence was amplified from the deposited cDNA clone using PCR oligonucleotide primers which anneal to the amino terminal sequences of the desired portion of the BAIT protein and to sequences in the deposited construct 3' to the cDNA coding sequence. Additional nucleotides containing restriction sites to facilitate cloning in the pQE9 vector are added to the 5' and 3' primer sequences, respectively.

For cloning the mature protein, the 5' primer has the sequence 5' GAGCATGGATCCGCCACTTTCCCTGAG-GAA 3' (SEQ ID NO:10) containing the underlined Bam-HI restriction site followed by 18 nucleotides of the amino terminal coding sequence of the mature BAIT sequence in FIGS. 1A–1B. One of ordinary skill in the art would appreciate, of course, that the point in the protein coding sequence where the 5' primer begins may be varied to amplify a DNA segment encoding any desired portion of the complete BAIT protein shorter or longer than the mature form. The 3' primer has the sequence 5' GCACATGGATC-CTTAAAGTTCTTCGAAATCATG 3'(SEQ ID NO:11) containing the underlined BamHI restriction site followed by 21 nucleotides complementary to the 3' end of the coding sequence of the BAIT DNA sequence in FIGS. 1A–1B.

The amplified BAIT DNA fragment and the vector pQE9 were digested with BamHI and the digested DNAs are then ligated together. Insertion of the BAIT DNA into the restricted pQE9 vector places the BAIT protein coding region downstream from the IPTG-inducible promoter and in-frame with an initiating AUG and the six histidine codons.

The ligation mixture was transformed into competent *E. coli* cells using standard procedures such as those described in Sambrook et al., *Molecular Cloning: a Laboratory Manual*, 2nd Ed.; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing BAIT protein, is available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs were grown overnight ("O/N") in liquid culture in LB media supplemented with both ampicillin (100 μg/ml) and kanamycin (25 μg/ml). The O/N culture is used to inoculate a large culture, at a dilution of approximately 1:25 to 1:250. The cells were grown to an optical density at 600 nm ("OD600") of between 0.4 and 0.6 isopropyl-b-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH 8. The cell debris was removed by centrifugation, and the supernatant containing the BAIT was loaded onto a nickel-nitrilo-tri-acetic acid ("Ni-NTA") affinity resin column (available from QIAGEN, Inc., supra). Proteins with a 6×His tag bind to the NiNTA resin with high affinity and can be purified in a simple one-step procedure (for details see: The Q1Aexpressionist, 1995, QIAGEN, Inc., supra). Briefly the supenatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the BAIT is eluted with 6 M guanidine-HCl, pH 5.

The purified protein was then renatured by dialyzing it against phosphate buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1 M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM imidazole. Immidazole is removed by a final dialyzing step against PBS or 50 mM sodium acetate pH 6 buffer plus 200 mM NaCl. The purified protein is stored at 4° C. or frozen at −80° C.

Example 2

Cloning, Expression and Purification of BAIT Protein in a Baculovirus Expression System In this illustrative example, the plasmid shuttle vector pA2 is used to insert the cloned DNA encoding the complete protein, including its naturally associated secretory signal (leader) sequence, into a baculovirus to express the mature BAIT protein, using standard methods as described in Summers et al., A *Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (Ac-MINPV) followed by convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (1989).

The cDNA sequence encoding the full length BAIT protein in the deposited clone, including the AUG initiation codon and the naturally associated leader sequence shown in FIGS. 1A–1B (SEQ ID NO: 2), is amplified using PCR oligonucleotide primers corresponding to the 5' and 3' sequences of the gene. The 5' primer has the sequence 5' GAGCATGGATCCGCCATCATGGCTTTCCTTGGACTC 3' (SEQ ID NO:12) containing the underlined BamHI restriction enzyme site, an efficient signal for initiation of translation in eukaryotic cells, as described by Kozak, M., J. *Mol. Biol.* 196:947–950 (1987), followed by 18 nucleotides of the sequence of the complete BAIT protein shown in FIGS. 1A–1B, beginning with the AUG initiation codon. The 3' primer has the sequence 5'-GAGCATTCTAGAGTTGCAAACATAATGTGC-3' (SEQ ID NO:13) containing the underlined XbaI restriction site followed by 18 nucleotides complementary to the 3' noncoding sequence in FIGS. 1A–1B.

The amplified fragment was isolated from a 1% agarose gel using a commercially available nucleic acid purification kit (GENECLEAN™ BIO 101 Inc., La Jolla, Calif.). The fragment then is digested with BamHI and XbaI and again was purified on a 1% agarose gel. This fragment is designated herein F1.

The plasmid was digested with the restriction enzymes BamHI and XbaI using routine procedures known in the art. The DNA was then isolated from a 1% agarose gel using a commercially available nucleic acid purification kit (GENECLEAN™ BIO 101 Inc., La Jolla, Calif.). This vector DNA is designated herein "V1".

Fragment F1 and the plasmid V1 were ligated together with T4 DNA ligase. Competent *E. coli* cells were transformed with the ligation mixture and spread on culture plates. Bacteria were identified that contain the plasmid with the human BAIT gene by digesting DNA from individual colonies using BamHI and XbaI and then analyzing the digestion product by gel electrophoresis. The sequence of the cloned fragment was confirmed by DNA sequencing. This plasmid is designated herein pA2BAIT.

Five μg of the plasmid pA2BAIT was co-transfected with 1.0 μg of a commercially available linearized baculovirus DNA ("BACULOGOLD™ baculovirus DNA", Pharmingen, San Diego, Calif.), using the lipofection method described by Felgner et al., *Proc. Natl. Acad. Sci. USA* 84: 7413–7417 (1987). One μg of BACULOGOLD™ virus DNA and 5 μg of the plasmid pA2BAIT were mixed in a sterile well of a microtiter plate containing 50 μl of serum-free Grace's medium (Life Technologies Inc., Gaithersburg, Md.). Afterwards, 10 μl LIPOFECTIN™ (liposome transfection reagent) plus 90 μl Grace's medium were added, mixed and incubated for 15 minutes at room temperature. Then the transfection mixture was added drop-wise to Sf9 insect cells (ATCC™ CRL 1711) seeded in a 35 mm tissue culture plate with 1 ml Grace's medium without serum. The plate was then incubated for 5 hours at 27° C. After 5 hours the transfection solution was removed from the plate and 1 ml of Grace's insect medium supplemented with 10% fetal calf serum was added. The plate was put back into an incubator and cultivation was continued at 27° C. for four days.

After four days the supenatant was collected and a plaque assay was performed, as described by Summers and Smith, supra. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques were picked with the tip of a micropipettor (e.g., Eppendorf). The agar containing the recombinant viruses were then resuspended in a microcentrifuge tube containing 200 μl of Grace's medium and the suspension containing the recombinant baculovirus was used to infect Sf9 cells seeded in 35 mm dishes. Four days later the supernatants of these culture dishes were harvested and then they were stored at 4° C. The recombinant virus is called V-BAIT.

To verify the expression of the BAIT gene Sf9 cells were grown in Grace's medium supplemented with 10% heat-inactivated FBS. The cells were infected with the recombinant baculovirus V-BAIT at a multiplicity of infection ("MOI") of about 2. Six hours later the medium was removed and replaced with SF900 II medium minus methionine and cysteine (available from Life Technologies Inc., Rockville, Md.). 42 hours later, 5 μCi of $^{35}$S-methionine and 5 μCi $^{35}$S-cysteine (available from Amersham) were added. The cells were further incubated for 16 hours and then harvested by centrifugation. The proteins in the supernatant as well as the intracellular proteins were analyzed by SDS-PAGE followed by autoradiography (if radiolabeled).

For production of unlabeled BAIT polypeptide, Sf9 cells were seeded in serum-free media at a density of $1.5 \times 10^6$ cells/ml in 200 ml spinner flasks. They were infected at an multiplicity of infection (moi) of 1 with the recombinant baculovirus encoding BAIT. At 96 hrs post-infection (pi), the cells were removed by centrifugation, and the conditioned media used as starting material.

Medium was diluted 1:1 (vol:vol) with 50 mM Na-Acetate PH 6.0 (Buffer A). The sample was applied to an HQ-50 column (Poros Resins, Perseptive Biosystems) at a flow rate of 30 mls/min. Bound protein was step-eluted with Buffer A containing 0.15, 0.35, 0.6 and 1.0 M NaCl and the fractions analyzed by SDS-PAGE. BAIT-containing fraction (350 mM step) were pooled, and diluted with Buffer A to a final NaCl concentration of 50 mM. This sample was applied to an HS-50 column (Poros Resins, Perseptive Biosystems) previously equilibrated with Buffer A plus 50 mM NaCl at a flow rate of 10 mls/min. Bound proteins were step eluted with Buffer A containing 1.0 M NaCl and fractions analyzed by SDS-PAGE. Finally, the pooled fractions were applied to an S-200 (Pharmacia) gel filtration column previously equilibrated with 50 mM Na-Acetate pH 6.5; 250 mM NaCl. BAIT-containing fractions eluted as a single peak which were pooled.

Protein concentration was determined using the Bio-Rad Protein Assay with BSA as a standard. Alternatively, the BCA Assay (Pierce) was used. The protein was 90% pure as judged by SDS-PAGE. The baculovirus produced protein was shown to be glycosylated and the isoelectric point (pI) of the protein was determined to be 5.0. This protein was used for in vitro activity assays described hereinabove. Microsequencing of the amino acid sequence of the amino terminus of the purified protein immediately after purification was used to determine the amino terminal sequence of the mature protein and thus the cleavage point and length (18 amino acids) of the secretory signal peptide, as shown in FIGS. 1A–1B (SEQ ID NO: 2). However, subsequent sequencing of the same preparation in another laboratory following storage at −80° C. for several weeks revealed an approximately equal molar mixture of the original mature species and a second species lacking one additional residue, i.e., with the N terminus ending with Thr at position 19 (and thus comprising amino acids 19–410 of SEQ ID NO: 2). Both species appeared to be efficiently cleaved upon interaction with tPA.

Example 3

Cloning and Expression in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC™ 37152), pSV2dhfr (ATCC™ 37146) and pBC12MI (ATCC™ 67109). Mammalian host cells that could be used include, human Hela, 293, H9 and Jurkat cells, mouse NIH3T3 and C 127 cells, Cos 1, Cos 7 and CV1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 22 7:277–279 (1991); Bebbington et al., *BiolTechnology* 10: 169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., Molecular and Cellular Biology, 438–447 (March, 1985)) plus a fragment of the CMV-enhancer (Boshart et al., Cell 41:521–530 (1985)). Multiple cloning sites, e.g., with the restriction enzyme cleavage sites BanHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pBAIT HA, is made by cloning a cDNA encoding BAIT into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., Cell 3–7:767 (1984). The fusion of the HA tag to the target protein allows easy detection and recovery of the recombinant protein with an antibody that recognizes the HA epitope. pcDNAIR contains, in addition, the selectable neomycin marker.

A DNA fragment encoding the BAIT is cloned into the polylinker region of the vector so that recombinant protein expression is directed by the CMV promoter. The plasmid construction strategy is as follows. The BAIT cDNA of the deposited clone is amplified using primers that contain convenient restriction sites, much as described above for construction of vectors for expression of BAIT in E. coli. Suitable primers include the following, which are used in this example. The 5' primer, containing the underlined BamHI site, a Kozak sequence, an AUG start codon and 18 nucleotides of the 5' coding region of the complete BAIT has the following sequence: 5' GAGCATGGATCCGCCAT-CATGGCTTTCCTTGGACTC 3'(SEQ ID NO:14). The 3' primer, containing the underlined BamHI site and 15 nucleotides complementary to the 3' coding sequence, has the following sequence: 5' GCACATGGATCCAAGTTCTTC-GAAATCATG 3' (SEQ ID NO:15).

The PCR amplified DNA fragment and the vector, pcD-NAI/Amp, are digested with BamHI, the vector is dephosphorylated and then the vector and amplified DNA are ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the BAIT-encoding fragment.

For expression of recombinant BAIT, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of BAIT by the vector.

Expression of the BAIT-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of BAIT protein. Plasmid pC4 is a derivative of the plasmid pSV2-dhfr (ATCC™ Accession No. 37146) The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J. Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, XbaI, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. CLONTECH™'s Tet-Off and Tet-On gene expression systems and similar systems can be used to express the BAIT in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and XbaI and then dephosphorylated using calf intestinal phosphates by procedures known in the art. The vector is then isolated from a 1% agarose gel. *J. Mol. Biol.* 196:947–950 (1987), and 24 bases of the coding sequence of BAIT shown in FIGS. 1A–1B (SEQ ID NO:1). The 3' primer has the sequence 5' GAGCATTCTAGAGTTGCAAACAT-AATGTGC 3' (SEQ ID NO:17) containing the underlined XbaI restriction site followed by 18 nucleotides complementary to the non-translated region of the BAIT gene shown in FIGS. 1A–1B (SEQ ID NO:1).

The amplified fragment is digested with the endonucleases BamHI and XbaI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using LIPOFECTIN™ liposome transfection reagent (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418.

After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

Example 4

Tissue Distribution of BAIT Protein Expression

Northern blot analysis is carried out to examine BAIT gene expression in human tissues, using methods described by, among others, Sambrook et al., cited above. A cDNA probe containing the entire nucleotide sequence of the BAIT protein (SEQ ID NO:1) is labeled with $^{32}P$ using the REDIPRIME™ DNA labeling system (Amersham Life Science), according to manufacturer's instructions. After labeling, the probe is purified using a CHROMA SPIN-100™ column (CLONTECH™ Laboratories, Inc.), according to manufacturer's protocol number PT1200-1. The purified labeled probe is then used to examine various human tissues for BAIT mRNA.

Multiple Tissue Northern (MTN) blots containing various human tissues (H) or human immune system tissues (IM) are obtained from CLONTECH™ and are examined with the labeled probe using EXPRESSHYB™ hybridization solution (CLONTECH™) according to manufacturer's protocol number PT1190-1. Following hybridization and washing, the blots are mounted and exposed to film at −70 C. overnight, and films developed according to standard procedures.

Example 5

Immunohistochemical Analysis of BAIT

To more precisely examine the expression of BAIT protein, immunohistochemical staining of adult mouse tissue sections was performed. Consistent with the mRNA distribution only brain and spinal cord tissues demonstrated significant reactivity. BAIT is widely distributed throughout the brain, but is primarily localized to neurons. The major exceptions to this pattern are expression in the ependymal cells of the choroid plexus, and the brush border of the cells lining the ventricles. These cells are thought to be of Microglial origin are important for maintaining the cerebrospinal and ventricular fluid. Other regions of the brain with high BAIT immunoreactivity are the Purkinji cells of the cerebellum which show strongly positive staining of the cell body as well as the axons. Most neurons of the spinal cord are also strongly positive, as are the axons in and the myelinated tracts of the commissura. Another region of strong staining is the hypothalamus where most of the neurons appear to show significant amounts of BAIT immunoreactivity within the cell body. Finally, BAIT was present in the large motor neurons of the medulla oblongata and in scattered neurons throughout the cortex.

Example 6

Comparison of BAIT Inhibitory Activity

A comparison of BAIT inhibitory activity and expression with that of PAI-1 and PN-1, suggests that BAIT has a biological role distinct from these other serpins. While BAIT reacts about 30-fold slower with tPA than does PAI-1, its rate of $6.2 \times 10^5$ $M^{-1}s^{-1}$ it is about 20-fold faster than that of PN-1. In addition, BAIT's primary target enzyme appears to be tPA, since its rate of inhibition of tPA is approximately 25-fold faster than is its rate of inhibition of uPA (Table 1). In contrast, PAI-1 inhibits uPA and tPA with essentially the same rate while PN-1 reacts with uPA about 5-fold faster than it does with tPA. Finally, unlike PAI-1 and PN-1, BAIT's inhibition of thrombin is not stimulated by heparin. Table I describes the kinetic constants for the interaction of BAIT with various proteinases.

TABLE I

| Enzyme | k (s$^{-1}$) | K (µM) | ki (M$^{-1}$s$^{-1}$) |
| --- | --- | --- | --- |
| tctPA | 0.078 | 0.12 | $6.2 \times 10^5$ |
| sctPA | 0.17 | 2.1 | $8.0 \times 10^4$ |
| Trypsin | 0.0096 | 0.16 | $5.9 \times 10^4$ |
| uPA-H | 0.0050 | 0.20 | $2.5 \times 10^4$ |
| uPA-L | 0.013 | 1.4 | $9.2 \times 10^3$ |
| NGF-γ | 0.0086 | 1.3 | $6.5 \times 10^3$ |
| PlasmiN | 0.000052 | 0.15 | $3.6 \times 10^2$ |
| Thrombin | 0.000131 | 0.64 | $2.1 \times 10^2$ |

The abbreviations are tctPA, human two-chain tPA: sctPA, human single-chain tPA, uPA-H, human high molecular weight uPA; uPA-L, human low molecular weight uPA; trypsin, bovine beta trypsin; and NGF-gamma, rat nerve growth factor gamma.

Example 7

BAIT Activity in Stroke Models

The present study demonstrates that BAIT is expressed in the area of ischemic penumbra in an animal model of focal cerebral ischemia/reperfusion. Moreover, intracerebral administration of BAIT after stroke decreases stroke volume, reduces basement membrane proteolysis, and diminishes the number of cells with apoptotic features in the area of ischemic penumbra. Thus, the data presented suggest that BAIT, a selective, naturally occurring inhibitor of tPA, may play an important role in neuronal survival after stroke.

Animal Preparation and surgery: Adult male Sprague-Dawley rats weighing 350–400 g were used. Anesthesia was induced with 4% halothane, 70% nitrous oxide and a balance of oxygen, and was maintained with 2% halothane and 70% nitrous oxide during the surgical procedure. Rats were intubated endotracheally and mechanically ventilated. Arterial blood pressure and blood gases were monitored. Body temperature was maintained at 37.5±0.5° C. with a warming blanket (Animal Blanket Control Unit, Harvard Apparatus) and controlled with a rectal thermistor and a probe inserted into the masseter muscle. Middle cerebral artery (MCA) was exposed and cauterized with a microbipolar coagulator (Non-Stick Bipolar Coagulation Forceps, Kirwan Surgical Products, Marshfield, Mass.) above its crossing point with the inferior cerebral vein as described elsewhere. Tamura A, et. al. J Cereb. Blood Flow Metab. 1981;1:53–60. Animals were then placed on a stereotactic frame and 20 µl of either 30 µM active BAIT in PBS, 30 µM inactive elastase-cleaved BAIT in PBS or 20 µl of PBS only was injected intracortically with a Hamilton Syringe through the burr hole. Comparison of untreated animals (no injection) to PBS-treated rats indicated that there was no significant difference in stroke volume, indicating that the injection itself did not contribute to the infarct size (data not shown). Following the intracortical injections, the left common carotid artery was exposed through a midline cervical incision and temporarily occluded for one hour with a microaneurysm clip (8 mm, 100 g pressure; Roboz Surgical Instruments Co., Rockville, Md.). Brint S, et. al. J Cereb. Blood Flow Metab. 1988;8: 474–485. Animals where then allowed to recover under the heating lamp, returned to their cages and given free access to water.

Figure 6:
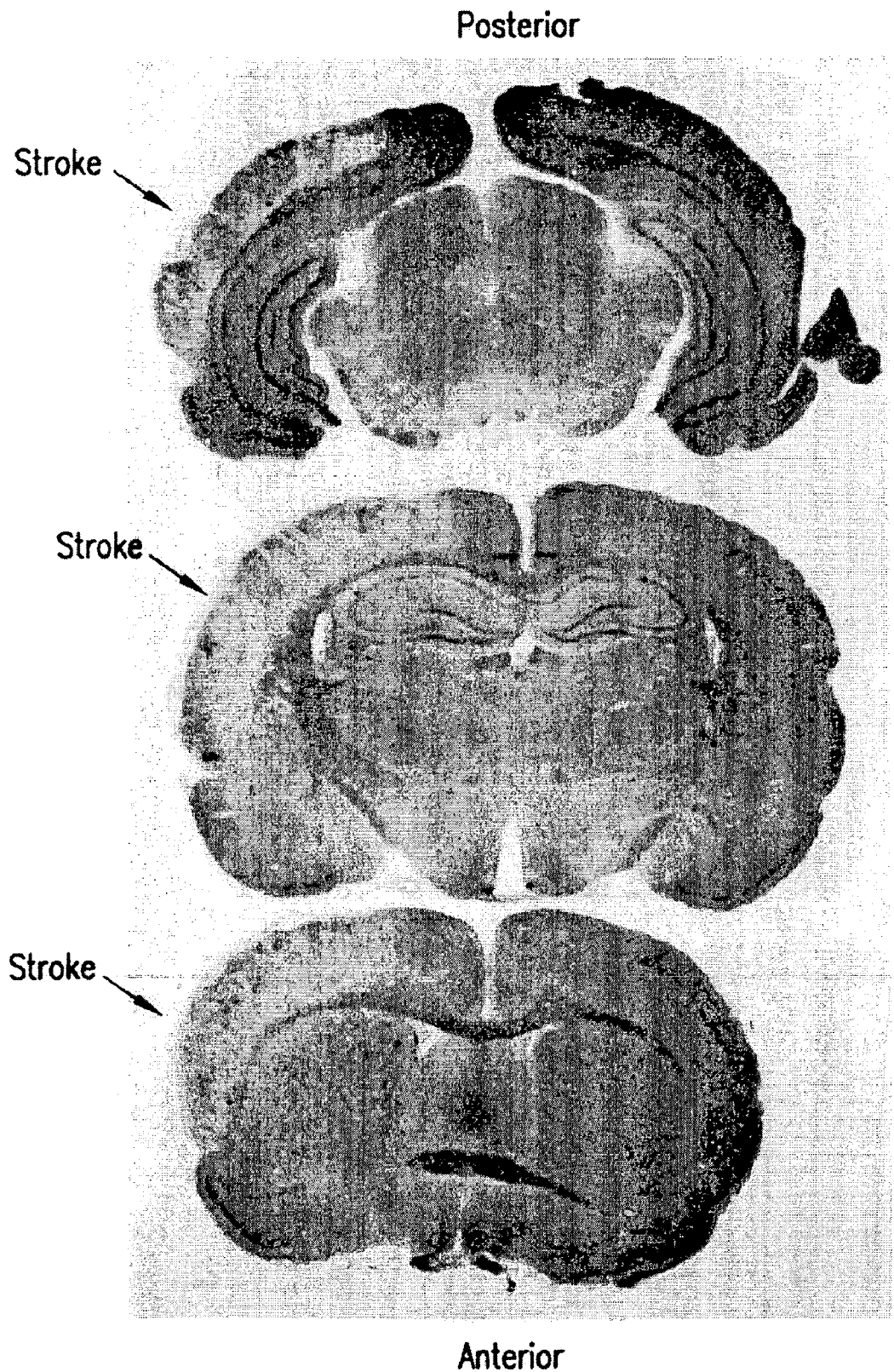
FIG. 6 shows rat brain sections 72 hours after reperfusion. Hematoxylin-eosin stain of three representative sections from the same brain 72 hours after reperfusion. The infarcted area is indicated with arrows, and the box indicates the location where higher resolution analysis was performed. Magnification is 5×.
Figure 7B:
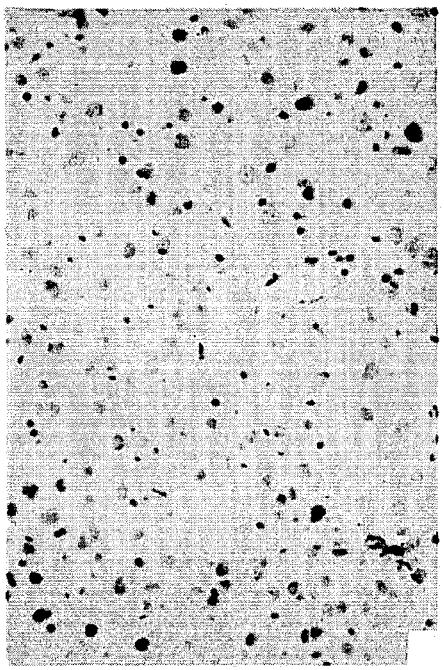
FIGS. 7A–D shows immunohistochemical staining of BAIT in brain 48 hours after reperfusion.
Figure 7D:
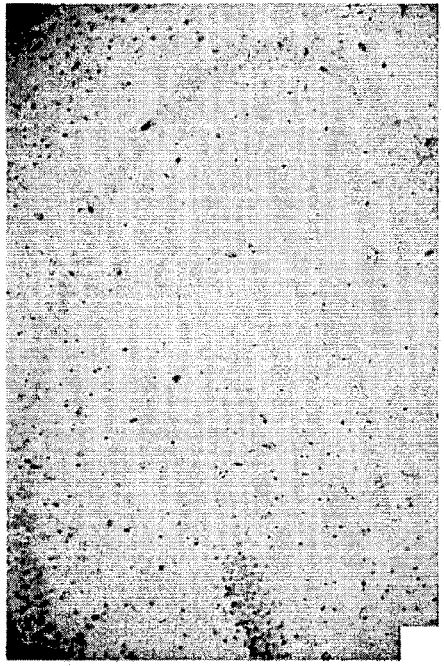
Figure 7A:
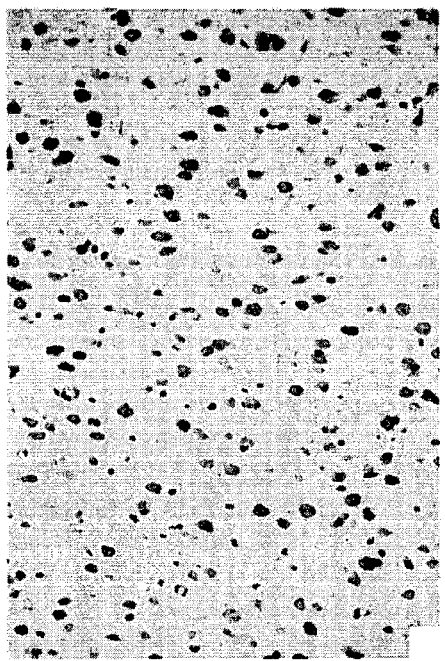
Figure 7C:
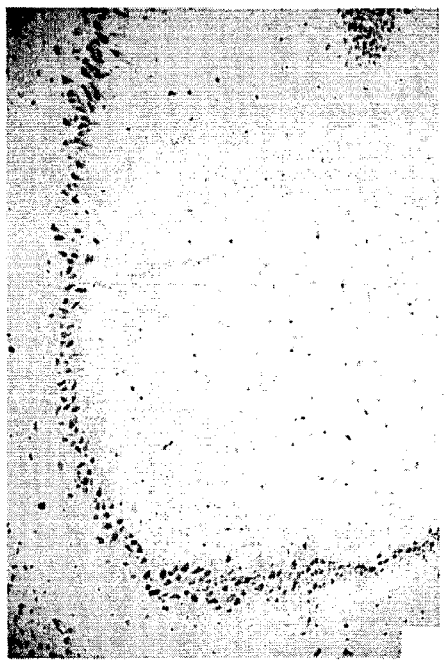

Infarct volume: Rats were anesthetized with pentobarbital i.p. 72 hours after infarction and brains were removed after transcardiac perfusion with PBS and parafomaldehyde 4% (Fisher Scientific, HC-200). The entire brain was embedded in paraffin and coronal sections, 20 μm thick, were cut through the rostrocaudal extent of the brain (FIG. 6). The sections were stained with hematoxilin-eosin and using the NIH Image Analyzer System, the total volume of each infarction was determined by the integration of the areas of eight chosen sections and the distances between them. The rostral and caudal limits for the integration were set at the frontal and occipital poles of the cortex. Osborne K A, et. al., J Neurol. Neurosurg. Psychiatry 1987;50:402–410. Statistical significance between groups of animals was identified by a Student's t-test.

TUNEL staining: Five μm paraffin-embedded sections from BAIT- and control-treated animals sacrificed at 6, 24, 48, and 72 hours after reperfusion were examined for TUNEL reactivity using the Apoptag Kit (Oncor, Gaithesburg, Md.). Paraffin sections were dewaxed, rehydrated and treated with proteinase K (20 μg/ml), and blocked for endogenous peroxidase activity with 3% $H_2O_2$. Subsequent end-labeling was done with TdT enzyme at 37° C. for 1 hour. Anti-digoxigenin peroxidase conjugate was applied to the tissue for 30 minutes at room temperature. The slides were developed with peroxidase substrate DAB for 5 minutes (Sigma, St. Louis, Mo.), washed in $dH_2O$ for 5 minutes and counter-stained with 0.5% methyl green for 10 minutes. To quantitate the presence of cells with apoptotic bodies, an area surrounding the ischemic core extending from the cerebral cortex to the most anterior (septal) part of the hippocampus was imaged in BAIT- and control-treated animals. Histologic features used by light microscopy to identify apoptosis depended upon recognition of dark-brown rounded or oval apoptotic bodies. MacManus J P, et. al., Neurosci. Lett. 1993;164:89–92; Li Y, et. al., Am. J Pathol. 1995;146:1045–1051. Statistical significance between groups of animals was identified by a Student's t-test.

Zymography: For SDS-PAGE zymography the region containing the stroke in brains from BAIT- and PBS-treated animals sacrificed at 6 and 72 hours after reperfusion were dissected and slices of approximately 600 mg were frozen in dry ice and stored at −70° C. A similar portion of brain was dissected from the same area in the contralateral hemisphere in both BAIT-treated and control animals. Protein extracts were prepared in 1.2 ml of extraction buffer as described. Hastings G A, et. al., J. Biol. Chem. 1997;272:33062–33067. The protein concentration was then determined, and 30 μg of extract (approximately 1 μl) was mixed with non-reducing sample buffer and subjected to SDS-PAGE on a 10% gel (Novex, San Diego, Calif.). Human tPA 0.3 ng (Genentech, San Francisco, Calif.) and a rat kidney extract containing uPA prepared in the same way as the brain extracts were included as positive controls and the identity of each PA was determined by including either anti-tPA or anti-uPA in the indicator film (data not shown). Following electrophoresis, the gel was soaked in 2.5% Triton X-100 for 2×45 min to remove the SDS. An indicator gel was prepared by mixing 1.25 ml of an 8% solution of boiled and centrifuged milk in PBS, 5 ml PBS and 3.75 ml of a 2.5% agar solution prewarmed at 50° C. Plasminogen (Molecular Innovations, Royal Oak, Mich.), was added to a final concentration of 30 μg/ml and the solution mixed and poured onto a pre-warmed glass plate. The Triton X-100 soaked gel was applied to the surface of the plasminogen-milk indicator gel and incubated in a humid chamber at 37° C. Milk indicator gel without plasminogen was also included as a control. The relative increase of tPA and uPA ipsilateral to the stroke at 6 hours after reperfusion was quantified by scanning a photograph of the SDS-PAGE zymography gel taken at an early time of development, before full lysis had occurred, and using the NIH Image Analyzer System. Normal baseline PA activities were calculated from the average of the activity present in 6 independent contralateral samples for which the coefficient of variation was <0.2%. Control analysis of purified tPA by this method demonstrated that lysis was linear over at least an 8-fold range with a Correlation Coefficient (r) of 0.994. Statistical significance between groups was identified by a Student's t-test.

For the in situ proteinase activity assay, brains from BAIT- and control-treated animals sacrificed at 6 and 72 hours after reperfusion (n=3 for each condition at each time point) were frozen in OCT and stored at −70° C. Eight μm cryostat sections were examined for plasminogen activator activity in overlays prepared as described. Sappino A P, et al., J. Clin. Invest. 1993;92:679–685. One hundred fifty μl of the overlay mixture was applied to pre-warmed tissue sections and spread under glass cover slips. Slides were incubated in a humid chamber at 37° C. and developed. Control sections were overlaid with a milk agar mixture without plasminogen. Other controls included those in which either 100 μg/ml anti-tPA (a generous gift of T. Podor, MacMaster University), or anti-uPA (Chemicon International, Temecula, Calif.) antibodies or 5 μM BAIT were included in addition to plasminogen.

Immunohistochemistry: All immunohistochemistry was performed on 5 μm deparaffinized-embedded sections. The sections were first immersed in methanol 0.3% $H_2O_2$ for 30 minutes and then either preincubated directly with 10% serum (either horse or goat), or first treated with 0.04% pepsin in 0.1N HCl for 20 minutes at 23° C. prior to being blocked with serum. All sections were also developed with the ABC reagent (Vector Laboratories, Burlingame, Calif.), using the DAB chromogen for 4 min, after which the sections were counter-stained with Mayer's hematoloxylin for 1 minute. For BAIT staining, adult male Sprague-Dawley rats that were not injected with BAIT or PBS, were sacrificed 6, 24, 48, 72, 96, or 168 hours after bipolar coagulation of the middle cerebral artery, or sham operation, and sections were prepared as above and stained with rabbit anti-human BAIT as described. Pulsinelli A., et. al., in Barnett H J M et al (ed): Stroke. Pathophysiology, Diagnosis and Management. New York, Churchill Livingstone; 1992: 49–68. For tPA, uPA and laminin, both control and BAIT treated animals, were examined. For tPA the sections were stained with affinity purified sheep anti-human tPA (a generous gift from Tom Podor, MacMaster University), at 1:800 dilution after pepsin digestion. For uPA goat anti-human uPA (Chemicon International-AB767, Temecula, Ca) was used at 1:200 dilution after pepsin digestion. For laminin staining a murine monoclonal anti-human laminin (Chemicon International-MAB2920, Temecula, Ca) was used at a 1:4000 dilution either with or without pepsin digestion as above. For all immunohistochemical analysis n≧2 for each condition at each time point except for BAIT staining at 96 and 168 hours for which n=1 each.

7(a)—BAIT expression after stroke: Since tPA may contribute to neuronal death following cerebral infarction, then increased expression of BAIT might play an important role in neuronal survival after stroke. To examine the expression of BAIT following cerebral ischemia, immunohistochemical staining of brain sections was performed at 6, 24, 48, 72, 96 and 168 hours after middle cerebral artery occlusion and reperfusion. FIG. 6 shows three representative brain sections harvested 72 hours after reperfusion and stained with hematoxilin-eosin. The infarct is clearly evident as the lighter stained tissue in the cortex of the left hemisphere, and the box indicates the area where higher resolution analysis was performed. BAIT immunoreactivity was seen to be increased in the area surrounding the ischemic core (penumbra) and in the ipsilateral hippocampus as early as 6 hours after stroke, and remained elevated up to 168 hours when compared with the contralateral, non ischemic, hemisphere or with sham operated controls (data not shown). The peak of BAIT immunoreactivity in both the number of BAIT positive cells, and in the intensity of the staining, appeared to be at 48 hours following reperfusion (FIGS. 7A–7D). The apparent rapid increase in BAIT expression following infarction suggests that the surrounding surviving cells may be upregulating BAIT expression in response to the ischemic insult.

Figure 8:
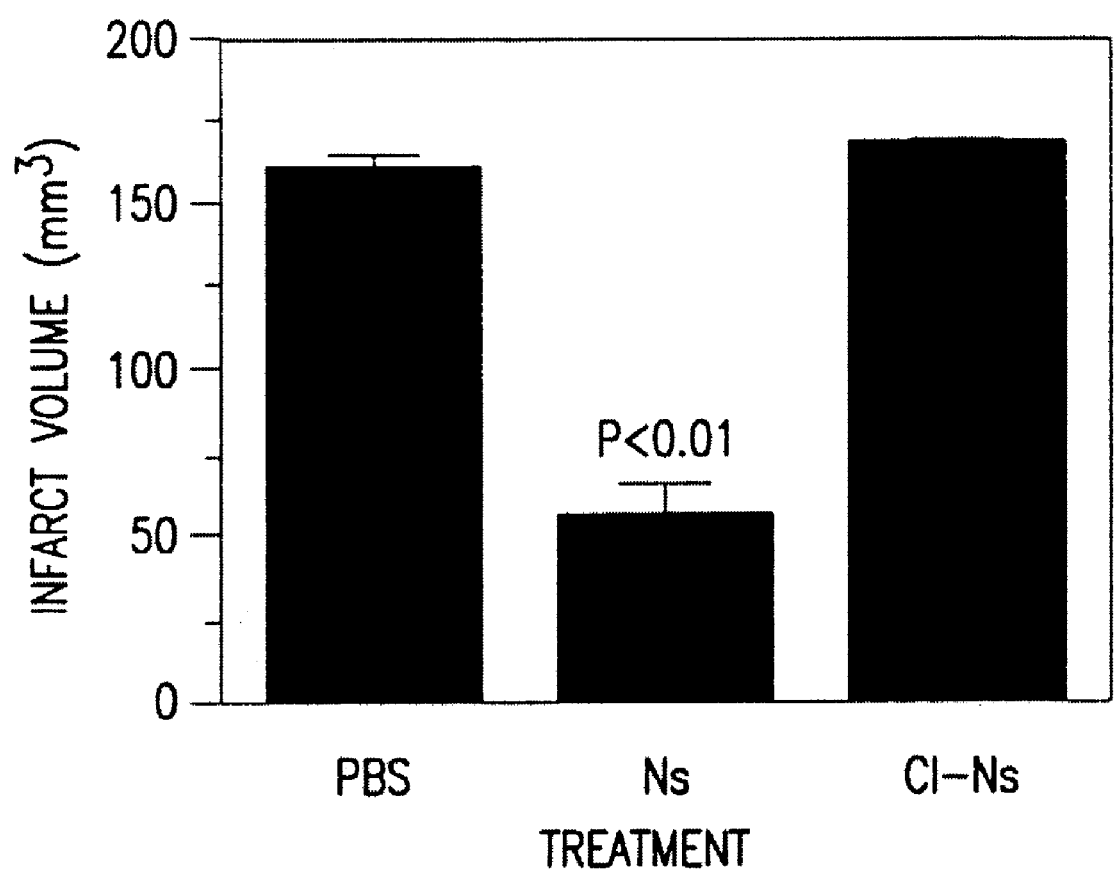
FIG. 8 shows quantitative analysis of infarct volume 72 hours after reperfusion. Quantitation of the stroke volume was performed as described in the Examples. PBS: animals injected with PBS (n=8); Ns: animals injected with BAIT (n=8): C1-Ns: animals injected with elastase-cleaved inactive BAIT (n=2). P values relative to the PBS-treated animals <0.01 are shown, and errors represent S.E.M.

7(b)—Effect of BAIT on stroke volume: To see if BAIT could reduce neuronal cell death after stroke with subsequent preservation of normal brain tissue, BAIT was administered intracerebrally immediately following MCA occlusion. Comparison of stroke volume between control and BAIT treated animals 72 hours after reperfusion indicated that intracortical injection of 30 μM BAIT reduced stroke size by 64%, from 161 mm$^3$ in control animals to 58 mm$^3$ in BAIT treated animals (FIG. 8). In contrast, stroke volume in animals treated with inactive BAIT, cleaved in its reactive center loop, showed no decrease in stroke size relative to control animals, suggesting that active BAIT is required to reduce stroke volume (FIG. 8).

Figure 9B:
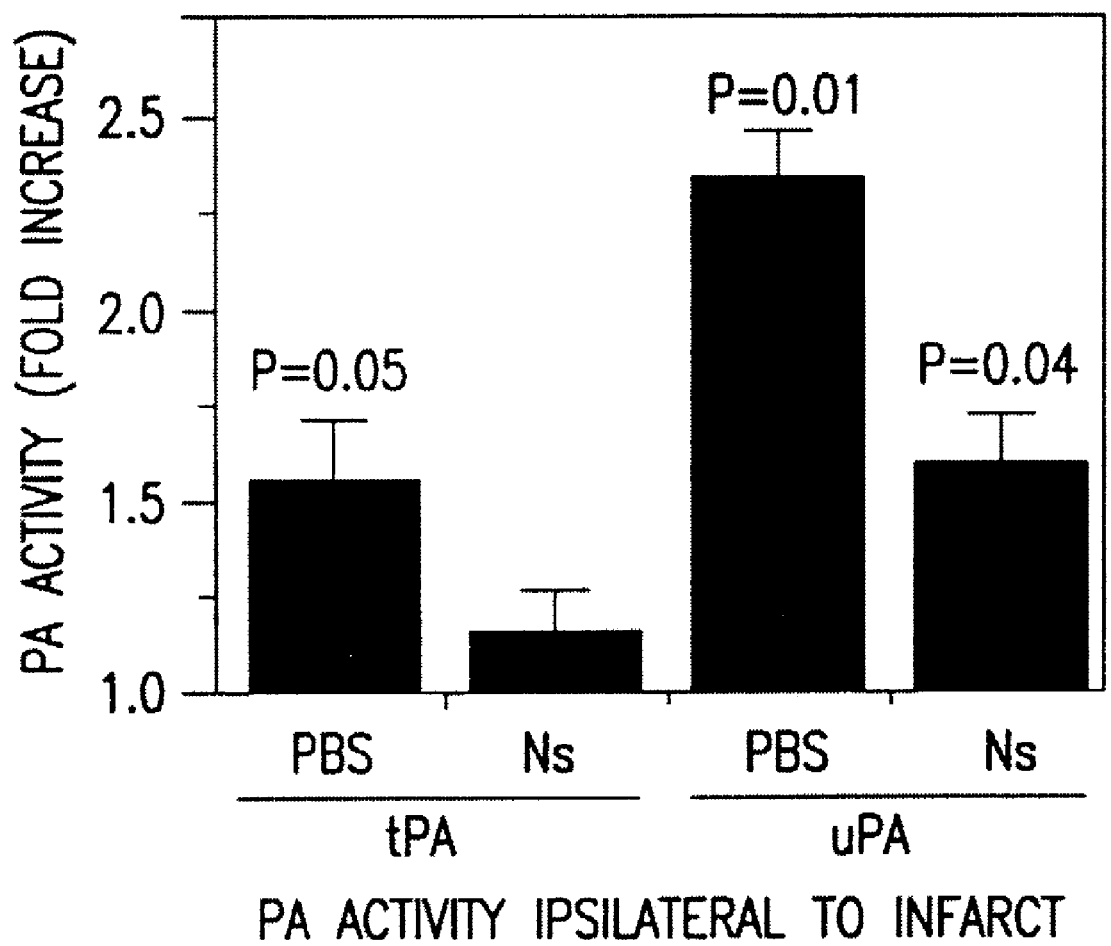

7(c)—Proteinase activity after stroke: Since only the active inhibitory form of BAIT reduced stroke volume, this suggests that BAIT acts primarily by blocking proteinase activity, possibly tPA activity. To examine proteinase activity following stroke, and to determine the effect of BAIT treatment on proteinase activity, two different assays were utilized. The first, SDS-PAGE zymography, was performed on extracts of tissues dissected from the cortex, either ipsi- or contralateral to the stroke of both PBS- and BAIT-treated animals (FIG. 9A). Following electrophoresis and removal of SDS, the gels were overlaid onto milk-agarose gels with or without plasminogen. In the absence of plasminogen no proteinase activity could be detected in any of the extracts, whereas addition of plasminogen to the milk-agarose mixture demonstrated that both tPA and uPA activity were present in all cortex extracts examined, including those from sham operated animals (data not shown). Examination of extracts prepared from animals 6 hours following reperfusion suggested that both tPA and uPA activity were elevated ipsilateral to the stroke in PBS-treated animals, but that only uPA appeared to be elevated in BAIT-treated brains (FIG. 9A). However, by 72 hours tPA activity appeared to return to baseline, indicating that the increase in tPA activity is transient and that BAIT can reduce the extent of this increase. In contrast, uPA-catalyzed activity, which was relatively low in the 6-hour extracts, increased dramatically in ipsilateral extracts of animals sacrificed 72 hours after reperfusion, and this increase was apparent in both control and BAIT-treated brains. However, like both tPA and uPA at 6 hours, the amount of uPA activity at 72 hours was significantly lower in BAIT-treated animals compared to controls (FIG. 9A). Quantitative image analysis of these data indicated that by 6 hour following reperfusion ipsilateral to the stroke in PBS-treated animals there was an approximately 50% increase in tPA activity and an approximately 125% increase in uPA activity relative to baseline levels (FIG. 9B). However, in BAIT-treated animals the increase of both PAs ipsilateral to the stroke was markedly reduced, showing only an approximately 50% increase for uPA and no significant increase in tPA compared to baseline levels (FIG. 9B). These results indicate that there is an early and transient increase in tPA activity ipsilateral to the stroke, and that BAIT is able to block this increase. Similarly, there is an early increase in uPA activity ipsilateral to the stroke, but in contrast to tPA this increase is not transient and continues to rise at least up to 72 hours after reperfusion, and is not blocked by treatment with BAIT but is only reduced compared to the PBS-treated animals.

Figure 10C:
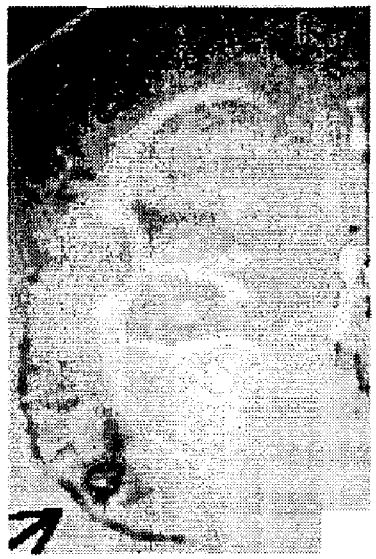
FIGS. 10A–10H show in situ zymography and immunohistochemical staining of brain sections. In situ zymography in FIGS. 10A–F.
Figure 10B:
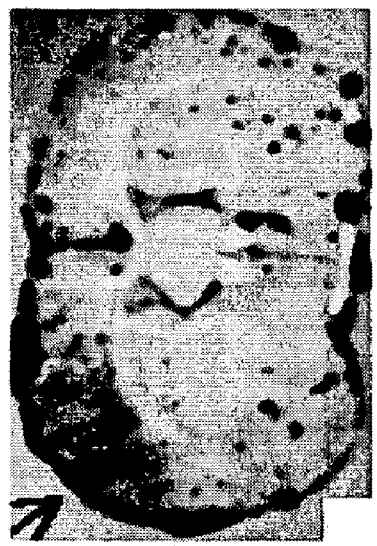
Figure 10A:
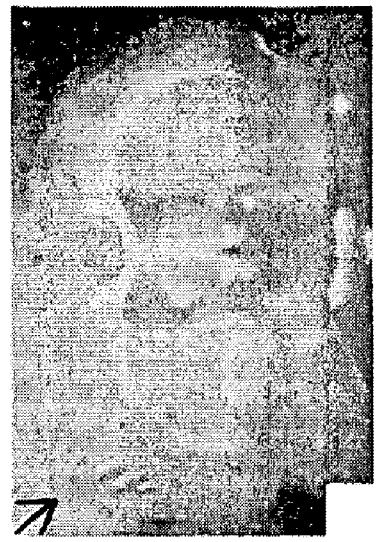
Figure 10F:
Figure 10E:
Figure 10D:
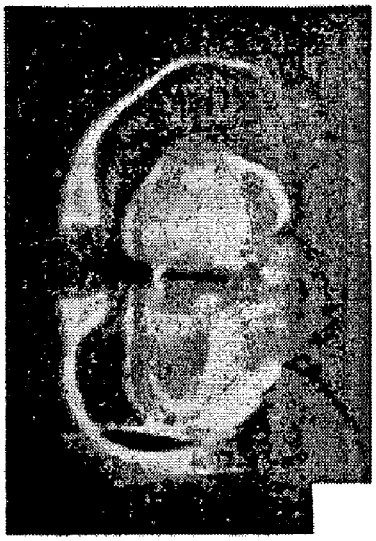

To examine the distribution of proteinase activity within the brains of the PBS- and BAIT-treated animals, in situ zymography of frozen brain sections was performed. These data demonstrate that like the SDS-PAGE zymography, all of the proteolytic activity detected in both control and BAIT treated brains was plasminogen-dependent, since no proteinase activity was observed in the absence of plasminogen (FIGS. 10A & 10D). At 6 hours following reperfusion, proteinase activity in all sections was primarily associated with the meningeal tissues of both ipsi- and contralateral sides. This activity was also completely blocked by the addition of anti-tPA antibodies indicating that the majority of PA activity within the brain at this time is tPA (data not shown). In contrast, by 72 hours following reperfusion, there was a large increase in plasminogen-dependent proteolytic activity ipsilateral to the stroke in control animals (FIG. 10B), and unlike the 6 hour sections or the 72 hour contralateral side, this activity was not restricted to the meninges and was not completely blocked by the addition of anti-tPA antibodies to the plasminogen overlay (arrows in FIGS. 10B–C). In BAIT-treated animals this zone of proteinase activity was significantly smaller than in the untreated animals (FIGS. 10E–F). This suggests that by 72 hours much of the plasminogen dependent activity within the region of the stroke was not tPA. Consistent with this, the addition of anti-uPA antibodies to the plasminogen overlay markedly reduced proteolysis within the area of the stroke while having no effect on the proteolytic activity in the meningeal tissues contralateral to the stroke (data not shown). This implies that within the area of the infarct at 72 hour following reperfusion there is a significant increase in uPA activity. These results also suggest that there is not a large up-regulation of either tPA or uPA immediately following stroke, however, by 72 hours after reperfusion, uPA-catalyzed proteolysis is significantly increased specifically within the region of the infarct. These results are also consistent with the SDS-PAGE zymography, and suggest that the lesser increase in uPA activity observed by SDS-PAGE zymography in BAIT-treated animals, may simply reflect the smaller size of the infarct in this group and not a direct inhibition of the up-regulation of uPA-activity by BAIT.

Figure 10H:
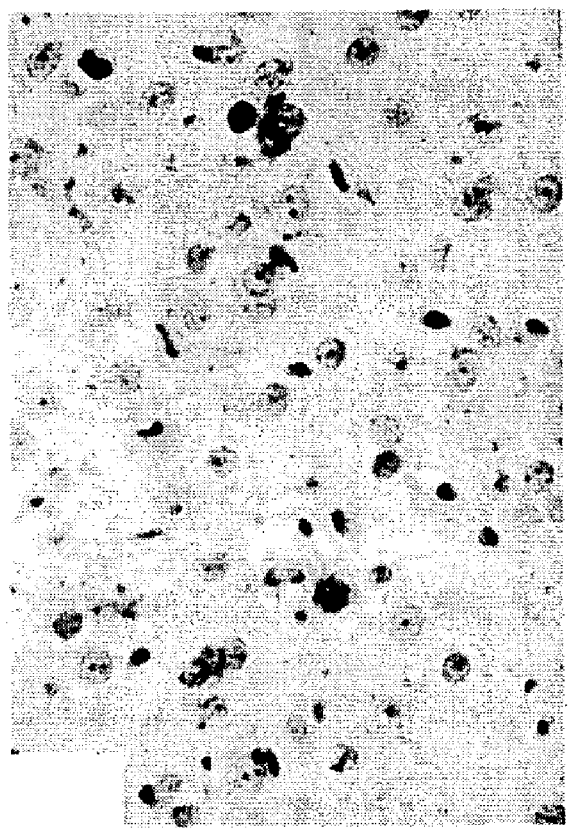
Figure 10G:

Immunohistochemical staining for tPA indicated that by 6 hours following reperfusion, tPA antigen was detected only within the vascular endothelial cells and not within neuronal cells (FIG. 10G). Consistent with the relatively low levels of uPA activity at 6 hours, no uPA staining could be detected in these sections (data not shown). However, by 72 hours after reperfusion, uPA immunoreactivity was readily detected, but only in the area of ischemic penumbra (FIG. 10H). This is consistent with the in situ zymography analysis demonstrating uPA activity predominantly within the cortex and only at 72 hours after reperfusion. Finally, at 72 hours in BAIT-treated animals, there was a marked reduction in the overall area where uPA antigen was detected but not in the intensity of the staining, compared to PBS-treated animals (data not shown). This further suggests that the reduced uPA activity observed by zymography was likely due to the reduced size of the infarct in BAIT-treated animals.

Figure 11B:
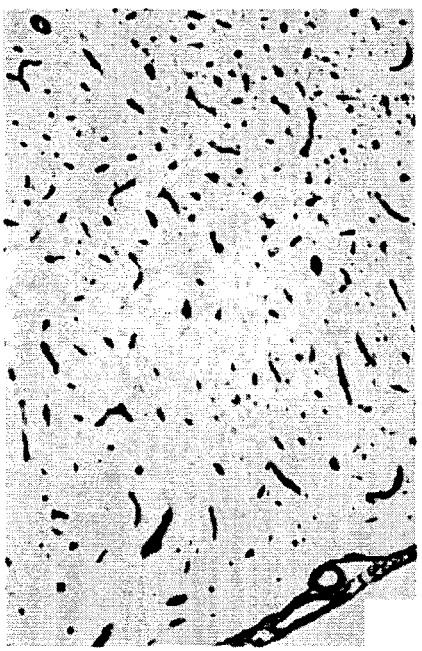
FIGS. 11A–11F show immunohistochemical staining of laminin.
Figure 11D:
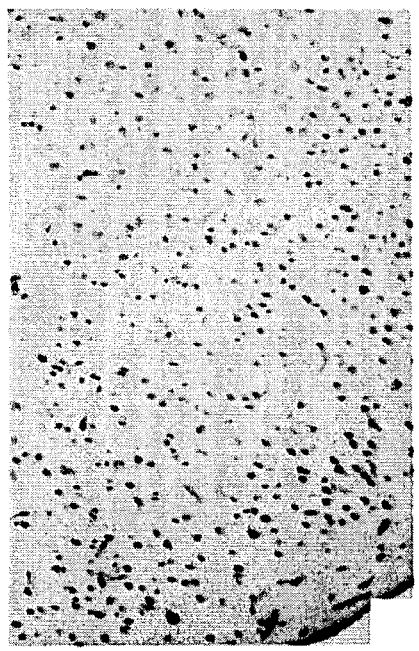
Figure 11A:
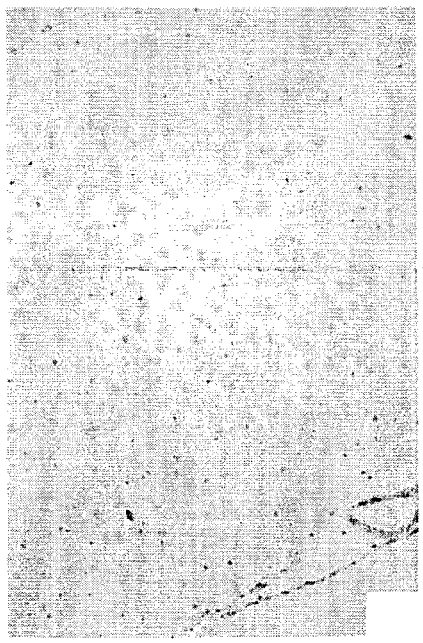
Figure 11C:
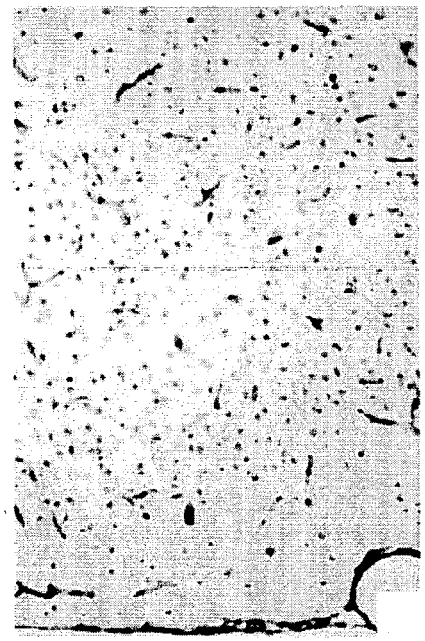
Figure 11F:
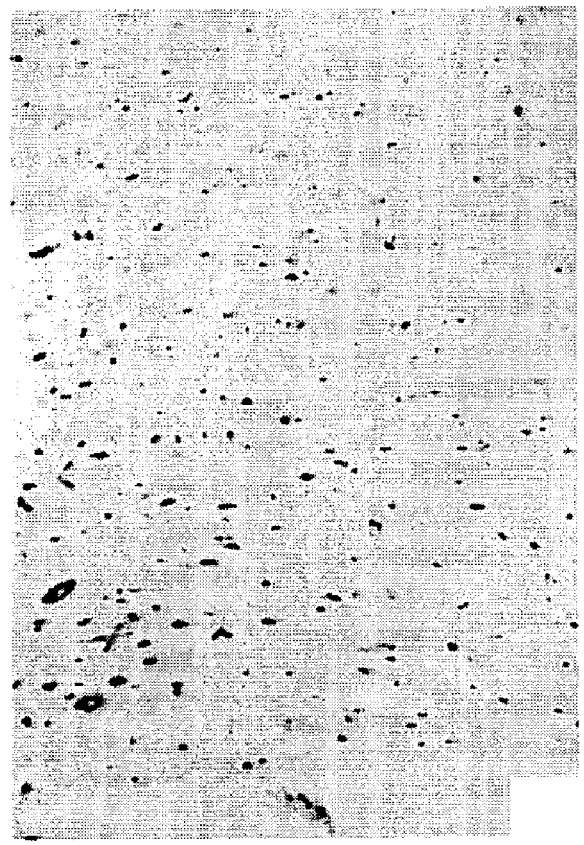
Figure 11E:
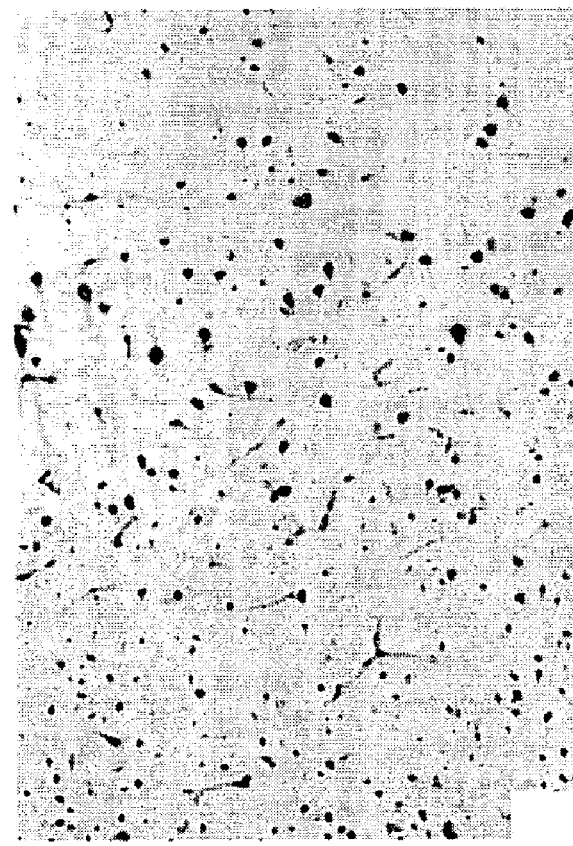

Basement membrane degradation after cerebral ischemia: Since excitotoxin-induced laminin degradation has been suggested to be mediated by tPA and to precede apoptotic cell death, we examined the effect of stroke on laminin immunoreactivity. For this analysis we utilized a monoclonal antibody that does not react strongly with rat laminin in fixed tissue unless the tissue is first proteolyzed to expose cryptic laminin epitopes. This is shown in FIGS. 11A and 11B, where FIG. 11A shows a section of un-proteolyzed rat cortex reacted with the antibody, and FIG. 11B shows an adjacent section that was first treated with proteinase in vitro before reaction with the antibody. These results indicate that in the absence of proteolysis this antibody does not react with vascular laminin. However, after proteolysis there is a strong reaction that appears to be localized to the vessels. Thus this antibody provides an excellent tool to probe for partial proteolysis of the basement membrane within fixed brain tissue. Examination of laminin staining in cortical tissue as early as 10 min. after reperfusion indicated that even at this early time there was apparently significant proteolysis of the basement membrane in control animals (FIG. 11C). However, in BAIT treated animals the extent of laminin proteolysis was significantly reduced such that only slight staining of the vascular laminin was apparent (FIG. 11D). This latter result was not due to the absence of laminin in this tissue since treatment of the sections with proteinase in vitro yielded staining indistinguishable from that shown in FIG. 11B (data not shown). Vascular laminin staining was also observed at 6 hours after reperfusion in control animals and, similar to the results at 10 minutes, treatment with BAIT significantly reduced this staining (FIGS. 11E–F). Furthermore, by 6 hours after reperfusion laminin staining was also observed within neurons in the area of cerebral ischemia and, as with vascular laminin staining, was reduced by BAIT treatment (FIGS. 11E–F). The neuronal staining most likely represents new synthesis of laminin since in control animals not subjected to stroke no laminin staining was observed in neurons either with or without proteinase treatment (FIGS. 11A–B). Laminin staining remained strong at 24 and 48, but started to decrease by 72 hours. Also, at each time point the BAIT treated animals showed significantly less immuno-reactivity than control animals (data not shown). These data suggest that there is a very early proteolytic event that appears to act on the vascular basement membrane, and that BAIT treatment is able to reduce this proteolysis.

Figure 12A:
FIGS. 12A–12E show neuronal apoptosis within the ischemic penumbra. TUNEL staining ipsilateral of the infarct in PBS-treated (FIGS. 12A & 12B) and BAIT-treated (FIG. 12C) animals.
Figure 12B:
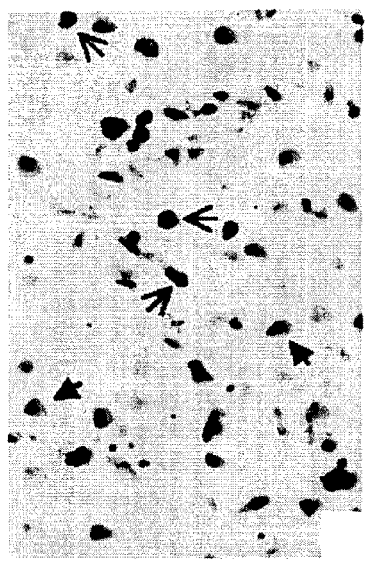
Figure 12C:
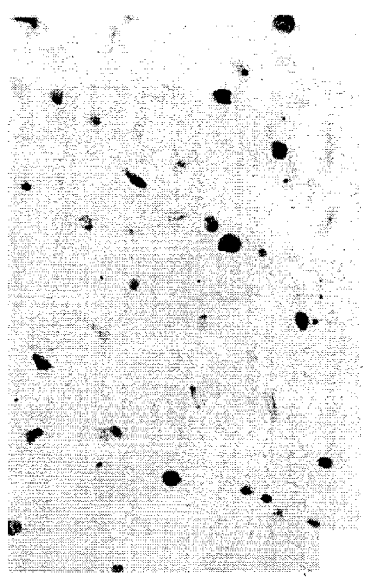
Figure 12D:
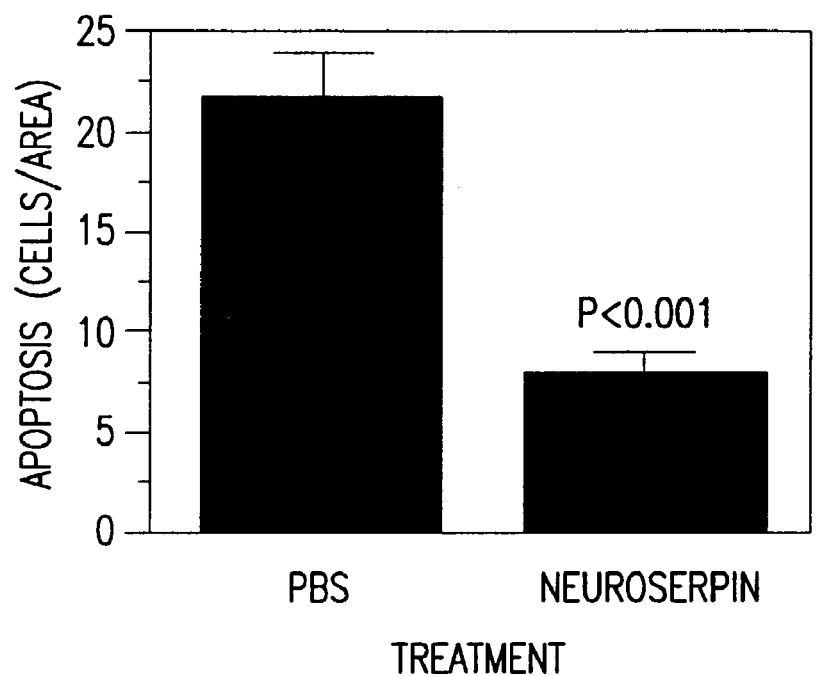
Figure 12E:
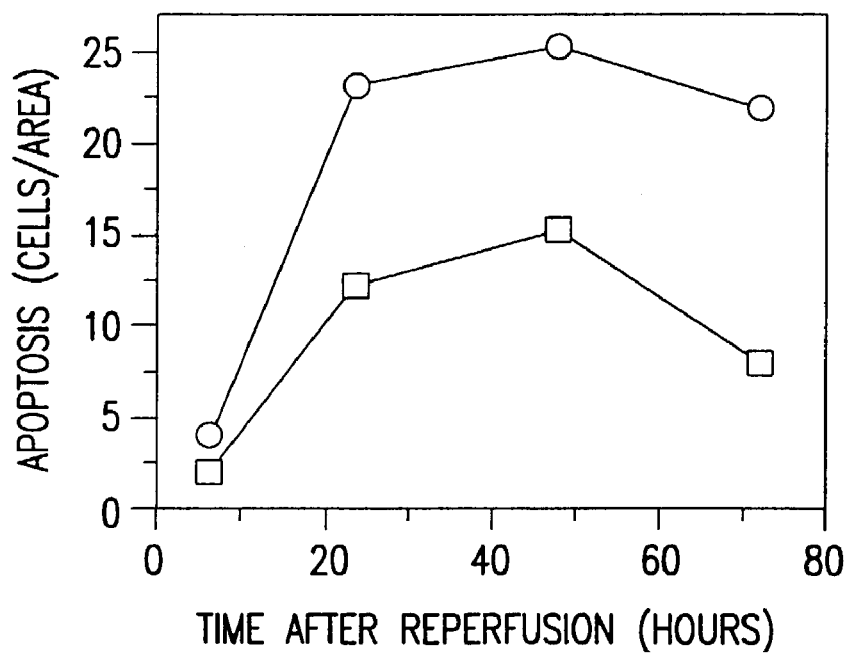

Apoptosis: Since cerebral ischemia has been suggested to induce apoptosis in the ischemic penumbra, then a good therapeutic strategy aimed at reducing cell death after stroke should target the recovery of cells in this area. To see if BAIT reduced infarct volume by preventing penumbral apoptosis, tissue from untreated and BAIT treated animals was stained by the TUNEL method (FIGS. 12A–C). The extent of apoptosis in these sections was then quantified as described above and these data are shown in FIG. 12D. The number of cells within a defined area of the penumbra with apoptotic bodies after 72 hours of cerebral ischemia was 22±5 in untreated animals and decreased to 8±2 in BAIT-treated animals (FIG. 12D). This indicates that BAIT significantly inhibits penumbral apoptosis. To see if BAIT also blocked cell death at earlier times, apoptosis was also quantified at 6, 24, and 48 hours. These data indicate that at all times examined apoptosis was reduced by at least 50% with BAIT treatment (FIG. 12E). Finally, in order to test if BAIT had a direct effect on apoptosis, two independent assays were performed. In the first, BAIT was tested for its ability to block T-cell receptor mediated apoptosis of a T-cell hybridoma in vitro. In the second assay BAIT was tested for its ability to directly inhibit caspase activity in extracts of B lymphoma cells treated with anti-Fas IgG to induce apoptosis and caspase activation. In both assays BAIT had no effect on either apoptosis or caspase activity (data not shown). Taken together, these results indicate that BAIT is not a direct inhibitor of apoptosis, and therefore, it is likely that BAIT blocks events prior to induction of apoptosis.

Discussion. BAIT, a natural inhibitor of tPA, is found almost exclusively within the central nervous system, and shows an early and significant increase in its expression within the area of ischemic penumbra in response to stroke (FIGS. 7A–7D). Cerebral ischemia is known to induce neuronal depolarization, as well as release of excitotoxins, which in turn trigger the release of tPA. Since tPA may be associated with increased neuronal loss in response to both ischemia and excitotoxins, then the increased local expression of BAIT following ischemia may represent an innate protective response to elevated tPA levels, and suggests that BAIT may be a naturally occurring neuronal survival factor. Consistent with this hypothesis, BAIT-treatment resulted in a significant decrease in stroke volume relative to control animals. Furthermore, only functionally active BAIT was able to reduce infarct size, suggesting that inhibition of proteinase activity was necessary for BAIT's neuroprotective effects (FIG. 8).

Zymographic analysis of brain extracts at 6 and 72 hours after reperfusion indicated that there was an early rise in both tPA and uPA activity in the area of the infarct in control animals, and that treatment with BAIT significantly reduced these activities (FIGS. 9A–9B). These data are similar to earlier results that reported an increase in uPA activity in both rats and mice following cerebral ischemia, and to at least one other study that reported a significant increase in tPA activity. However, in two studies tPA activity following stroke was reported to be either decreased, or unchanged. The apparent difference in the activity of tPA noted here compared to these earlier studies may in part reflect the time after cerebral ischemia when tPA was measured since our data suggest that the increase in tPA activity is transient and since none of these other studies measured tPA at six hours following reperfusion. These differences might also be due to the different animal models used in the various studies. For example, the model used here creates a permanent occlusion of the middle cerebral artery at its crossing point with the inferior cerebral vein with reperfusion provided by temporary clamping of the left carotid artery. This produces an ischemic injury in a very well defined area of the cerebral cortex (FIG. 6), and in contrast to the intravascular filament model (Longa E Z, et. al., Stroke 1989;20:84–91), avoids the potential of large lesions to the vascular endothelium and severe disruption of the blood-brain barrier that could lead to significant changes in the local tPA activity. Nonetheless, our results and those of Wang et al (Wang Y F, et. al. Nat Med. 1998;4:228–231) suggest that there is an early local increase in tPA activity in the area of the infarct, and the data reported here further suggest that this increase is transient. Since treatment with functionally active BAIT reduced both the local increase in tPA activity as well as the infarct size, it is possible that these two effects are related, and that by blocking the action of tPA very early after reperfusion the later increase of the infarcted area is prevented.

In contrast to tPA, uPA activity increased to very high levels by 72 hours following reperfusion, and was localized almost exclusively to the ischemic penumbra (FIGS. 9A–9B & FIGS. 10A–10H). The role of uPA after cerebral ischemia is largely unknown. However, since the necrotic core is already well defined by 72 hours after the stroke, it is unlikely that the late increase in uPA activity plays an important role in the development of the infarct. This inference is also consistent with a recent study of stroke in uPA deficient mice that indicated that there was no difference in infarct volume between wild-type and uPA-/- mice 24 hours after reperfusion. However, since uPA has been demonstrated in both glial cells during myelination and in mature cortical neurons (Del Bigio M R, et. al., Brain Res. Dev. Brain Res. 1995;86:345–347), the late expression of uPA activity and antigen suggests that uPA could participate in the process of neuronal recovery after stroke as was suggested by Rosenberg et al. (Rosenberg G A, et. al., J Cereb. Blood Flow Metab. 1996;16:360–366).

Although the role of tPA activity in infarct evolution is not well understood, tPA induced plasmin cleavage of basement membrane laminin has been suggested to play a role in excitotoxin induced neuronal death within the hippocampus and in the disappearance of basement membrane antigens following ischemia and reperfusion. The basement membrane is a specialized part of the extracellular matrix that connects the endothelial cell compartment to the surrounding cell layers. Laminins are very important components of the basement membrane, playing a pivotal role in cell-extracellular matrix interactions, including promotion of neurite outgrowth, cell attachment, proliferation, and differentiation, as well as in the development, and regeneration of the nervous system. Paulsson M, Crit. Rev. Biochem. Mol. Biol. 1992;27:93–127; Calof A L, et. al., Neuron 1994;13: 117–130; Hammarback J A, et. al., Dev. Biol. 1988;126: 29–39; Liesi P, EMBO J. 1985;4:2505–2511; Millaruelo A I, et. al., Brain Res. 1988;466:219–228. In the present study exposure of cryptic laminin epitopes within the basement membrane was observed within 10 minutes of reperfusion, suggesting that there is proteolytic activity acting on the basement membrane very early following cerebral ischemia (FIGS. 11A–11F). Like the observed increase in tPA, this activity appears to be transient with peak epitope exposure occurring within 6–24 hours of reperfusion. Whether this effect is due to the direct action of tPA on laminin, is mediated through plasmin, or involves MMPs or other as yet unidentified proteinases is not clear. Regardless of which proteinase is responsible for the apparent basement membrane degradation, the extent of laminin epitope expression was significantly decreased in BAIT-treated animals (FIGS. 11A–11F). This suggests that BAIT is inhibiting the proteolytic attack on the basement membrane, most likely by inhibiting tPA. Thus, BAIT, by blocking the early increase in tPA activity, may be able to preserve the integrity of the basement membrane and thus the blood brain barrier after stroke.

It is known that disruption of cell-matrix interactions can lead to apoptosis. Meredith J E J, et. al. Mol. Biol. Cell 1993;4:953–961; Murtomaki S, et. al., Dev. Biol. 1995;168: 635–648. Since the cryptic laminin epitopes were observed as early as 10 minutes after reperfusion, with high levels of neuronal expression seen by 6 hours (FIGS. 11A–11F), well before 24–48 hours, the peak of apoptosis (FIG. 12E), this suggests that the proteolytic disruption of the basement membrane may be the trigger that initiates the program of apoptotic neuronal cell death. Thus, the capacity of active BAIT to block tPA-induced degradation of the basement membrane may explain the ability of BAIT treatment to reduce neuronal apoptosis by nearly 70% (FIG. 12D). Finally, although it has been demonstrated that apoptotic cell death in stroke is mediated by proteinases known as caspases (Barinaga M, Science 1998;280:32–34; Cheng Y, et. al., J. Clin. Invest. 1998;101:1992–1999; Namura S, et. al., J. Neurosci. 1998;18:3659–3668), BAIT failed to inhibit either caspase activity or T-cell apoptosis, suggesting that BAIT is not an inhibitor of apoptosis per se and does not directly block caspase activation or activity.

Intra-neuronal laminin-like immunoreactivity has been reported in both the developing and adult central nervous system, and in astrocytes after transient ischemia. Suzuki H, et. al., Brain Res. 1990;520:324–329; Jucker M, et. al., Ann. N.Y. Acad. Sci. 1993;679:245–52:245–252. Laminin has also been shown to promote neurite outgrowth. We observed morphologically healthy neurons that were positive for intracellular laminin staining in the area of penumbra in control animals by 6 hours after reperfusion (FIG. 11E), suggesting a role for intraneuronal laminin in neuronal maintenance following ischemia. It is possible that synthesis of laminin by neurons is in response to laminin degradation within the basement membrane, and that BAIT treated animals show fewer laminin positive cells because there is less basement membrane degradation and thus many fewer distressed cells. It is interesting to note that the region of the cortex that shows many laminin positive cells at six hours after reperfusion is the same region that shows many apoptotic cells at 48 hours. This suggests that if laminin expression is an early marker for cell distress then BAIT treatment must be acting very early in the pathway that leads to neuronal apoptosis.

Taken together the data presented here suggest a model for stroke induced neuronal death within the ischemic penumbra, and demonstrate the potential therapeutic benefits of BAIT in this setting. We speculate that one of the first potentially deleterious events to occur is the release of tPA by the vascular endothelial cells in response to the acute ischemia. If there is also increased vascular permeability at this time as a result of damage to the blood-brain barrier, then this will allow tPA to cross from the lumen of the vessel into to the subvascular space, where it can bind directly to laminin. This inappropriately targeted tPA can then, either by itself or in concert with other proteinases such as plasmin, or MMPs begin to degrade the basement membrane. This leads to a further increase in vascular permeability, which in turn may accelerate the degradation of the blood brain barrier. In addition, neuronal cells that are also dependant upon the integrity of the basement membrane may begin to loose their contacts with the substrate, which in itself might induce a program of apoptosis as has been described for other cell types. Our data also suggest that by approximately 72 hours after the stroke onset the basement membrane degradation and neuronal apoptosis have decreased, stabilizing the lesion. At this time other factors such as uPA are up-regulated possibly as part of the recovery process. BAIT treatment, by blocking the early effects of proteinase activity, may help to maintain the integrity of the basement membrane, preventing further passage of tPA or other potentially harmful blood born factors to the subvascular space.

BAIT may also directly prevent neuronal loss by helping to preserve neuronal contacts to the basement membrane.

Moreover, BAIT polypeptides (including N & C terminal mutants, variants, and antibodies described herein) and polynucleotides may also be used to treat cerebrovascular disorders, such as carotid artery disease, cerebral amyloid angiopathy, cerebral aneurysm, cerebral anoxia, cerebral arteriosclerosis, cerebral arteriosclerosis, cerebral arteriovenous malformations, cerebral artery disease, cerebral embolism, cerebral thrombosis, cerebral hemorrhage (e.g., hematoma), cerebral infarction, cerebral ischemia (e.g., transient cerebral ischemia, subclavian steal syndrome, and vertebrobasilar insufficiency), vascular dementia, leukomalacia, vascular headache (e.g., cluster headache, migraine), and/or strokes.

Additionally, BAIT polypeptides (including N & C terminal mutants, variants, and antibodies) and polynucleotides described herein) may be used to inhibit tPA and/or increase uPA. Also, BAIT polypeptides (including N & C terminal mutants, variants, and antibodies) and polynucleotides may be used to activate tPA and/or deacrease uPA.

Furthermore, polypeptides (including N & C terminal mutants, variants, and antibodies) and polynucleotides may be used to treat brain diseases caused by a variety etiologies. For example, polypeptides (including N & C terminal mutants, variants, and antibodies) and polynucleotides may be used to treat akinetic mutism, auditory diseases, basal ganglia diseases (e.g., Huntington's Disease, Parkinson Disease, or Alzheimer's Disease), brain abscess, chronic brain damage (e.g., cerebral palsy), metabolic brain diseases (e.g., abetalipoproteinemia, PKU, Lesch-Nyan Syndrome), brain edema, and brain neoplasms. Similarly, BAIT may be used to treat cerebellar diseases (e.g., ataxia), and cerebral sclerosis, dementia, encephalitis, encephalomalacia, epilepsy, Hallervorden-Spatz Syndrome, hydrocephalus, hypothalamic disease, malaria, narcolepsy, poliomyelitis, pseudotumor cerebri, Rett Syndrome, Reye's Syndrome, Thalamic Disease, Toxoplasmosis, Intracranial Tuberculoma, and Zellweger Syndrome. Thus, diseases of the brain and the nervous system may be treatable using polypeptides (including N & C terminal mutants, variants, and antibodies) and polynucleotides.

Example 8

Production of an Antibody

Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide (s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC™. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 $E.$ $coli$ harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 µg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 µg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 9

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Examples above; see also EP A 394,827; Traunecker, et al., Nature 331:84–86 (1988).) Similarly, fusion to IgG-1, IgG-3, and albumin increases the halflife time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule, or the protocol described in the Examples.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector.

For example, if pC4 (Accession No. 209646) is used, the human Fc portion can be ligated into the BamHI cloning site. Note that the 3' BamHI site should be destroyed. Next, the vector containing the human Fc portion is re-restricted with BamHI, linearizing the vector, and a polynucleotide of the present invention, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc region:

(SEQ ID NO:18)
GGGATCCGGAGCCCAAATCTTCTGACAAAACTCACACATGCCCACCGTGC

CCAGCACCTGAATTCGAGGGTGCACCGTCAGTCTTCCTCTTCCCCCCAAA

ACCCAAGGACACCCTCATGATCTCCCGGACTCCTGAGGTCACATGCGTGG

TGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAACC

ACAGGTGTACACCCTGCCCCCATCCCGGGATGAGCTGACCAAGAACCAGG

TCAGCCTGACCTGCCTGGTCAAAGGCTTCTATCCAAGCGACATCGCCGTG

GAGTGGGAGAGCAATGGGCAGCCGGAGAACAACTACAAGACCACGCCTCC

CGTGCTGGACTCCGACGGCTCCTTCTTCCTCTACAGCAAGCTCACCGTGG

ACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGG

TAAATGAGTGCGACGGCCGCGACTCTAGAGGAT

Example 10

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described in the Examples. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 11

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics are administered orally, rectally, parenterally, intracistemally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention are also suitably administered by sustained-release systems. Suitable examples of sustained-release Therapeutics include suitable polymeric materials (such as, for example, semi-permeable polymer matrices in the form of shaped articles, e.g., films, or mirocapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(-)-3-hydroxybutyric acid (EP 133,988).

Sustained-release Therapeutics also include liposomally entrapped Therapeutics of the invention (see generally, Langer, Science 249:1527–1533 (1990); Treat et al., in Liposomes in the Therapy of Infectious Disease and Cancer, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Therapeutic is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multidose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No.

WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the Therapeutics of the invention, include, but are not limited to, VIRAMUNE™ (nevirapine), RESCRIPTOR™ (delavirdine), and SUSTIVA™ (efavirenz). Protease inhibitors that may be administered in combination with the Therapeutics of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Therapeutics of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Therapeutics of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Therapeutics of the invention are used in any combination with RIFABUTIN™, CLARITHROMYCIN™, and/or AZITHROMYCN™ to prophylactically treat or prevent an opportunistic *Mycobacterium tuberculosis* infection. In another specific embodiment, Therapeutics of the invention are used in any combination with GANCICLOVIR™, FOSCARNET™, and/or CIDOFOVIR™ to prophylactically treat or prevent an opportunistic cytomegalovirus infection. In another specific embodiment, Therapeutics of the invention are used in any combination with FLUCONAZOLE™, ITRACONAZOLE™, and/or KETOCONAZOLE™ to prophylactically treat or prevent an opportunistic fungal infection. In another specific embodiment, Therapeutics of the invention are used in any combination with ACYCLOVIR™ and/or FAMCICOLVIR™ to prophylactically treat or prevent an opportunistic herpes simplex virus type I and/or type II infection. In another specific embodiment, Therapeutics of the invention are used in any combination with PYRIMETHAMINE™ and/or LEUCOVORIN™ to prophylactically treat or prevent an opportunistic *Toxoplasma gondii* infection. In another specific embodiment, Therapeutics of the invention are used in any combination with LEUCOVORIN™ and/or NEUPOGEN™ to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR™, IVEEGAM™, SANDOGLOBULIN™, GAMMAGARD S/D™, and GAMIMUNE™. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE™ (SARGRAMOSTIM™) and NEUPOGEN™ (FILGRASTIM™).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the Therapeutics of the invention are administered in combination with other therapeutic or prophylactic regimens, such as, for example, radiation therapy.

Example 12

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided in the Examples.

Example 13

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided in the Examples.

Example 14

Method of Treatment Using Gene Therapy—Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 1 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 15

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3' end. Two non-coding sequences are amplified via PCR: one non-coding sequence (fragment 1) is amplified with a HindIII site at the 5' end and an Xba site at the 3' end; the other non-coding sequence (fragment 2) is amplified with a BamHI site at the 5' end and a HindIII site at the 3' end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC 18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 16

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, LIPOFECTIN™ (liposome transfection reagent) or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 17

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 18

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra).

However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 19

Biological Effects of Polypeptides of the Invention

Astrocyte and Neuronal Assays

Recombinant polypeptides of the invention, expressed in *Escherichia coli* and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." Proc. Natl. Acad. Sci. USA 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays.

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. ALAMAR BLUE™ cell dye (Alamar Biosciences, Sacramento, Calif.) is added to each well to a final concentration of 10%. The cells are incubated for 4 hr. Cell viability is measured by reading in a CytoFluor fluorescence reader. For the $PGE_2$ assays, the human lung fibroblasts are cultured at 5,000 cells/well in a 96-well plate for one day. After a medium change to 0.1% BSA basal medium, the cells are incubated with FGF-2 or polypeptides of the invention with or without IL-1α for 24 hours. The supernatants are collected and assayed for $PGE_2$ by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1α for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of ALAMAR BLUE™ cell dye to assess effects on growth of the fibroblasts. FGF-2 should show a stimulation at 10–2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine ($MPP^+$) and released. Subsequently, $MPP^+$ is actively accumulated in dopaminergic neurons by the high-affinity reuptake transporter for dopamine. $MPP^+$ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm on polyorthinine-laminin coated glass coverslips. The cells are maintained in Dulbecco's Modified Eagle's medium and F12 medium containing hormonal supplements (N1). The cultures are fixed with paraformaldehyde after 8 days in vitro and are processed for tyrosine hydroxylase, a specific marker for dopminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

The studies described in this example tested activity of a polypeptide of the invention. However, one skilled in the art could easily modify the exemplified studies to test the activity of polynucleotides (e.g., gene therapy), agonists, and/or antagonists of the invention.

The entire disclosure of each document cited (including patents, patent applications, journal articles, abstracts, laboratory manuals, books, or other disclosures) in the Background of the Invention, Detailed Description, and Examples is hereby incorporated herein by reference.

The invention claimed is:

1. A method for treating epilepsy comprising administering to a patient in need thereof an effective amount of a polypeptide comprising a first polypeptide at least 97% identical to a second polypeptide selected from the group consisting of:
   (a) a polypeptide comprising amino acids 1–410 of SEQ ID NO:2;
   (b) a polypeptide comprising amino acids 19–410 of SEQ ID NO:2;
   (c) the complete polypeptide encoded by the cDNA clone contained in ATCC Deposit No. 97722; and,
   (d) the mature polypeptide encoded by the cDNA clone contained in ATCC Deposit No. 97722,
   wherein said first polypeptide inhibits tissue-type plasminogen activator (t-PA).

2. The method of claim 1, wherein the second polypeptide is (a).

3. The method of claim 2, wherein the first polypeptide is fused to a heterologous polypeptide.

4. The method of claim 1, wherein the second polypeptide is (b).

5. The method of claim 4, wherein the first polypeptide is fused to a heterologous polypeptide.

6. The method of claim 1, wherein the second polypeptide is (c).

7. The method of claim 6, wherein the first polypeptide is fused to a heterologous polypeptide.

8. The method of claim 1, wherein the second polypeptide is (d).

9. The method of claim 8, wherein the first polypeptide is fused to a heterologous polypeptide.

* * * * *